(12) United States Patent
Holt et al.

(10) Patent No.: US 11,473,958 B2
(45) Date of Patent: Oct. 18, 2022

(54) CAPACITIVE MEASUREMENT DEVICE WITH MINIMIZED SENSITIVITY TO MANUFACTURING VARIABILITY AND ENVIRONMENTAL CHANGES

(71) Applicant: Stream Dx, Inc, South Salt Lake, UT (US)

(72) Inventors: Brian Holt, North Salt Lake, UT (US); Scott McClellan, Park City, UT (US); Alvin Y. Le, Salt Lake City, UT (US); Kent Ogden, Murray, UT (US)

(73) Assignee: Stream Dx, Inc, South Salt Lake, UT (US)

( * ) Notice: Subject to any disclaimer, the term of this patent is extended or adjusted under 35 U.S.C. 154(b) by 0 days.

(21) Appl. No.: 16/616,406

(22) PCT Filed: May 22, 2018

(86) PCT No.: PCT/US2018/033974
§ 371 (c)(1),
(2) Date: Nov. 22, 2019

(87) PCT Pub. No.: WO2018/217818
PCT Pub. Date: Nov. 29, 2018

(65) Prior Publication Data
US 2020/0209044 A1    Jul. 2, 2020

Related U.S. Application Data

(60) Provisional application No. 62/509,397, filed on May 22, 2017.

(51) Int. Cl.
*G01F 23/263*    (2022.01)
*A61B 5/20*    (2006.01)
(Continued)

(52) U.S. Cl.
CPC ............ *G01F 23/266* (2013.01); *A61B 5/204* (2013.01); *A61B 5/208* (2013.01); *G01F 1/56* (2013.01);
(Continued)

(58) Field of Classification Search
CPC .... G01F 23/265; G01F 23/266; G01F 23/268; G01F 23/26; G01F 23/263; G01F 23/242;
(Continued)

(56) References Cited

U.S. PATENT DOCUMENTS 4,051,431 A    9/1977    Wurster
4,628,612 A    12/1986    Hori et al.
(Continued)

FOREIGN PATENT DOCUMENTS

RU    2026639 C1    1/1995
RU    2034516 C1    5/1995
(Continued)

OTHER PUBLICATIONS

"CLC Application Note V2", Jul. 29, 2015, pp. 1-3, Publisher: First Sensor.
(Continued)

*Primary Examiner* — John Fitzgerald
*Assistant Examiner* — Truong D Phan
(74) *Attorney, Agent, or Firm* — Fogg & Powers LLC

(57) ABSTRACT

A printed circuit board device includes: a first capacitive sensor configured to measure a first capacitance within a contained volume having known dimensions, wherein the first capacitance changes as a substance is received into the contained volume; a second capacitive sensor having a plurality of trigger points at a plurality of corresponding known heights within the contained volume, the second capacitive sensor configured to detect when the substance received into the contained volume has reached each of the
(Continued)

corresponding known heights within the contained volume; and wherein at least one of a level of the substance within the contained volume, a volume of the substance within the contained volume, or a flow rate of the substance into the contained volume is determined based on data from the first capacitive sensor and the second capacitive sensor.

25 Claims, 37 Drawing Sheets

(51) Int. Cl.
G01F 1/56 (2006.01)
G01N 33/493 (2006.01)
(52) U.S. Cl.
CPC ......... *G01F 23/268* (2013.01); *G01N 33/493* (2013.01)
(58) Field of Classification Search
CPC ...... G01F 23/241; G01F 1/56; G01F 25/0061; G01F 1/007; A61B 2560/0223; A61B 2560/0247; A61B 2560/0252; A61B 5/202; A61B 5/204; A61B 5/207; A61B 5/208; G01N 27/22; G01N 33/493
See application file for complete search history.

(56) References Cited

U.S. PATENT DOCUMENTS

| | | | |
|---|---|---|---|
| 5,311,769 A | 5/1994 | Hetzel | |
| 5,423,206 A | 6/1995 | Hetzel | |
| 5,495,854 A * | 3/1996 | Currie | A61B 5/208 600/573 |
| 5,672,831 A | 9/1997 | Codina et al. | |
| 5,726,908 A | 3/1998 | Hosmer et al. | |
| 5,769,087 A | 6/1998 | Westphal et al. | |
| 6,125,696 A | 10/2000 | Hannan et al. | |
| 6,490,920 B1 | 12/2002 | Netzer | |
| 6,628,395 B2 * | 9/2003 | Liu | G01F 23/292 250/577 |
| 7,188,426 B2 | 3/2007 | Barr | |
| 7,258,005 B2 | 8/2007 | Nyce | |
| 7,360,424 B2 | 4/2008 | Urano et al. | |
| 7,483,805 B2 | 1/2009 | Sparks et al. | |
| 7,611,500 B1 | 11/2009 | Lina et al. | |
| 7,691,092 B2 | 4/2010 | Corcos et al. | |
| 7,722,584 B2 | 5/2010 | Tanaka et al. | |
| 7,845,224 B2 | 12/2010 | Barlesi et al. | |
| 8,116,993 B2 | 2/2012 | Cebulski | |
| 8,337,476 B2 | 12/2012 | Greenwald et al. | |
| 8,549,764 B2 | 10/2013 | Muyskens et al. | |
| 8,924,005 B2 | 12/2014 | Kern | |
| 8,986,613 B2 | 3/2015 | Cohen | |
| 10,448,875 B2 | 10/2019 | Holt et al. | |
| 2008/0081000 A1 | 4/2008 | MacLeod et al. | |
| 2008/0278180 A1 * | 11/2008 | Feldman | G01R 31/34 324/686 |
| 2009/0031790 A1 | 2/2009 | Guo et al. | |
| 2009/0301190 A1 * | 12/2009 | Ross, Jr. | G01F 25/0061 73/304 C |
| 2010/0094173 A1 * | 4/2010 | Denton | A61M 1/7413 600/584 |
| 2011/0083504 A1 | 4/2011 | Unger | |
| 2012/0123233 A1 | 5/2012 | Cohen | |
| 2015/0105694 A1 | 4/2015 | Mahajan | |
| 2017/0105670 A1 | 4/2017 | Holt et al. | |
| 2017/0119300 A1 * | 5/2017 | Conner | A61B 5/746 |

FOREIGN PATENT DOCUMENTS

| | | |
|---|---|---|
| RU | 2256884 C2 | 7/2005 |
| WO | 9910714 A1 | 3/1999 |
| WO | 2014141234 A1 | 9/2014 |
| WO | 2014145971 A2 | 9/2014 |
| WO | 2015153470 A1 | 10/2015 |
| WO | 2017066470 A1 | 4/2017 |

OTHER PUBLICATIONS

"CLC Performance Optimization", Sep. 2015, pp. 1-3, Publisher: First Sensor.
"CLC Series Miniature Capacitive Continuous Liquid Level Sensors", Jul. 2015, pp. 1-6, Publisher: First Sensor.
"Measuring Transition Points in Liquids with Different Densities with CLC and CLW Capacitive Level Sensors", Jul. 2013, pp. 1-3, Publisher: First Sensor.
"Projected Capacitive Technology", "Touch Technology Brief", Oct. 2013, pp. 1-8, Publisher: 3M.
"Stream Dx About US Webpage", "http://streamdxmed.com/aboutus/", at least as early as Oct. 13, 2015, pp. 1-4.
"Stream Dx Home Page", "http://streamdxmed.com/", at least as early as Oct. 13, 2015, No. 1-2.
"Stream DX Poster, Bench to Bedside, University of Utah Health Sciences", Apr. 2015, p. 1, Publisher: Stream DX, Inc.
Barrett et al., "Projected-Capacitive Touch Technology", "Frontline Technology", Mar. 2010, pp. 16-21, Publisher: Information Display.
Chiang, Cheng-Ta, "A Semicylindrical Capacitive Sensor with Interface Circuit Used for Flow Rate Measurement", "IEEE Sensors Journal", Dec. 6, 2006, pp. 1564-1570, vol. 6, No. 6, Publisher: IEEE.
International Bureau, "International Preliminary Report on Patentability from PCT Application No. PCT/US2018/033974", from Foreign Counterpart to U.S. Appl. No. 16/616,406, dated Dec. 5, 2019, pp. 1-8, Published: WO.
International Searching Authority, "International Search Report and Written Opinion from PCT Application No. PCT/US18/33974", Aug. 2, 2018, pp. 1-16, Published: WO.
Liu et al., "A New Cylindrical Capacitance Sensor for Measurement of Water Cut in a Low-production Horizontal Well", "Journal of Physics: Conference Series 147; The 6th International Symposium on Measurement Techniques for Multiphase Flows", at least as early as Dec. 2009, pp. 1-7, Publisher: IOP Publishing.
Otero et al., "A New Device to Automate the Monitoring of Critical Patients' Urine Output", "BioMed Research International", Jan. 28, 2014, pp. 1-8, vol. 2014, Publisher: Hindawi Publishing Corporation.
Paillat et al., "'Capacitive Sensor' to Measure Flow Electrification and Prevent Electrostatic Hazards", "Sensors", Oct. 25, 2012, pp. 14315-14326.

* cited by examiner

CAPACITIVE MEASUREMENT DEVICE WITH MINIMIZED SENSITIVITY TO MANUFACTURING VARIABILITY AND ENVIRONMENTAL CHANGES

CROSS-REFERENCE TO RELATED APPLICATIONS

This application is a U.S. National Stage Patent Application of International Application PCT/US2018/033974 filed on May 22, 2018 and titled "CAPACITIVE MEASUREMENT DEVICE WITH MINIMIZED SENSITIVITY TO MANUFACTURING VARIABILITY AND ENVIRONMENTAL CHANGES", which claims the benefit of U.S. Provisional Patent Application Ser. No. 62/509,397 filed on May 22, 2017, entitled "CAPACITIVE MEASUREMENT DEVICE WITH INTEGRATED ELECTRICAL AND MECHANICAL SHIELDING", which are all hereby incorporated herein by reference in their entirety.

BACKGROUND

Uroflowmetry is the measure of the volume of urine released from the body, the rate at which urine is voided, and the time it takes to complete a voiding event. The results of a uroflowmetry test can be very beneficial in evaluating the health of the urinary tract. This test can also be very valuable in diagnosing abnormal health conditions, such as lower urinary tract symptoms, benign prostatic hypertrophy, prostate cancer, bladder tumor, neurogenic bladder dysfunction, urinary incontinence, urinary blockage, urinary tract infection, as well as other conditions. Traditionally, uroflowmetry tests are conducted at a medical facility, such as a hospital or clinic. Testing in an artificial clinical setting opposed to a natural setting such as the patient's home can have a significant impact on the patient's performance. In addition to the obvious disadvantages of inconvenience and patient compliance, one complication that often arises with in-clinic testing is that the patient will need to urinate while waiting for the test to be administered. This can result in premature voiding or abnormal voiding events, which skew or negate the value of the test and require the patient to return to the clinic multiple times to get accurate results.

SUMMARY

A printed circuit board device includes: a first capacitive sensor configured to measure a first capacitance within a contained volume having known dimensions, wherein the first capacitance changes as a substance is received into the contained volume; a second capacitive sensor having a plurality of trigger points at a plurality of corresponding known heights within the contained volume, the second capacitive sensor configured to detect when the substance received into the contained volume has reached each of the corresponding known heights within the contained volume; and wherein at least one of a level of the substance within the contained volume, a volume of the substance within the contained volume, or a flow rate of the substance into the contained volume is determined based on data from the first capacitive sensor and the second capacitive sensor.

DRAWINGS

Understanding that the drawings depict only exemplary embodiments and are not therefore to be considered limiting in scope, the exemplary embodiments will be described with additional specificity and detail through the use of the accompanying drawings, in which.

In accordance with common practice, the various described features are not drawn to scale but are drawn to emphasize specific features relevant to the exemplary embodiments. Like reference numbers and designations in the various drawings indicate like elements.

DETAILED DESCRIPTION

Figure 1A:
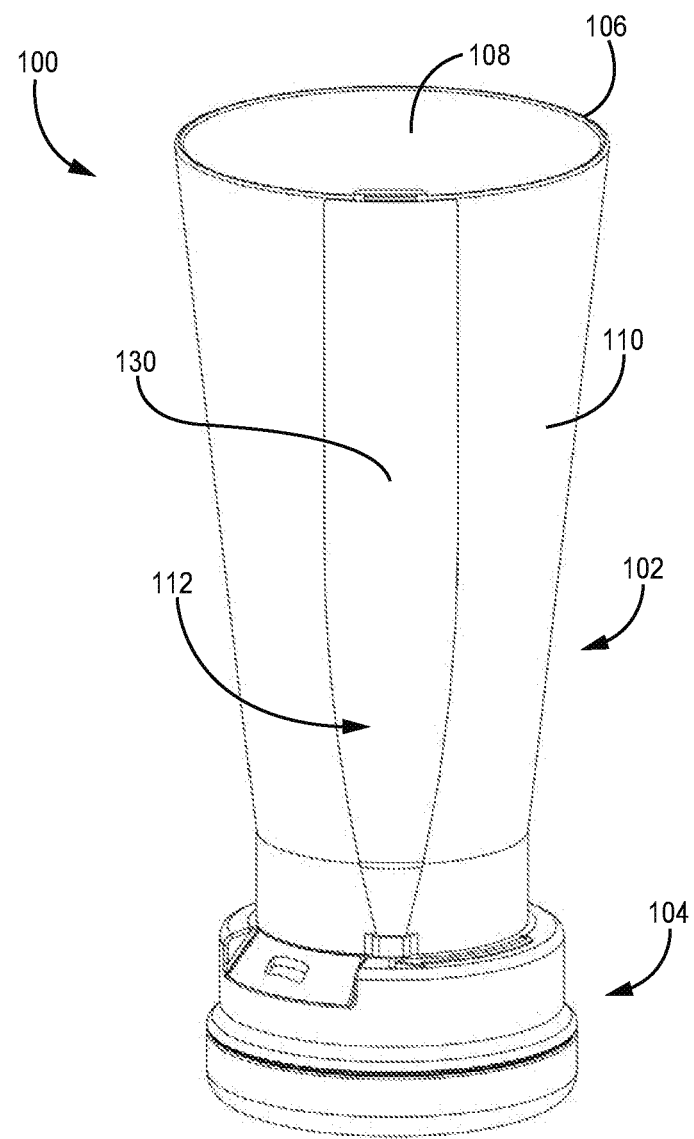
FIG. 1A is a top perspective view of an example of a urine measurement device, including a container portion and an electronics portion.

In the following detailed description, reference is made to the accompanying drawings that form a part hereof, and in which is shown by way of illustration specific illustrative embodiments. However, it is to be understood that other embodiments may be utilized and that logical, mechanical, and electrical changes may be made. Furthermore, the method presented in the drawing figures and the specification is not to be construed as limiting the order in which the individual steps may be performed. The following detailed description is, therefore, not to be taken in a limiting sense.

Medication Therapy Management (MTM) includes medical care provided by pharmacists whose aim is to optimize drug therapy and improve therapeutic outcomes for patients. MTM can be a significant challenge because patient compliance as well as changing medical conditions place an emphasis on continuously monitoring or tracking the patient's condition. This high degree of patient condition monitoring often requires a hospital or intensive care unit setting. However technology advances and through leveraging smart-devices, at home MTM can offer significant health benefits, especially for recovering heart failure patients.

The 30-day readmission rate for heart failure patients results in enormous additional expenses. Upon release from a hospital after a heart failure incident, a patient's health and recovery is largely dependent on the amount of fluids they consume and the amount of urine they void. Accumulation of fluids or fluid retention is bad for a recovering heart failure patient as it places additional load on the heart, potentially requiring hospital readmission. An excess of fluid loss can lead to dehydration which also places unnecessary additional load on the heart. Proper management of the patient's fluid load can significantly improve the patient's condition and minimize 30-day readmission rates to the hospital.

Proper management of the patient's fluid load can result in improved patient outcomes. Successful MTM generally includes collection of at least three things: (1) tracking urine voided; (2) tracking fluid intake; and (3) measuring urine creatinine (and other) levels over a 24-hour period. It has been difficult previously to effectively collect these three things at home or otherwise remote from a medical facility. Aspects of the examples described herein enable the collection of these three things at home or otherwise remote from a medical facility.

In examples, a urine measurement device includes a container portion and an electronics portion that are configured to be connected together. While this description places primary focus on uroflowmetry, it is understood that the description herein can apply more broadly to a substance measurement and/or analysis device that can make measurements about a substance entering into the container portion. In examples, the substance is urine or another bodily fluid, though other liquids, fluids, and/or solids could also be measured.

Figure 1B:
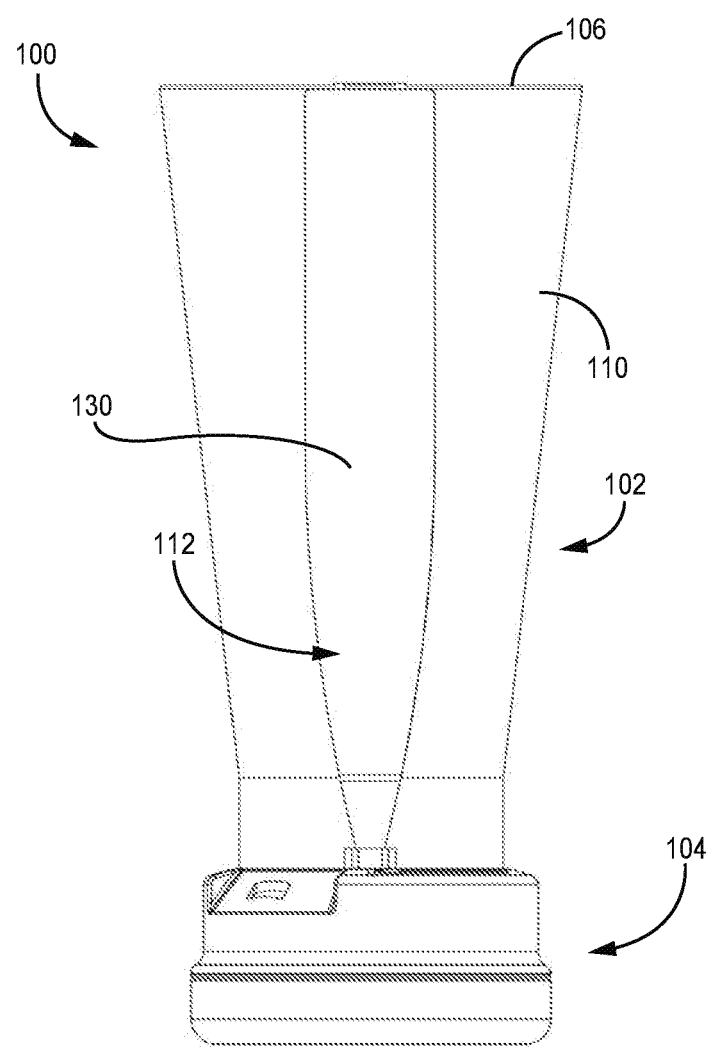
FIG. 1B is a side view of an example of the urine measurement device of FIG. 1A.
Figure 1C:
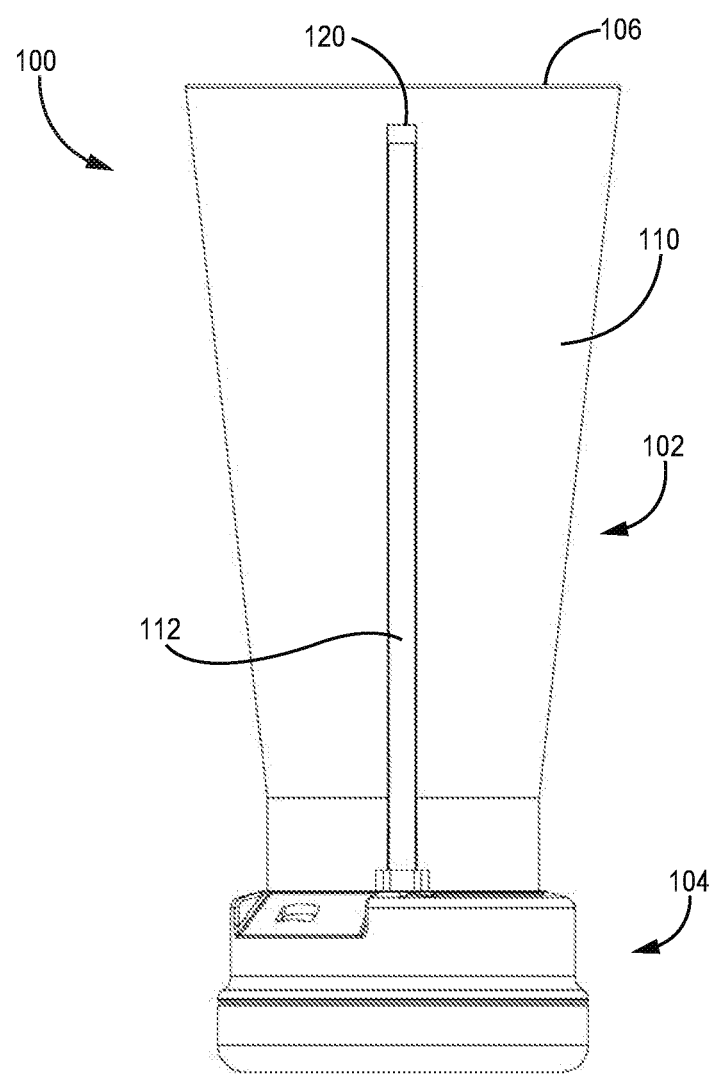
FIG. 1C is a side view of an example of the urine measurement device of FIG. 1A without the exterior shield so that the capacitive sensor can be seen.
Figure 1D:
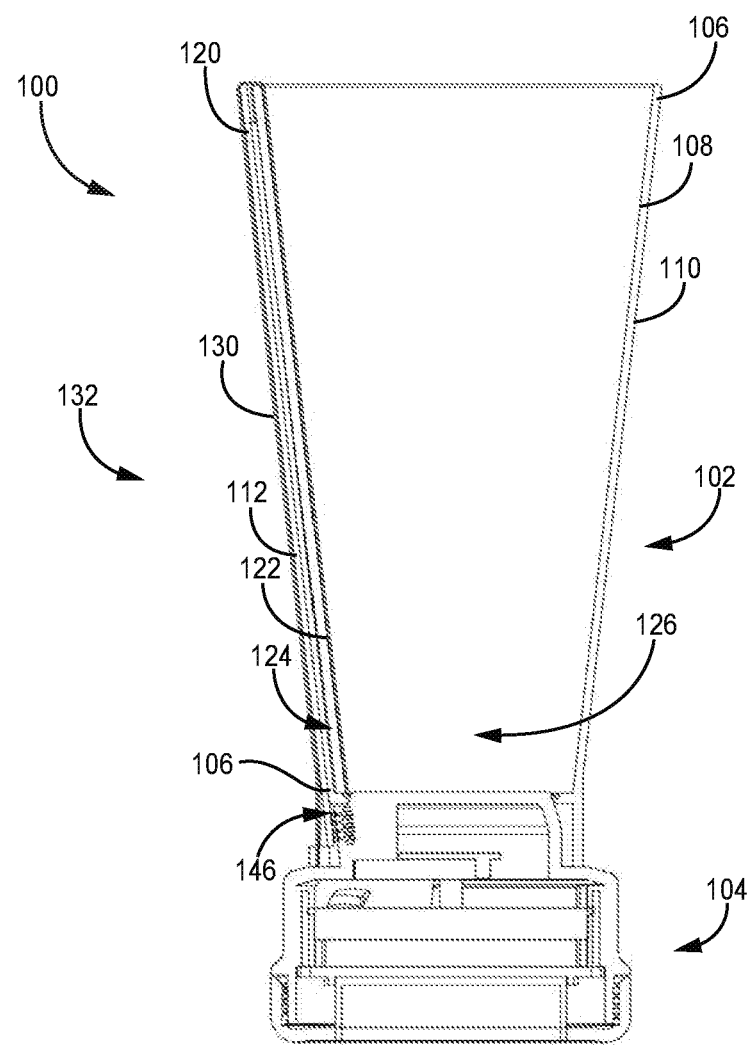
FIG. 1D is a cross-sectional side view of an example of the urine measurement device of FIG. 1A.
Figure 2A:
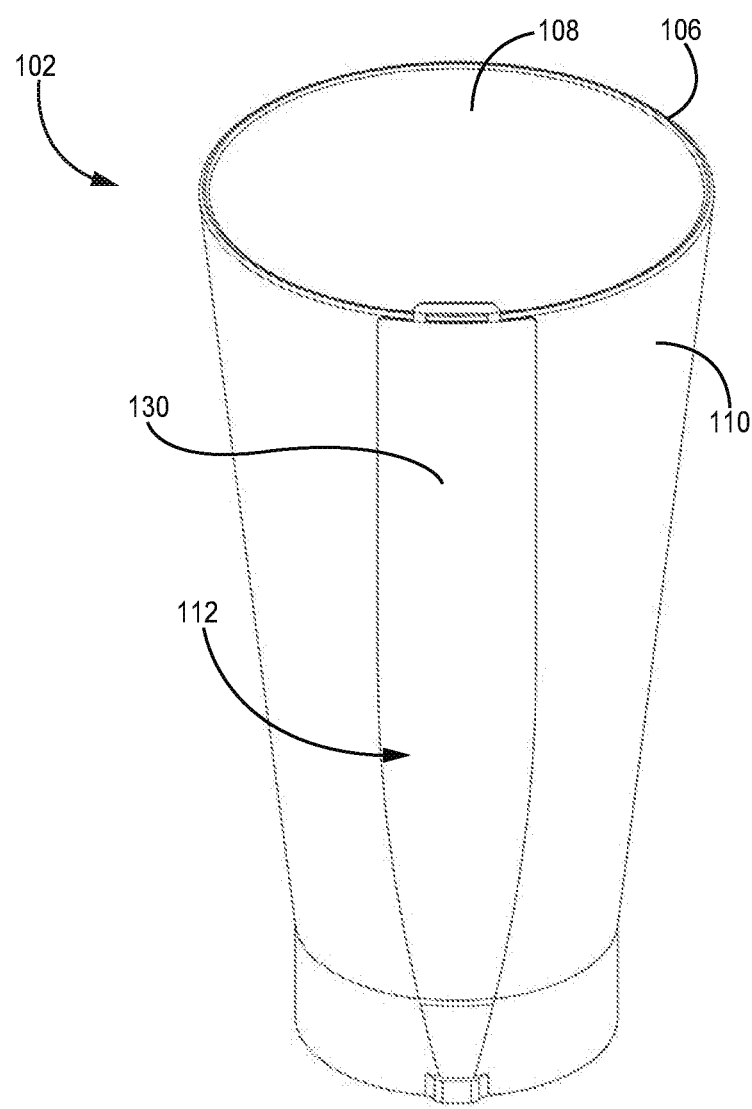
FIG. 2A is a top perspective view of an example of the container portion of the urine measurement device of FIG. 1A.
Figure 2B:
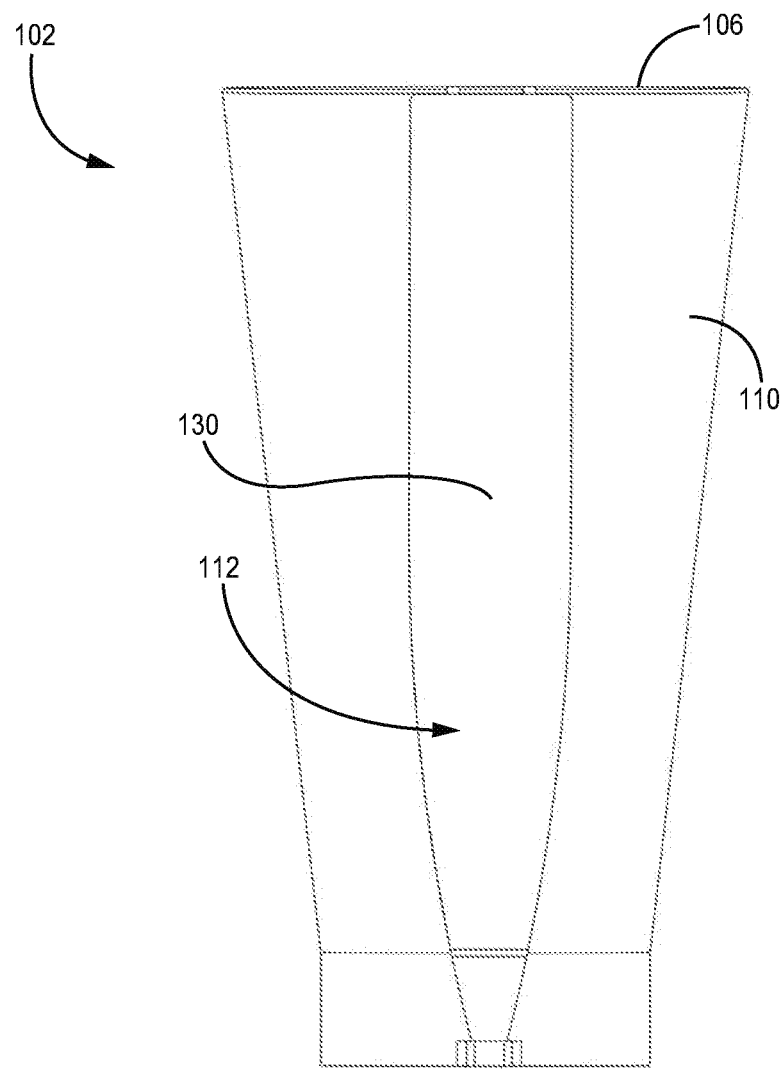
FIG. 2B is a side view of an example of the container portion of FIG. 2A.
Figure 2C:
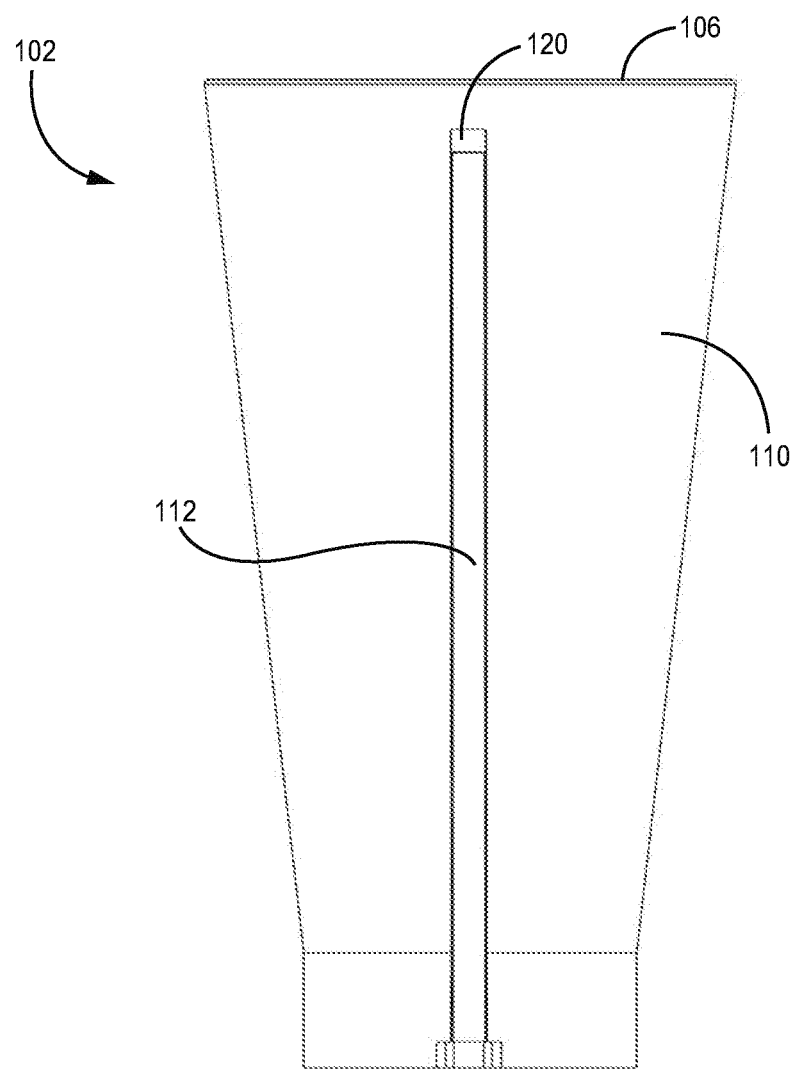
FIG. 2C is a side view of an example of the container portion of FIG. 2A without the exterior shield so that the capacitive sensor can be seen.
Figure 2D:
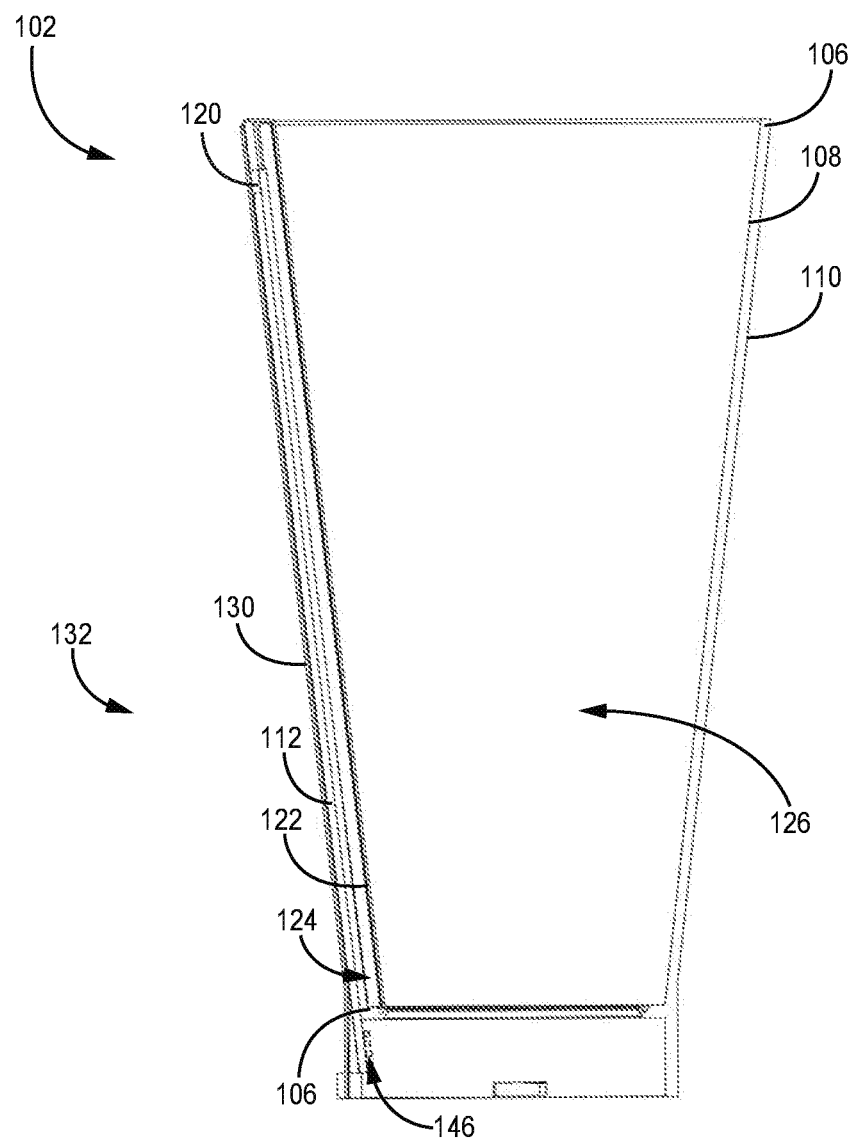
FIG. 2D is a cross-sectional side view of an example of the container portion of FIG. 2A.
Figure 2E:
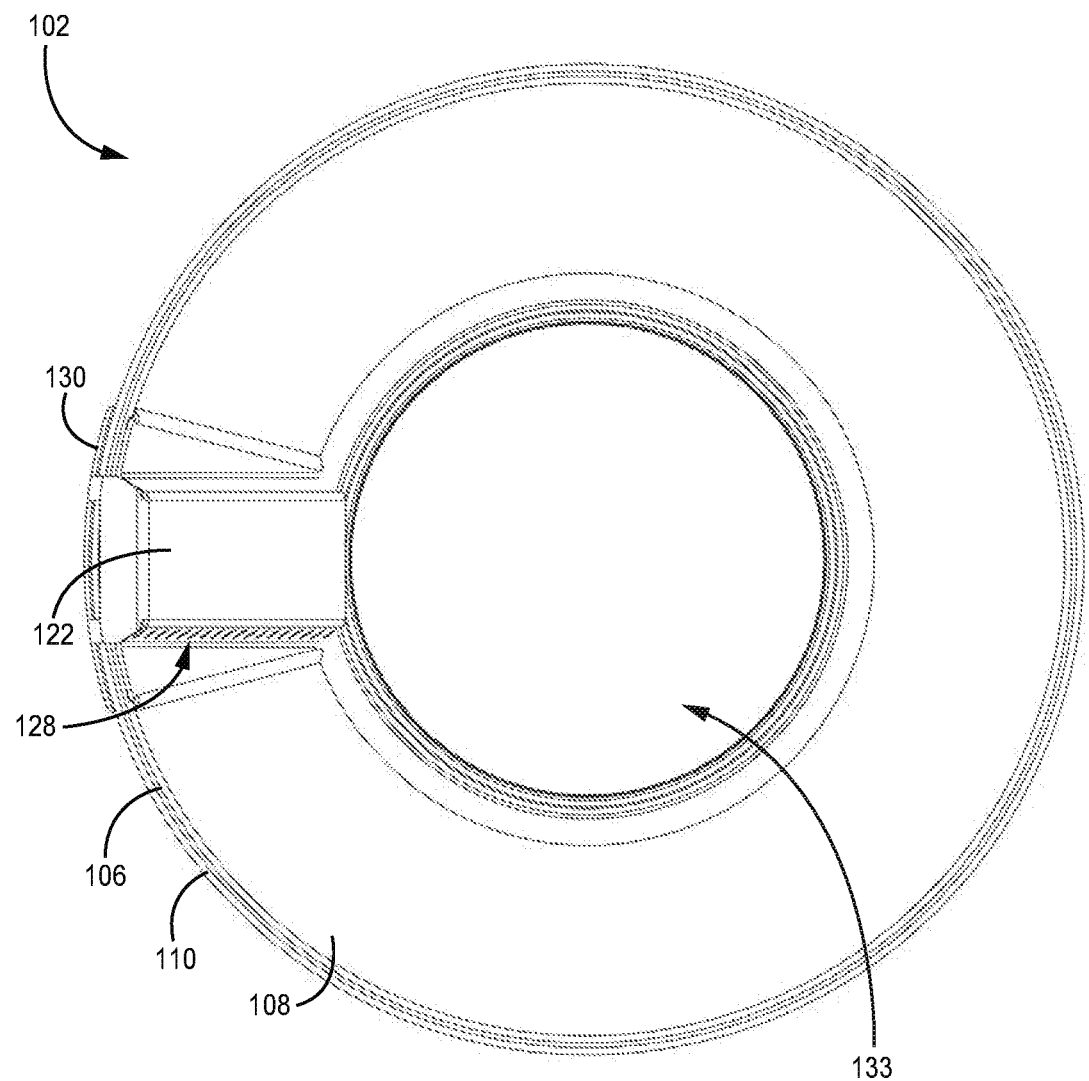
FIG. 2E is a top view of an example of the container portion of FIG. 2A.
Figure 2F:
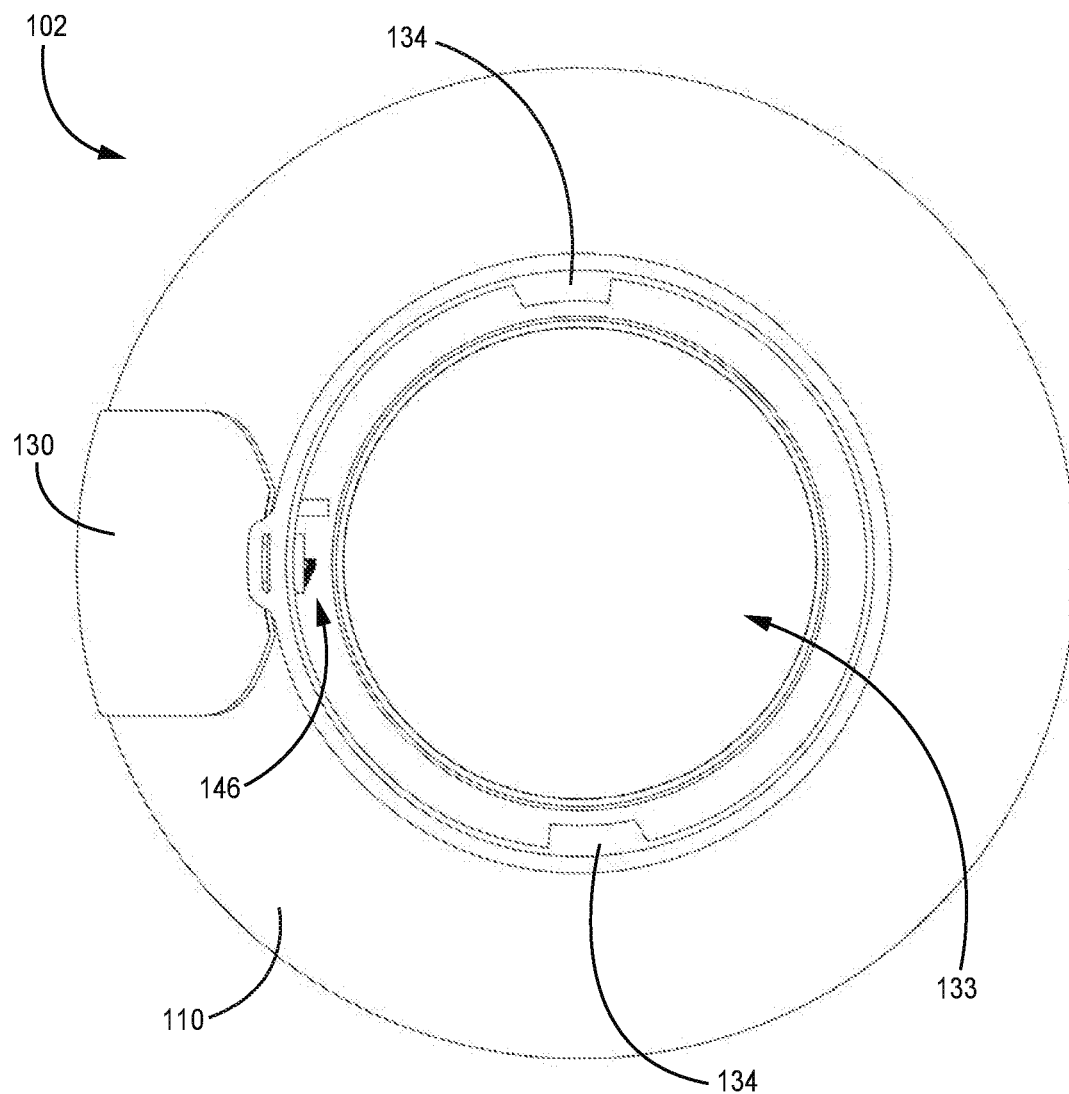
FIG. 2F is a bottom view of an example of the container portion of FIG. 2A.
Figure 2G:
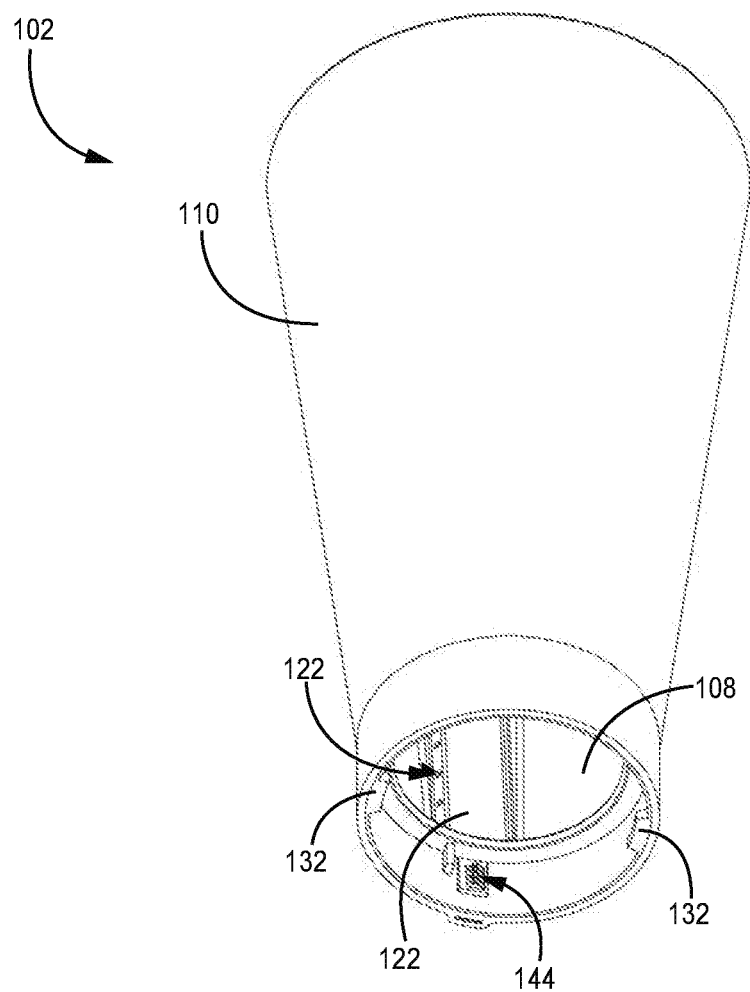
FIG. 2G is a bottom perspective view of an example of the container portion of FIG. 2A.
Figure 3A:
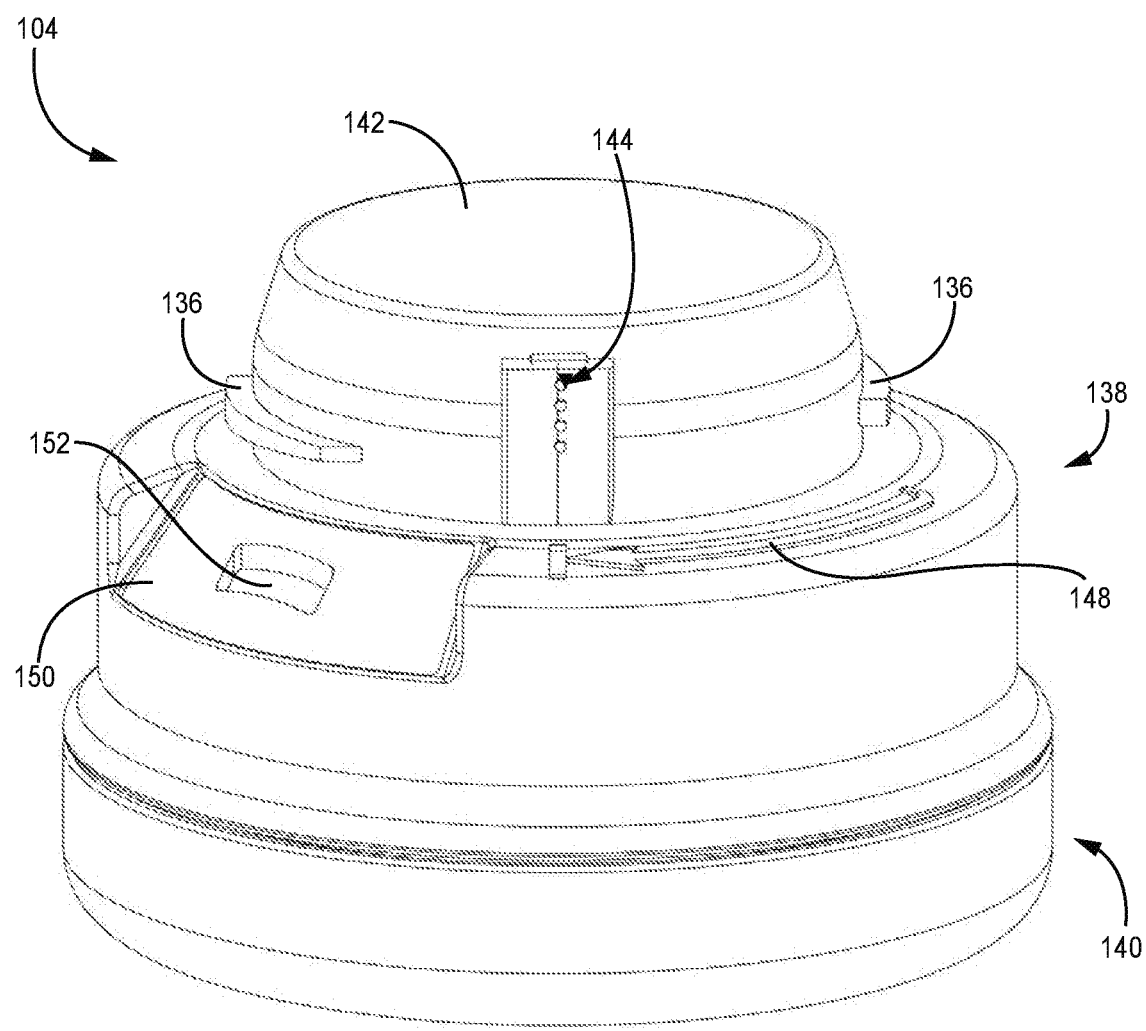
FIG. 3A is a top perspective view of an example of the electronics portion of the urine measurement device of FIG. 1A.
Figure 3B:
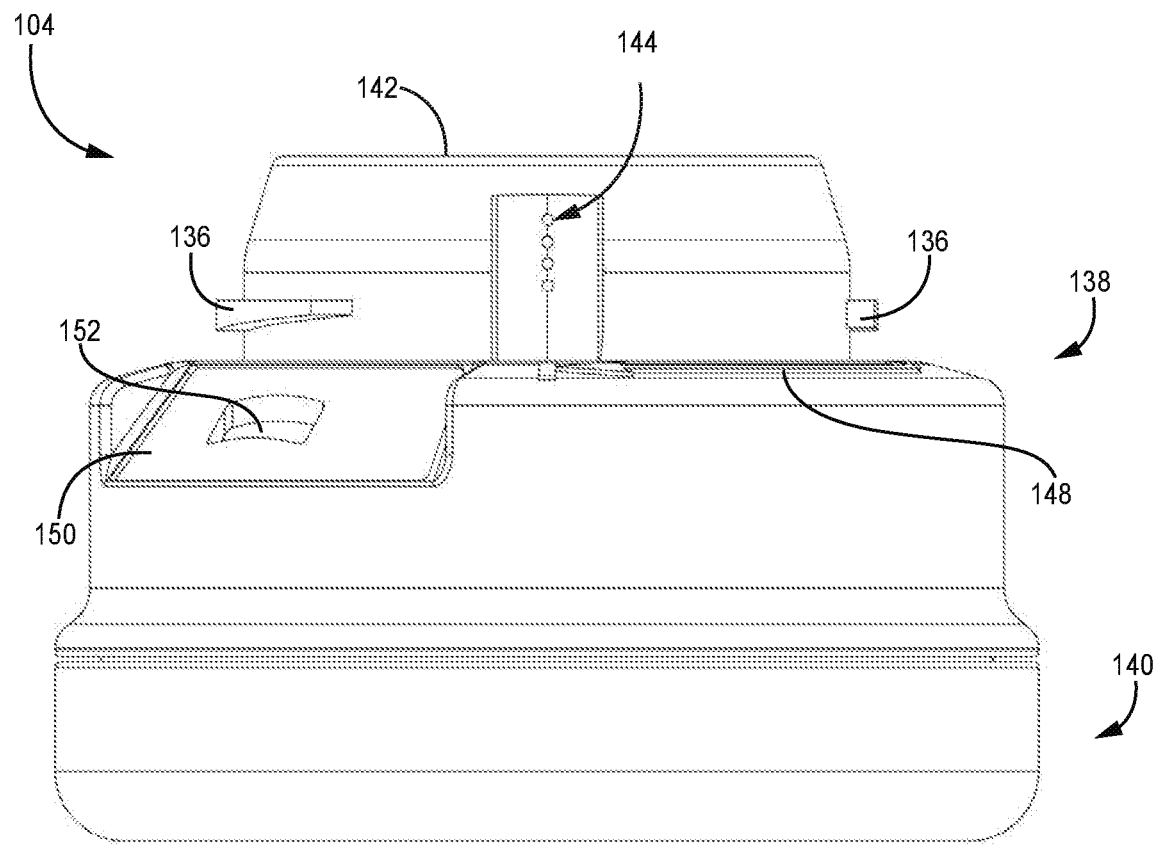
FIG. 3B is a side view of an example of the electronics portion of FIG. 3A.
Figure 3C:
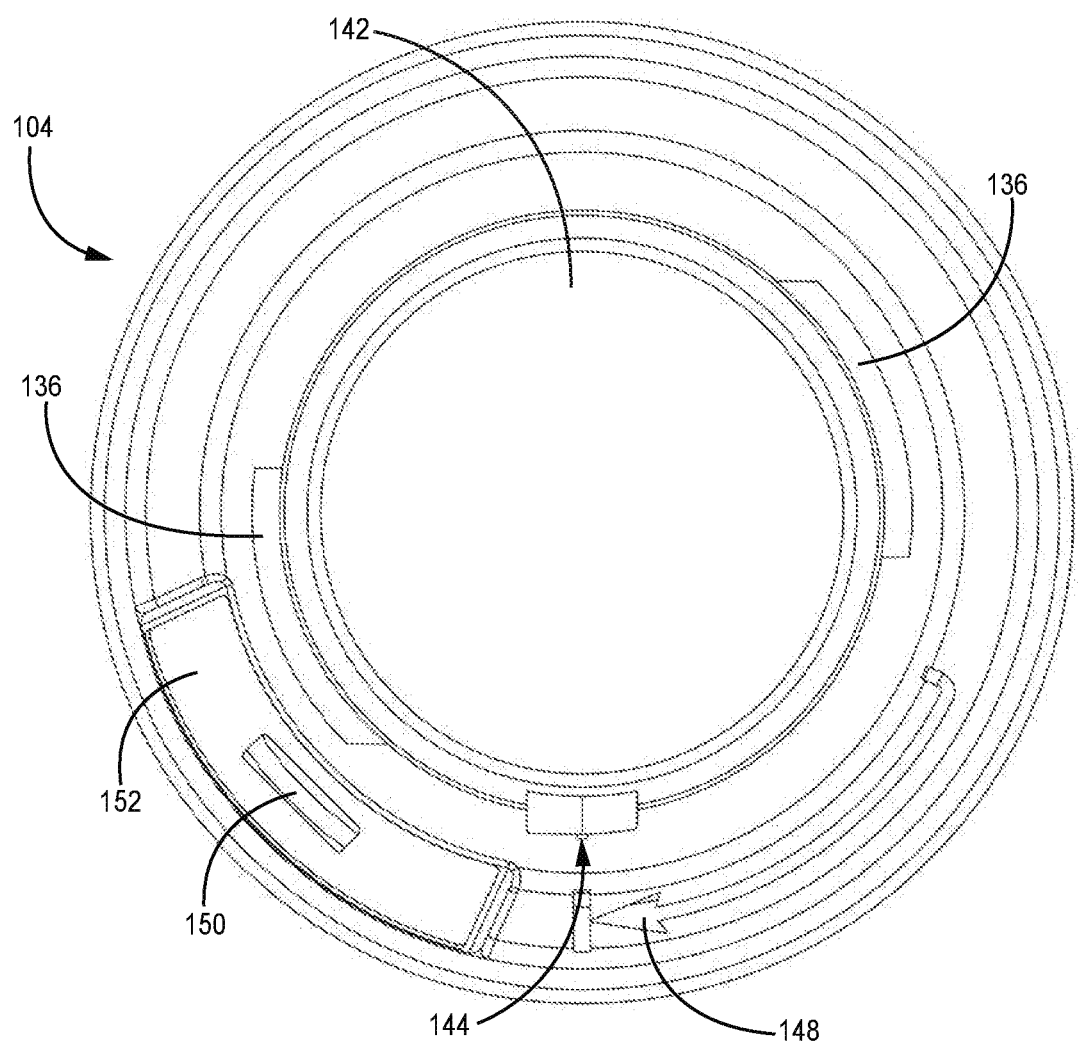
FIG. 3C is a top view of an example of the electronics portion of FIG. 3A.
Figure 4:
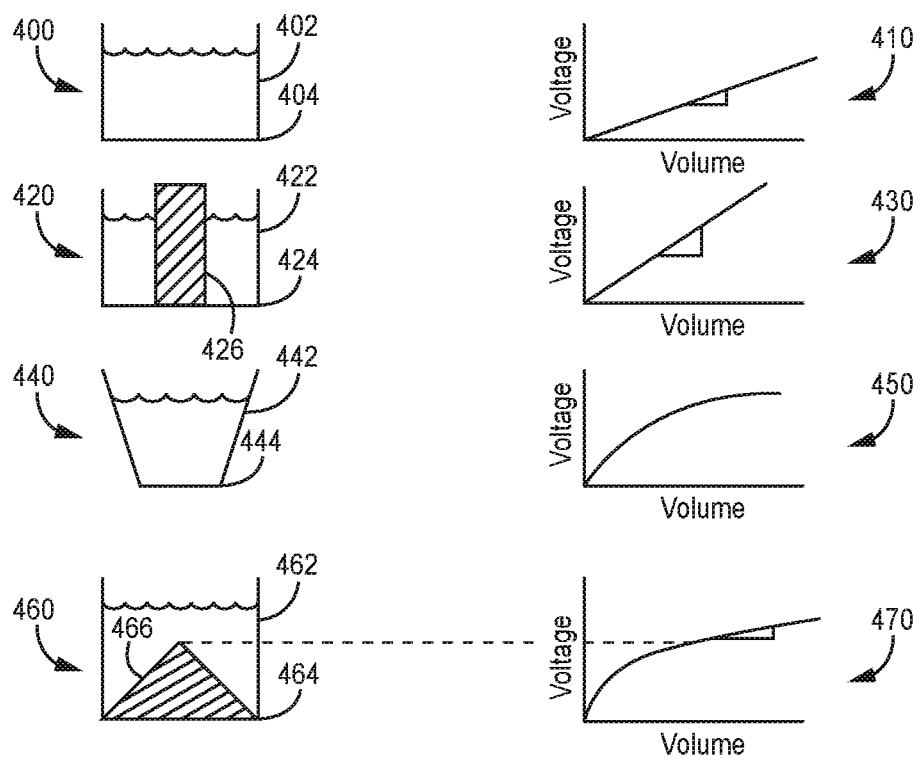
FIG. 4 shows different embodiments of the impact on the relationship between voltage and volume due to different geometries of the container portion and/or electronics portion of the urine measurement device of FIG. 1A.

FIGS. 1A-1D show different views of an example of a urine measurement device 100 (or another fluid measurement device or another substance measurement device), including a container portion 102 and an electronics portion 104. FIG. 1A is a perspective view of the urine measurement device 100, FIG. 1B is a side view of the urine measurement device 100, FIG. 1C is a side view of the urine measurement device 100, without at least one exterior shield 130 such that capacitive sensor 112 positioned in the channel 120 can be seen, and FIG. 1D is a cross-sectional side view of the urine measurement device 100 rotated 90 degrees from FIGS. 1B and 1C. FIGS. 2A-2G show different views of an example of the container portion 102 of the urine measurement device 100. FIG. 2A is a perspective view of the container portion 102, FIG. 2B is a side view of the container portion 102, FIG. 2C is a side view of the container portion 102 without the at least one exterior shield 130 such that capacitive sensor 112 positioned in the channel 120 can be seen, FIG. 2D is a cross-sectional side view of the container portion 102 rotated 90 degrees from FIGS. 2B and 2C, FIG. 2E is a top view of the container portion 102, FIG. 2F is a bottom view of the container portion 102, FIG. 2G is a bottom perspective view of the container portion 102. FIGS. 3A-3C show different views of an example of the electronics portion 104 of the urine measurement device 100. FIG. 3A is a perspective view of the electronics portion 104, FIG. 3B is a side view of the electronics portion 104, and FIG. 3C is a top view of the electronics portion 104. FIG. 4 shows different embodiments of the impact on the relationship between voltage and volume due to different geometries of the container portion 102 and/or electronics portion 104.

Figure 5:
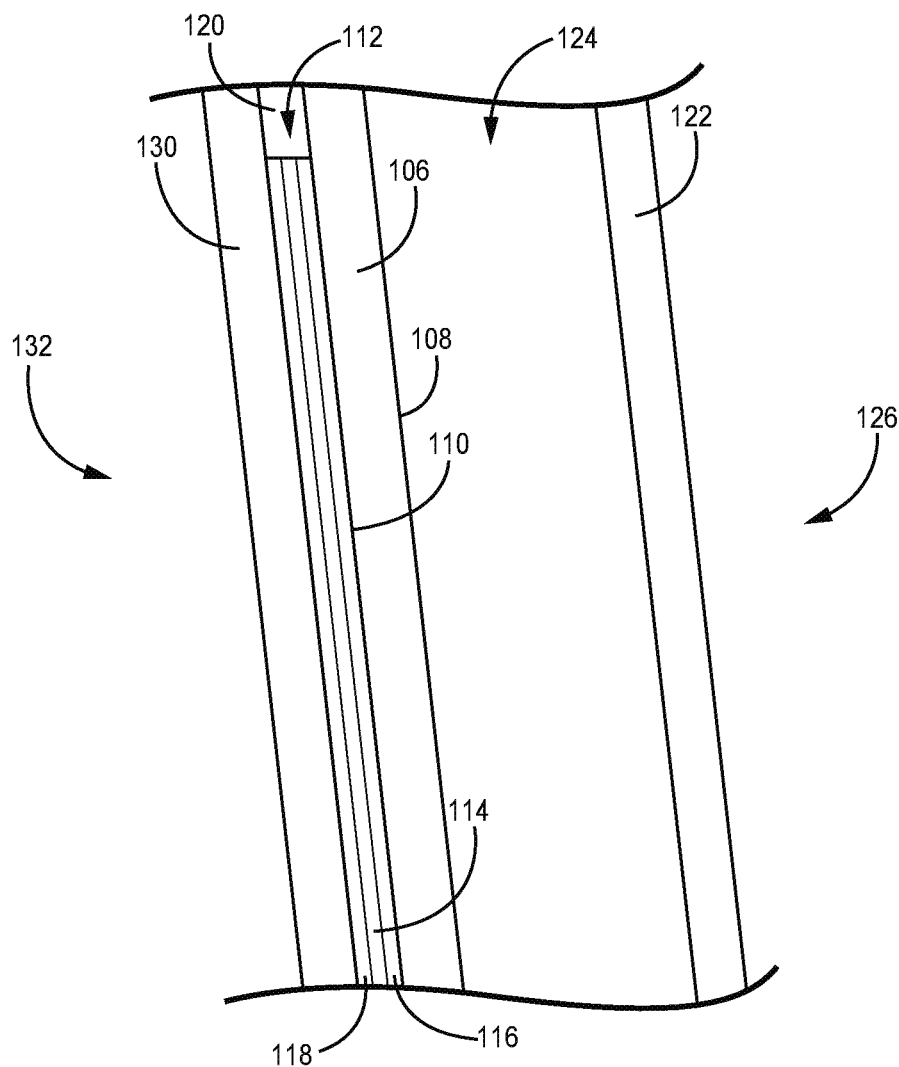
FIG. 5 is an enlarged cross-sectional side view of a portion of an example of the urine measurement device of FIG. 1A.

FIG. 5 is an enlarged cross-sectional side view of the curved side-wall 106, capacitive sensor 112, interior shield 122, and exterior shield 130 of the container portion 102 of the urine measurement device 100. The description below describes features shown in FIGS. 1A-1C, FIGS. 2A-2F, FIGS. 3A-3C, FIG. 4, and FIG. 5.

In examples, the urine measurement device 100 is a hand-held device for use by men and/or women while voiding/urinating. In examples, funnels and/or other attachments are placed on top of the container portion 102 and may have different shapes for male and female users. In examples, the funnel and/or geometry of the container portion 102 aid in minimizing splash back from urine or other substance that enters into the container portion 102. In examples, the device can be attached in or on the toilet so that the user can be seated on the toilet during the measurement. In examples, the hand-held nature of the urine measurement device 100 introduces potential issues such as tilting and/or shaking of the urine measurement device 100 that may cause measurement errors of flow rate, fluid height, volume, etc. Features of the urine measurement device 100 described herein mitigate the effects of and/or reduce the likelihood of occurrence of the tilting and/or shaking of the urine measurement device.

Measuring fluid flow and fluid volume (such as urine) in a portable environment has many potential sources of error, including significant deviation from the horizontal plane (device is out of level), too much movement/motion while holding the device (sloshing and splashing), mal-alignment or miss-installation of the sleeve, weak or low batteries/power supply, a mal-functioning or defective sensor, an out of spec calibration sensor, an inaccurate calibration or failure to calibrate within a known specified tolerance among other possible failure modes. In examples, a sensor complement and/or a plurality of sensors (accelerometers and/or angular acceleration sensors) is used to determine the orientation of a weight-based collection vessel of urine or other bodily fluids for the purposes measuring flow and/or volume to improve accuracy. In examples, visual (FIG. 3A, 152), audible, haptic or any other identifier are used to indicate an unacceptable or near unacceptable condition of a measurement system (that the device is within an acceptable horizontal level to take accurate data) prior to use. The warning may be delivered to the user via an app that is connected to the measuring device. In examples, error conditions (describing the problem and/or faulty condition(s)) are stored to memory and/or in a data file to facilitate post processing and data quality assessment.

The container portion 102 can be various shapes and sizes and can include or not include bottom walls and/or top walls. In examples, the container portion 102 includes a curved side-wall 106 having an interior surface 108 and an exterior surface 110, but does not include any top or bottom walls. Accordingly, in some embodiments, the container portion 102 is referred to as a sleeve, without a top or bottom. In these embodiments, the container portion 102 is only able to contain urine, another fluid, and/or substance once it is physically attached to the electronics portion 104, where the top surface of the electronics portion 104 serves as a bottom wall for the container portion 102. In other examples, the container portion 102 includes a bottom wall 133 having an interior surface and an exterior surface, such that the container portion can contain urine, another fluid, and/or other substance even when it is not physically attached to the electronics portion 104. In examples, the container portion 102 includes at least one coupling element 134 (such as threads, bayonet mounts, friction fit, tabs, clips, and/or fasteners) complimentary to at least one coupling element 136 on the electronics portion 104. While the container portion 102 is generally referred to as having a curved side-wall 106, it is understood that embodiments of the container portion 102 can have straight side-walls and have different geometries.

The volume to height ratio of the container portion 102 is related to the geometry of the container portion 102. Accordingly, the resolution of the urine measurement device 100 is a function of the geometry of the container portion 102 which holds the urine, other fluid, and/or other substance. In examples, the side-wall 106 of the container portion 102 includes a conical taper outward from a narrow bottom section to a wider top section (similar in shape to an ice cream cone). In examples, the conical taper provides higher resolution at lower volumes and lower resolution at higher volumes, such that the relationship between height and volume is non-linear throughout the container portion 102. For example, one millimeter of increased fluid height near the bottom of the container portion 102 may equal one milliliter of volume, while one millimeter of increased fluid height near the top of the container portion 102 may equal 5 milliliters of volume (in other words, 1 millimeter of height change near the bottom of the container portion 102 gives the same voltage change as 1 millimeter of height change near the top of the container portion 102, while the volume change would be smaller near the bottom of the container portion 102 than near the top of the container portion 102—an increased change in voltage per change in volume results in higher resolution). In examples, the software and electronics in the electronics portion 104 accounts for the taper and relationship between height and volume in the various sections of the tapered container portion 102 into account when calculating volume and/or flow rate of the urine, other fluid, and/or other substance. While a container portion 102 having a conical taper is shown in FIG. 1, other embodiments have different shapes, such as the straight non-tapered side-wall 106 in the embodiment of FIG. 7 described below which has a linear relationship between height and volume throughout the tapered container portion 102.

In examples, additional changes can be made to the container portion 102, the electronics portion 104, and/or inserts designed to be placed within the container portion 102 to enable higher resolution at lower volumes. In examples, inserts can be placed into the container portion 102 to augment the height to volume ratio instead of (or in addition to) making changes to the geometry of the container portion 102 itself. In examples, a conical shape which is larger at the bottom and smaller at the top can be inserted into the container portion 102 to achieve similar increased resolution at the bottom of the container portion 102 when the urine, other fluid, and/or other substance first begins to enter the container portion 102 and lower resolution as the urine, other fluid, and/or other substance rises within the container portion 102. In examples where the container portion 102 includes a bottom wall 133, the bottom wall 133 itself can be shaped to increase the resolution throughout the container portion 102 or at lower portions of the container portion 102. In examples, the top surface of the electronics portion 104 can extend up into the container portion 102 in various shapes, such as a rod, cone, pyramid, etc. By allowing for different shaped container portions 102, electronics portions 104, and or the addition of different shaped inserts, the urine measurement device 100 can be customized based on the user's needs. For example, if the user is a pediatric patient, an older patient, or any other patient producing lower quantities of urine at each voiding event, the urine measurement device 100 can be augmented to have increased resolution at lower volumes.

In examples, changing the geometry changes the data output profile and the relationship between voltage and volume at different geometries. Examples of the impact on the relationship between voltage and volume to different geometries is shown in FIG. 4. Geometry 400, with a straight vertical side-wall 402 and a flat bottom surface 404 results in a linear relationship between voltage and volume as shown in graph 410, having a constant slope throughout the volume of the geometry 400. Geometry 420, with a straight vertical side-wall 422, a flat bottom surface 424, and a cylindrical shaped center insert 426 results in a linear relationship between voltage and volume as shown in graph 430, having a constant slope throughout the volume of the geometry 420 that is steeper that the slope in graph 410. Geometry 440, with a tapered sidewall 442 and a flat bottom surface 444 results in a non-linear relationship between voltage and volume as shown in graph 450, having a changing slope throughout the volume of the geometry 440. Geometry 460, with a straight side-wall 462, a flat bottom surface 464, and a conical shaped center insert 466 results in a partially linear and partially non-linear relationship between voltage and volume as shown in graph 470, having a non-constant slope portion within the height ranges corresponding to a bottom portion of the volume that includes the conical shaped center insert 464 and a constant slope portion in the height ranges corresponding to a top portion of the volume that does not include the conical shaped center insert 464.

In examples, the container portion 102 includes a capacitive sensor 112, though it is understood that other types of sensors, such as resistive, magnetic, optical (visible light based, infrared light based, laser based, machine vision based), mechanical (such as weight based, pressure based, float based), radio-wave (such as radar based), acoustic (such ultrasound or infrasound) and capacitive ladder sensors can also be used. In examples, the capacitive sensor 112 (or other sensor or sensing device) is configured to measure at least one of: (1) a flow rate of the urine, other liquid, or other substance into the container portion 102; (2) a level of the urine, other liquid, or other substance within the container portion 102; and (3) a volume of the urine, other liquid, or other substance within the container portion 102. In examples, the capacitive sensor 112 is located on the exterior surface 110 of the side-wall 106. In examples, the capacitive sensor 112 includes a substrate 114 having a first capacitive plate 116 (acting as a sensor electrode facing the measurement volume inside of the container portion 102) on a first side of the substrate 114 and a second capacitive plate 118 (acting as a reference electrode to get a reference measurement outside the container portion 102) on a second side of the substrate 114 opposite the first side of the substrate 114, such that the substrate 114 is sandwiched between the first capacitive plate 116 and the second capacitive plate 118. In examples, the substrate 114 is made of a non-conductive material while each of first capacitive plate 116 and second capacitive plate 118 are made of conductive material such as aluminum, gold, copper, or an alloy of conductive materials. In examples, the conductive material is selected based on substance that will be detected. In embodiments where the conductor comes into contact with the substance, the conductor may be selected to be less reactive with the substance to be detected. In examples, the width of and/or distance between (and/or other dimensions/geometries) the substrate 114, first capacitive plate 116, and second capacitive plate 118 is selected to achieve various resolutions and gains from the capacitive sensor 112.

FIG. 5 shows an enlarged cross-sectional diagram of how the sidewall area of the container portion 102. In examples, the capacitive sensor 112 having the first capacitive plate 116 and the second capacitive plate 118 is mounted such that the first capacitive plate 116 faces the exterior surface 110 of the side-wall 106 and the second capacitive plate 118 faces away from the side-wall 106 toward the surrounding environment. This enables measurement of two capacitance measurements: (1) a first capacitance of a rising liquid level within the side-wall 106 of the container portion 102 as measured by the first capacitive plate 116 through the side-wall 106; and (2) a second capacitance of the environment (such as air) outside of the exterior surface 110 of the side-wall 106 as a reference measurement for comparative purposes with the first capacitance. In examples, electronics within the electronics portion 104 determine at least one of: (1) flow rate of the urine, other liquid, or other substance into the container portion 102; (2) a level of the urine, other liquid, or other substance within the container portion 102; and (3) a volume of the urine, other liquid, or other substance within the container portion 102.

In examples, the first capacitive plate 116 of the capacitive sensor 112 is affixed to the exterior surface 110 of the side-wall 106 by an adhesive, epoxy, or mechanical fastening mechanism. In other examples, the first capacitive plate 116 of the capacitive sensor 112 is affixed to an insulating layer by an adhesive, epoxy, or mechanical fastening mechanism, the insulating layer affixed to the exterior surface 110 of the side-wall 106 by an adhesive, epoxy, or mechanical fastening mechanism. In examples, the capacitive sensor 112 performs best and provides better resolution when placed against a relatively flat surface. In examples, the exterior of the container portion 102 where the capacitive sensor 112 is placed is flat on the exterior. By positioning the capacitive sensor 112 on a flat portion on the exterior surface 110 of the side-wall 106, potential air pockets/gaps between the capacitive sensor 112 and the exterior surface 110 of the side-wall 106 are reduced/minimized, thereby enhancing the resolution of the measurements over placement on a rounded/curved exterior surface 110 of a side-wall 106.

In examples, the quality of the readings from the capacitive sensor 112 depends on the thickness of the side-wall 106 upon which the capacitive sensor 112 is placed. Thicker walls produces lower resolution to reading the fluid level. Thinner walls increase the reading resolution and accuracy. In examples, the wall thickness (WT) of the flat surface of the side-wall 106 of the container portion 102 where the capacitive sensor 112 is placed is between approximately zero centimeters (approximately zero inches) and approximately 1.27 centimeters (approximately ½ inch).

In examples, to avoid thickening the side-wall 106 to create the flat surface, exterior surface 110 of the side-wall 106 includes a channel 120 recessed into the exterior surface 110 of the side-wall 106, where the capacitive sensor 112 is positioned within the channel 120. In examples, the channel 120 assists in positioning, mitigates potential gaps between the capacitive sensor and the exterior surface 110 of the side-wall 106, and improves signal strength of the capacitive measurement of the fluid on the other side of the side-wall 106 because the side-wall 106 material is thinner in the channel 120 than in other areas and the first capacitive plate 116 can more easily sense inside the container portion 102. In examples, the channel 120 assists with the repeatable placement of the capacitive sensor 112 on the exterior surface 110 of the side-wall 106 both laterally and vertically on the exterior cup's surface. In examples, the channel on the exterior surface 110 of the side-wall 106 is between approximately 0 millimeters (approximately 0 inches) and approximately 25.4 millimeters (approximately 1 inch) wide.

In examples, shielding is positioned inside and/or outside of the side-wall 106 of the container portion 102 to protect the capacitive sensor 112 (or other sensor or sensing element) against false readings and/or noise in the signals caused by disturbances inside and/or outside of the side-wall 106 of the container portion 102. In examples, the container portion 102 includes at least one interior shield 122 positioned within the container portion 102 that acts as a mechanical buffer between the urine, other fluid, and/or other substance entering the container portion 102 and the capacitive sensor 112 (or other sensor or sensing element). In examples, the at least one interior shield 122 protects the capacitive sensor 112 (or other sensor or sensing element) from erroneously capturing the falling fluid as it flows into the container portion 102 and serves to dampen motion artifacts from producing tilt and/or tremor fluid volume error. In examples, the at least one interior shield 122 partitions a sensing portion 124 of the container portion 102 off from a non-sensing portion 126 of the container portion 102. In examples, the at least one interior shield 122 blocks the capacitive sensor 112 (or other sensor or sensing element) from sensing what is happening in the non-sensing portion 126 directly.

In examples, the sensing portion 124 is coupled to the non-sensing portion through at least one gap/channel/void/aperture 128 below, around the side, and/or through the at least one interior shield 122. The at least one gap/channel/void/aperture 128 allows a controlled flow of the urine, other liquid, or other substance from the non-sensing portion 126 into the sensing portion 124. By only allowing a controlled flow of the urine, other liquid, or other substance into the sensing portion 124, disturbances, turbulence, and/or slosh in the urine, other liquid, or other substance within the non-sensing portion 126 are reduced within the sensing portion 124. These disturbances, turbulence, and/or slosh can be caused as the urine, other liquid, or other substance enters the non-sensing portion 126 caused by shaking or other movement of the container portion 102 (which could be caused by a hand tremor). As the urine, other fluid, and/or other substance enters the container portion 102, it first enters the non-sensing portion 126 and a portion of the urine, other fluid, and/or other substance enters the sensing portion 124 in a controlled manner through the at least one gap/channel/void/aperture 128. Accordingly, the at least one interior shield 122 acts as a "low-pass" filter for the flow data by protecting the capacitive sensor 112 (or other sensor or sensing element) from the disturbances, turbulence, and slosh of the urine, other fluid, and/or other substance within the non-sensing portion 124.

In examples, the at least one interior shield 122 also is conductive and provides a grounding plane for the capacitance to move to from the first capacitive plate 116 of the first capacitive sensor 112 and through the urine, other fluid, and/or other substance in the sensing portion 124. In examples, the grounding plane provided by the at least one interior shield 122 prevents the electrical field lines originating from the first capacitive plate 116 (the sensor electrode) from passing past the at least one interior shield 122. In examples, the urine, other fluid, and/or other substance within the container portion 102 is electrically connected with the grounding plane provided by the interior shield 122. In examples, the grounding plane created by the at least one interior shield 122 enables flow rate measurements, reduces noise in the signals, and/or enhances the performance and/or quality of the flow and/or volume measurements.

In examples, the capacitive sensor 112 operates on the principle of differential capacitance to measure the height of the urine, other fluid, and/or other substance within the sensing portion 124. In examples, this is done by taking measurements from the first capacitive plate 116 and the second capacitive plate 118 and subtracting them from each other to obtain a differential measurement. In examples, the first capacitive plate 116 is a sensor electrode and is used to measure the height of the urine, other liquid, and/or other substance within the sensing portion 124 of the container portion 102. In contrast, the second capacitive plate 118 is a reference electrode and is used to measure the ambient conditions of a surrounding environment 132. The difference in the measurements take from the first capacitive plate 116 and the second capacitive plate 118 is calculated to generate the differential capacitance measurement. The differential capacitance measurement takes into account environmental factors and reduces the dielectric effects on the desired signal.

In exemplary embodiment, the container portion 102 includes at least one exterior shield 130 positioned outside the container portion 102 and shielding the capacitive sensor 112 from effects in an external environment 132, such as a hand coming near or touching the capacitive sensor 112 and distorting the electrical field (such as by increasing the capacitance) or another type of potential interference from the external environment 132. In examples, at least one exterior shield 130 also is conductive and provides a grounding plane for the electric field lines to move from the second capacitive plate 118 of the first capacitive sensor 112 and through an air gap and to the at least one exterior shield. In examples, the grounding plane provided by the at least one exterior shield 130 prevents the electrical field lines originating from the second capacitive plate 118 (the reference electrode) from passing past the at least one exterior shield 130. In examples, the at least one exterior shield 130 completely covers the capacitive sensor 112 from the environment outside of the container portion 102. In examples the at least one interior shield 122 and the at least one exterior shield 130 are a single piece of material that covers over the top of the edge of the side-wall 106 and the sensing portion 124 of the container portion 102.

While only a single capacitive sensor 112 (or other sensor or sensing element) is described above, in other examples, such as the embodiment described below with reference to FIG. 6, more than one capacitive sensor 112 (or other sensor or sensing element) is included. In examples, the additional capacitive sensors 112 can also be shielded internally by interior shields and externally by exterior shields. In examples, having additional sensors helps with tilt independence to mitigate measurement errors causes by tilting of the container portion 102. Tilt independence can also be achieved through use of a gimbaled handle (see FIG. 9 below) and/or by including inertial sensors (such as accelerometers, gyroscopes, etc.) in the electronics portion 104 and using data from the inertial sensors to compensate for tilt.

In examples, the container portion 102 is disposable and can be used only once or a few times before being disposed of. In other embodiments, the container portion is reusable many times. In examples, the electronics portion 104 is not disposable and is intended to be reused multiple times. In examples, the electronics portion 104 connects to the container portion 102 in different ways, such as at the top of the container portion 102 and/or on the side of the container portion 102. In examples, the electronics portion 104 is built into a handle on the container portion 102.

In examples, the electronics portion 104 is divided into a top portion 138 and a bottom portion 140 that can be separated to access the electronics inside of the electronics portion 104. In exemplary embodiment, the top portion 138 is screwed onto the bottom portion 140 using complimentary threading present on the top portion 138 and the bottom portion 140. In examples, the electronics portion 104 includes a top surface 142 that serves as the bottom surface of the container portion 102 when the container portion does not include a bottom wall. In examples, the at least one coupling element 136 (such as threads, bayonet mounts, friction fit, tabs, clips, and/or fasteners) is complimentary to the at least one coupling element 134. In examples, the at least one coupling element 136 and the at least one coupling element 134 engage after rotating the container portion 102 onto the electronics portion 104. In examples, when the at least one coupling element 136 engages with the at least one coupling element 134, a liquid tight seal is created between the top surface 142 and the bottom of the container portion 102.

In examples, the electronics portion 104 includes electrical contacts 144 that connect with corresponding electrical contacts 146 electrically connected to the capacitive sensor 112 of the container portion 102 when the at least one coupling element 136 engages with the at least one coupling element 134. In examples, the electronics portion 104 includes at least one alignment indicator 148 configured to aid in alignment of the at least one coupling element 136 with the at least one coupling element 134 when connecting the electronics portion 104 to the container portion 102. In examples, the at least one alignment indicator 148 is a visual and/or tactile alignment indicator. In examples, a corresponding alignment indicator is also present on the container portion 102. In examples, the at least one alignment indicator 148 includes coloring and the container portion 102 includes corresponding coloring.

In examples, the electronics portion 104 includes at least one button 150 and/or at least one electronic indicator 152. In examples, the button can be pressed by the user to indicate the beginning and/or end of a voiding event during which measurement occurs. For example, the user could press the at least one button 150 before urinating into the container portion 102. The push of the at least one button 150 at this time can trigger a new voiding event file to be created by the electronics components within the electronics portion 104 and/or for a counter/timer marker to be placed into a file by the electronics components within the electronics portion 104. In examples, the user could press the at least one button 150 after completion of the voiding event once urination is completed. The push of the at least one button 150 at this time can trigger a counter/timer market to be placed into the file by the electronics components within the electronics portion 104, for writing to the file to be terminated, and/or for the file to be closed. In examples, writing to the file can be terminated and/or the file closed by the electronics components within the electronics portion 104 after the flow rate is below a certain threshold for a certain amount of seconds.

In examples, during and after a voiding event, any significant movement may add an indeterminate error to the voiding volume. Certain conditions and/or patient age may exacerbate this "shaking" which may add an indeterminate error. It would be advantageous for the user to convey to the device that their voiding event is actually over. This could assist in minimizing the hand-held "shaking" error that can potentially skew results. Additionally, placing the device on a level surface after the void to allow the device to take a "final" measurement of the actual void in a non-hand-held configuration could be used to "adjust" the final measured volume captured. In examples, the ability for the user to communicate to the device that a voiding event is over (a button push, voice command, etc.). Consider doing a post void, "final" calibration on a level surface prior to shut down.

In examples, the electronics portion 104 can be activated in other ways rather than pressing a button or switch, such as by: (1) sensing the presence of urine, other fluid, and/or other substance within the container portion 102; (2) motion detection; (3) a sensor configured to detect when someone is holding the device; and/or (4) detection of when the electronics portion 104 is coupled with a container portion 102.

In examples, the at least one electronic indicator 152 includes at least one of a visual, audible, and haptic alert. For example, at least one of a visual, audible, and haptic alert can occur when: (1) the container portion 102 is properly connected with the electronics portion 104 once the at least one coupling element 136 and the at least one coupling element 134 are properly engaged; (2) the urine measurement device 100 and/or electronics portion 104 are functioning properly (such as to confirm operation after the urine measurement device 100 and/or electronics portion 104 were dropped); and (3) that the urine measurement device 100 is fully function (battery level is adequate, container portion 102 is operating correctly, electronics portion 104 is operating correctly, electrical contact between the container portion 102 and the electronics portion 104 is acceptable, humidity and/or temperature is within operation range.

In exemplary embodiment, the at least one electronic indicator 152 is used to indicate when the at least one button 150 has been pressed and/or when the measurement is in progress or completed. In examples, the electronics portion 104 provides spoken instructions and/or status updates to the user, such as indications that the "device is fully functional" or requests for the user to "insert a sleeve". In examples, audible beeps indicate operation and/or status updates to the user. In examples, the electronics portion 104 includes a more complex human machine interface (HMI) for user interaction with the urine measurement device 100. In examples, the HMI includes any combination of input and/or display devices, including for example light emitting diode (LED) indicators, Liquid Crystal Display (LCD) displays, e-ink displays, and/or touch screens, buttons, switches, dials, cameras, etc. In examples, haptic alerts include vibration.

In examples, the urine measurements are taken by the urine measurement device 100 within a preferred operating environment where the operational relative humidity (RH) range between approximately zero and approximately eighty percent relative humidity and within the operational temperature range between approximately 10 degrees Celsius (approximately 50 degrees Fahrenheit) and approximately 38 degrees Celsius (approximately 100 degrees Fahrenheit). In examples, the urine measurement device 100 further includes temperature and/or humidity compensation circuitry including temperature and/or humidity sensors included within the container portion 102 and/or the electronics portion 104.

In examples, the urine measurement device 100 is calibrated soon before taking measurements to account for current environmental conditions, such as the relative humidity (RH) and/or the temperature. In examples, to establish environmental conditions at the time of measurement, the user "teaches" (calibrates) the capacitive sensor 112 as to what capacitance values are present at 0 percent urine, other fluid, and/or other substance height, equating that capacitance to the lowest possible output voltage of the sensor, and what capacitance values are present at 100 percent urine, other fluid, and/or other substance height, equating that capacitance to the highest possible output voltage of the sensor. This calibration/zeroing/taring step effectively normalizes variances in temperature and humidity just prior to taking actual urine, other fluid, and/or another substance height data.

In examples, manual calibration is performed prior to use according to the following steps: (1) the user turns on the device with no urine, other fluid, and/or another substance in the container portion 102, automatically teaching the sensor at a zero percent urine, other fluid, and/or another substance height; (2) the user then fills the container portion with water, past a specified level indicated on the container portion; (3) the user then pushes a calibration button, teaching the sensor a 100 percent urine, other fluid, and/or another substance height. After the urine measurement device 100 has been calibrated in the current environment, the user can then empty out the container portion 102 and use the urine measurement device 100 to record their voiding event In examples, calibration is performed prior to use according to the following: (1) a piece of conductive material is adhered to the inside of the container portion 102, opposite to where the capacitive sensor 112 is adhered to the container portion 102 (this is likely done at manufacture of the container portion 102); (2) the conductive material is then grounded to simulate a high urine, other fluid, and/or other substance height within the container portion (this is likely done at manufacture of the container portion 102); (3) when the container portion 102 is installed onto the electronics portion 104, the sensor is taught a 100 percent urine, other fluid, and/or another substance height because of the grounded piece of conductive material adhered to the inside of the container portion 102; (4) indicator 140 then indicates to the user that the user should remove the conductive material using a pull-tab from the inside of the sleeve (this could occur via an LED flash and/or other indication); (5) after either a certain period of time or a button press from the user confirming that the conductive material has been removed, the capacitive sensor 112 is taught at zero percent urine, other fluid, and/or other substance height. After the urine measurement device 100 has been calibrated in the current environment, the user can then use the urine measurement device 100 to record their voiding event.

Figure 6:
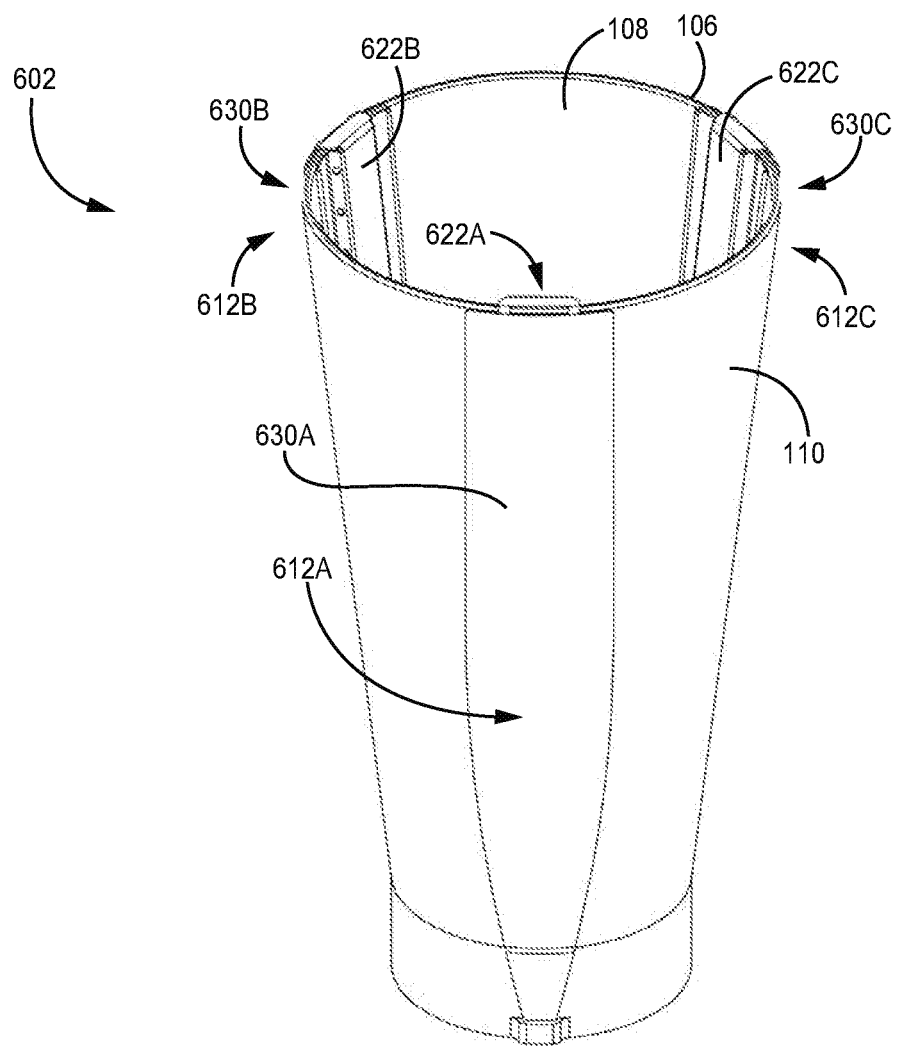
FIG. 6 is a top perspective view of another exemplary embodiment of the container portion of the urine measurement device of FIG. 1A having a plurality of sensors.

FIG. 6 is a perspective view of another exemplary embodiment of the container portion 102 of the urine measurement device 100 that includes a plurality of sensors, hereinafter container portion 602. Container portion 602 includes three separate capacitive sensors 112, hereinafter capacitive sensors 612A, 612B, and 612C. Container portion also includes three separate interior shields 122, hereinafter interior shield 622A, 622B, and 622C. Container portion also includes three separate exterior shields 130, hereinafter exterior shields 630A, 630B, and 630C. Container portion 602 and its component parts operate similarly to the description of container portion 102 above, just that there are signals from each of the capacitive sensors 612A, 612B, and 612C that are sent to the electronics portion 104 for processing and determination of at least one of the flow rate of the substance into the container portion 602, the height of the substance within the container portion 602, and the volume of the substance within the container portion 602. In examples having three capacitive sensors 612A, 612B, and 612C, each of the three capacitive sensors 612A, 612B, and 612C is located approximately 120 degrees from each of the other capacitive sensors 612A, 612B, and 612C. In examples having only two capacitive sensors 612A and 612C, each of the two capacitive sensors 612A and 612B is located approximately 180 degrees from the other capacitive sensor 612A and 612B. By combining the data from the three different capacitive sensors 612A, 612B, and 612C, the urine measurement device 100 using the container portion 602 allows for tilt independence. Specifically, as the container is tilted to one side, while it may not be measured as much by one of the capacitive sensors 612A, 612B, and 612C, it will be measured more by one or more of the other capacitive sensors 612A, 612B, and 612C.

Figure 7:
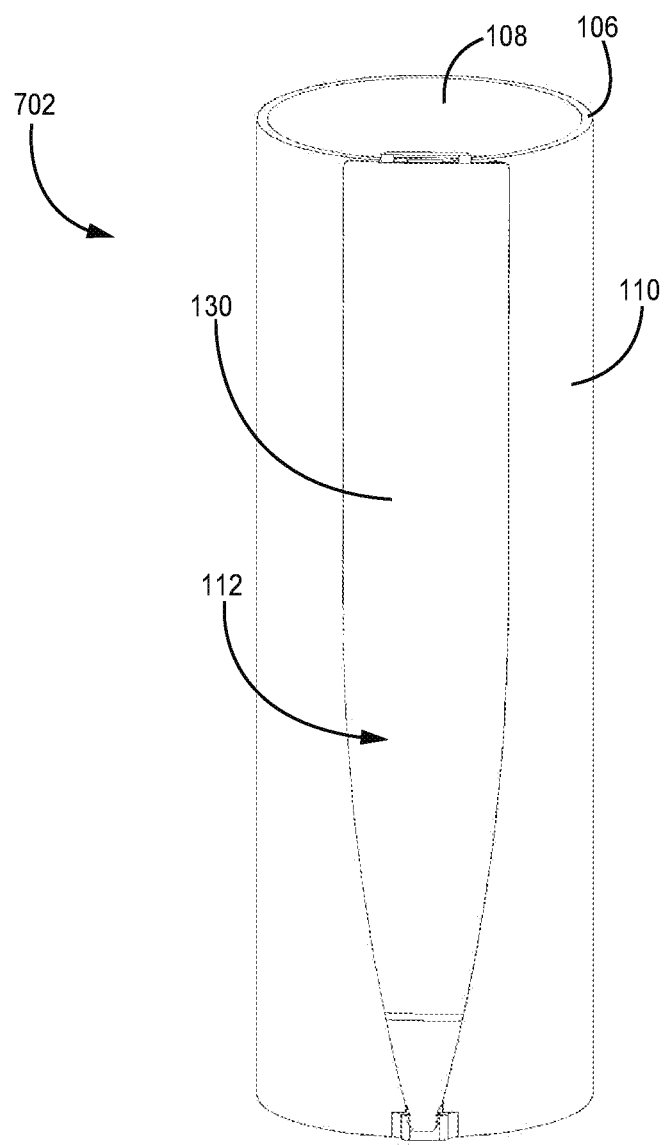
FIG. 7 is a top perspective view of another exemplary embodiment of the container portion of the urine measurement device of FIG. 1A having straight non-tapered sides.

FIG. 7 is a perspective view of another exemplary embodiment of the container portion 102 of the urine measurement device 100 having a straight non-tapered sidewall 106, hereinafter container portion 702.

Figure 8A:
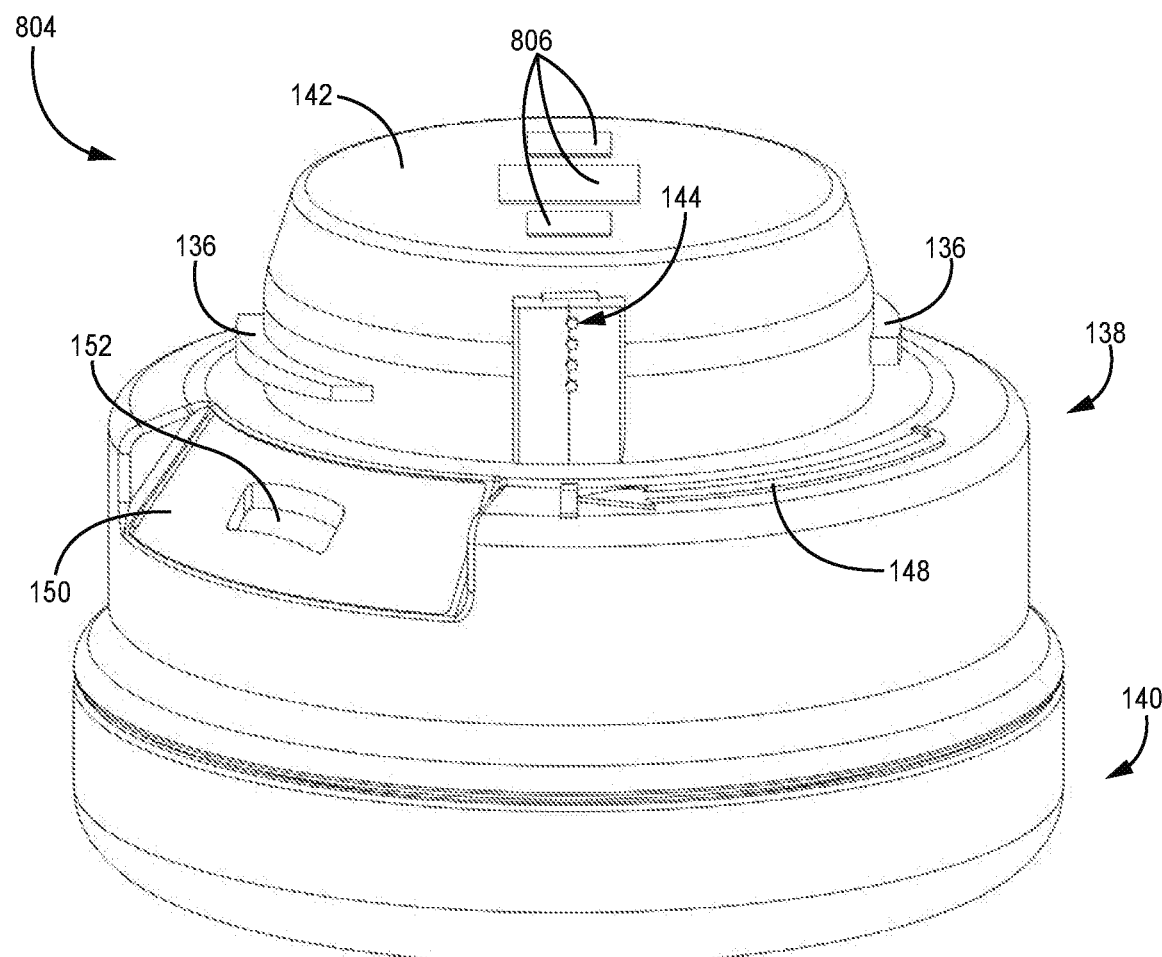
FIG. 8A is a top perspective view of another exemplary embodiment of the electronics portion of the urine measurement device of FIG. 1A having sensors on a top surface of the electronics portion.
Figure 8B:
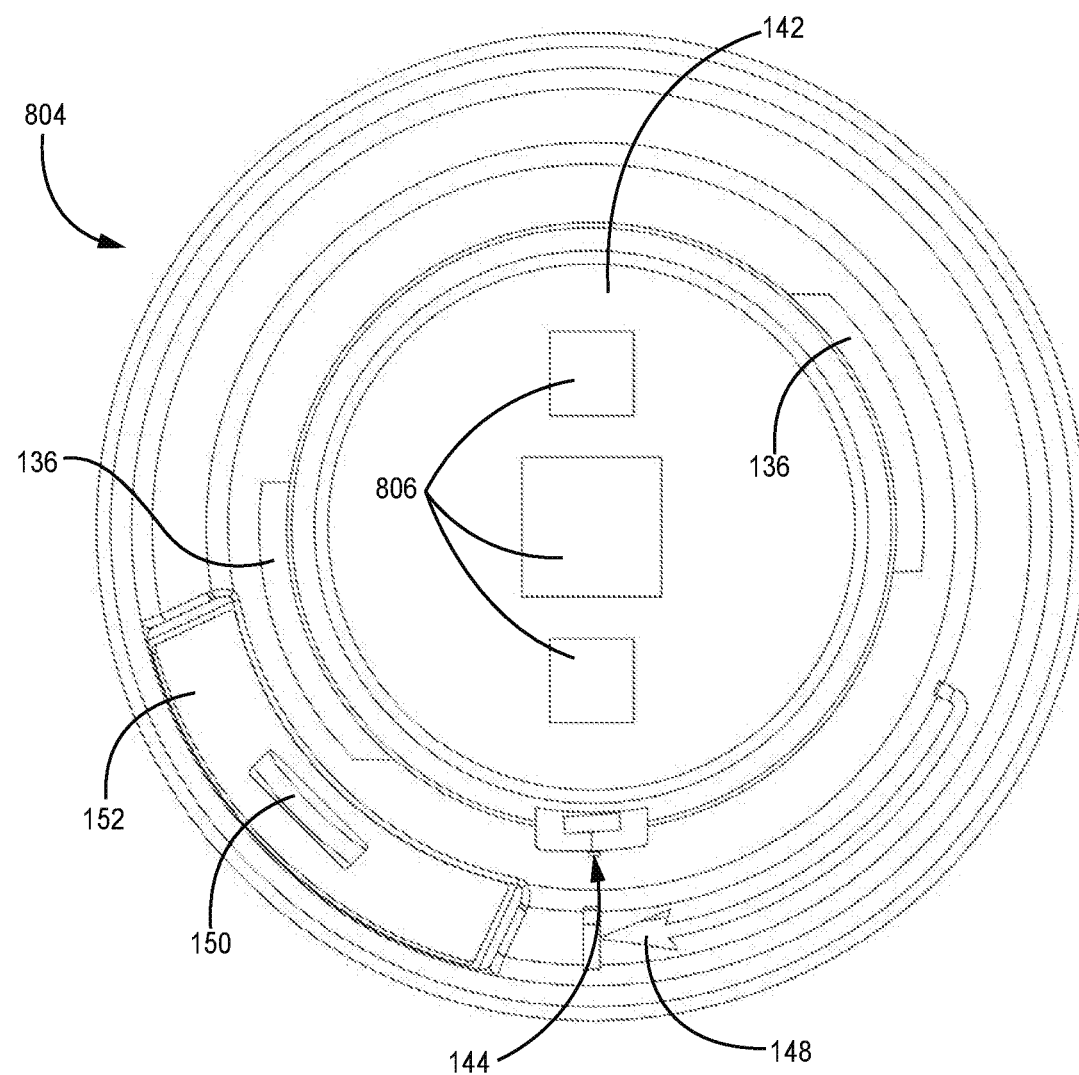
FIG. 8B is a top view of the exemplary embodiment of the electronics portion of FIG. 8A.

FIGS. 8A-8B show different views of another exemplary embodiment of the electronics portion 104 of the urine measurement device 100 having at least one sensor 806 on the top surface 142, referred to herein as electronics portion 804. FIG. 8A is a perspective view of the electronics portion 804 and FIG. 8B is a top view of the electronics portion 804. In examples, each of the at least one sensor 806 are particular sensors designed to sense various properties of the urine, other liquid, or other substance deposited into the container portion 102. In examples, the at least one sensor 806 senses proteins, dissolved solids, sugar levels, gravity, etc. of the urine, other liquid, or other substance deposited into the container portion 102. In examples, one of the at least one sensor 806 determines total dissolved solids (permittivity) in the urine, other liquid, or other substance. In examples, the capacitive sensor 112 and the at least one sensor 806 measuring TDS are not operational at the same time as they may affect each other's readings when they are turned on at the same time. Accordingly, the TDS sensor can be off while the capacitive sensor 112 is on and the capacitive sensor 112 can be off while the TDS sensor is on at synchronized times. In other embodiments, the at least one interior shield 122 isolates the sensors operation enough that the TDS sensor can operate in the non-sensing portion 126 while the capacitive sensor 112 operates in the sensing portion 126 without substantial interference between the two.

Figure 9:
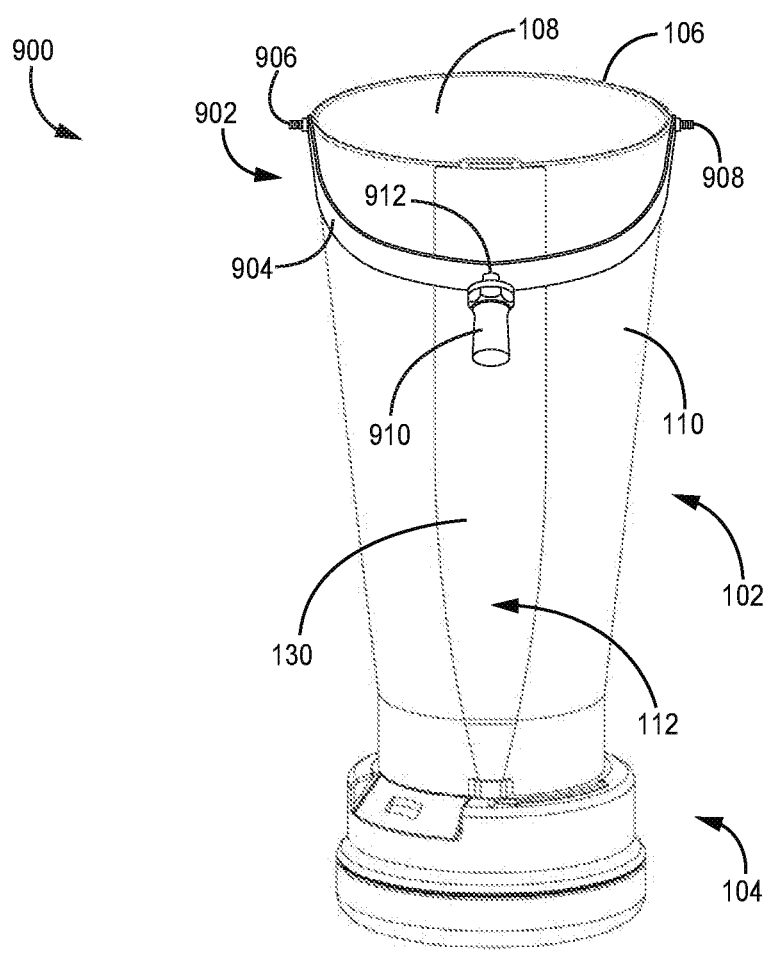
FIG. 9 is a top perspective view of another exemplary embodiment of a urine measurement device, including a container portion, an electronics portion, and a stabilizing handle portion.

FIG. 9 is a perspective view of another exemplary embodiment of a urine measurement device 900, including a container portion 102, an electronics portion 104, and a stabilizing handle portion 902. Urine measurement device 900 includes similar components to urine measurement device 100 described above, which operate as described above. In addition, urine measurement device 900 includes the stabilizing handle portion 902 that aids in leveling the container portion 102 during uroflowmetry even if the user is holding it at an angle or shaking during the measurement. In examples, the stabilizing handle portion 902 includes a connecting bracket 904 connected to the container portion 102 using a first rotating connector 906 and a second rotating connector 908. In examples, the first rotating connector 906 and the second rotating connector 908 enable the connecting bracket 904 to pivot along an axis between the first rotating connector 906 and the second rotating connector 908. In exemplar embodiments, the stabilizing handle portion 902 further includes a handle 910 connected to the connecting bracket 904 using a third rotating connector 912. In examples, the third rotating connector 912 enables the handle 910 to pivot along another axis.

In examples, gravity aids in leveling the container portion 102, based on the weight of the electronics portion 104 and the urine, other liquid, or other substance as it enters the container portion 102. In examples, the stabilizing handle portion 902 enables the container portion 102 to be horizontal to the ground independent of how the handle 910 is positioned by the user. In examples, the ability to pivot around the two axes enables the stabilizing handle portion 902, when held by a user at the handle 910 to suppress undesired tilting of the container portion 102 facilitating more accurate measurement of the flow rate; urine, other fluid, and/or other substance level; and/or urine, other fluid, and/or other substance volume in the container portion 102. While container portion 102 is described with reference to FIG. 9 above, it is understood that any suitable container portion can be used with the stabilizing handle portion 902, such as the other container portions described herein. While the stabilizing handle portion 902 was described with a specific structure herein, it is understood that other types of gimballed stabilizing means and/or swivel balls and/or other mechanical stabilization generally can be used to achieve the desired mechanical tilt independence. Further, while the stabilizing handle portion 902 (and mechanical stabilization for tilt independence generally) is described above as compensating a single capacitive sensor 112 based system, it is understood that the mechanical stabilization described herein can be used to compensate for tilt and/or user shake in systems having more sensors (such as additional capacitive sensors 112) and/or other types of sensors, such as optical (visible light based, infrared light based, laser based, machine vision based), mechanical (such as weight based and pressure based), acoustic (such as ultrasound and/or infrasound), and radio-wave (such as radar based) sensors can also be used to determine at least one of flow rate; urine, other fluid, and/or other substance height; and/or urine, other fluid, and/or other substance volume. In examples, just one of flow rate; urine, other fluid, and/or other substance height; and/or urine, other fluid, and/or another substance volume are determined and the others are determined based on knowledge of additional parameters, such as the geometry of the container portion 102 and the elapsed time.

Figure 10A:
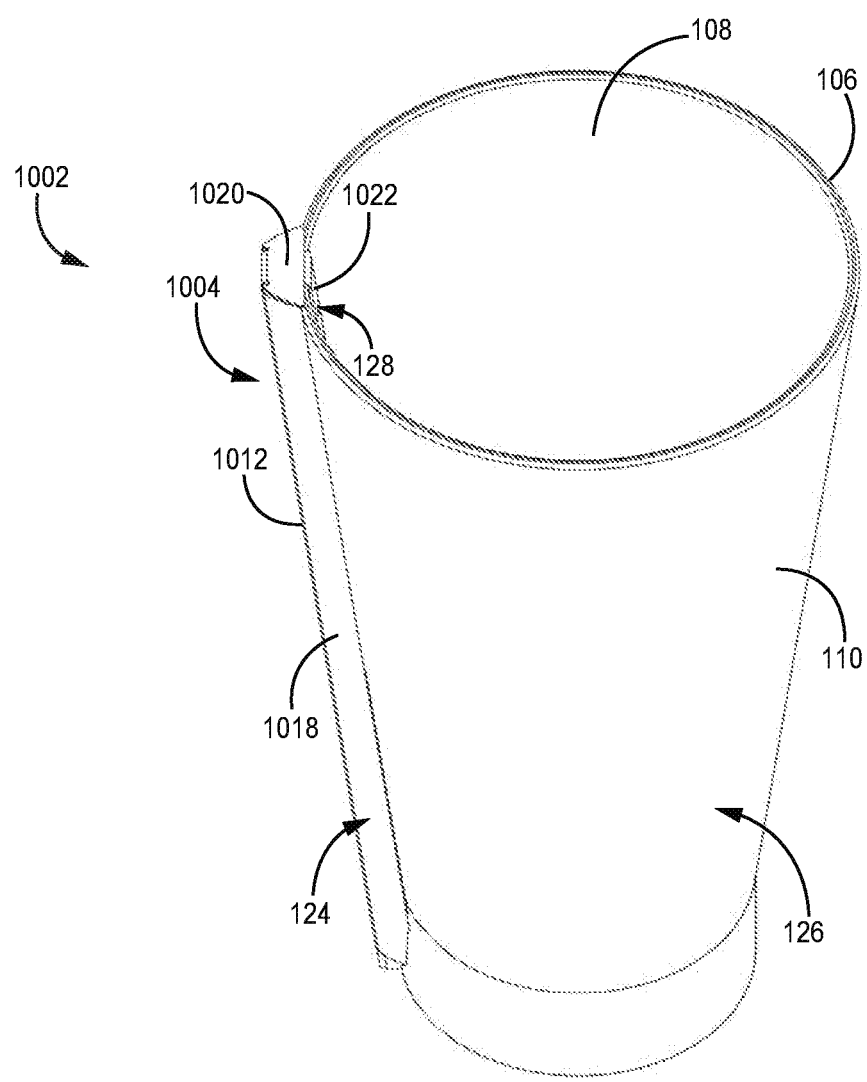
FIG. 10A is a top perspective view of another exemplary embodiment of the container portion of the urine measurement device of FIG. 1A having an outer notched portion.
Figure 10B:
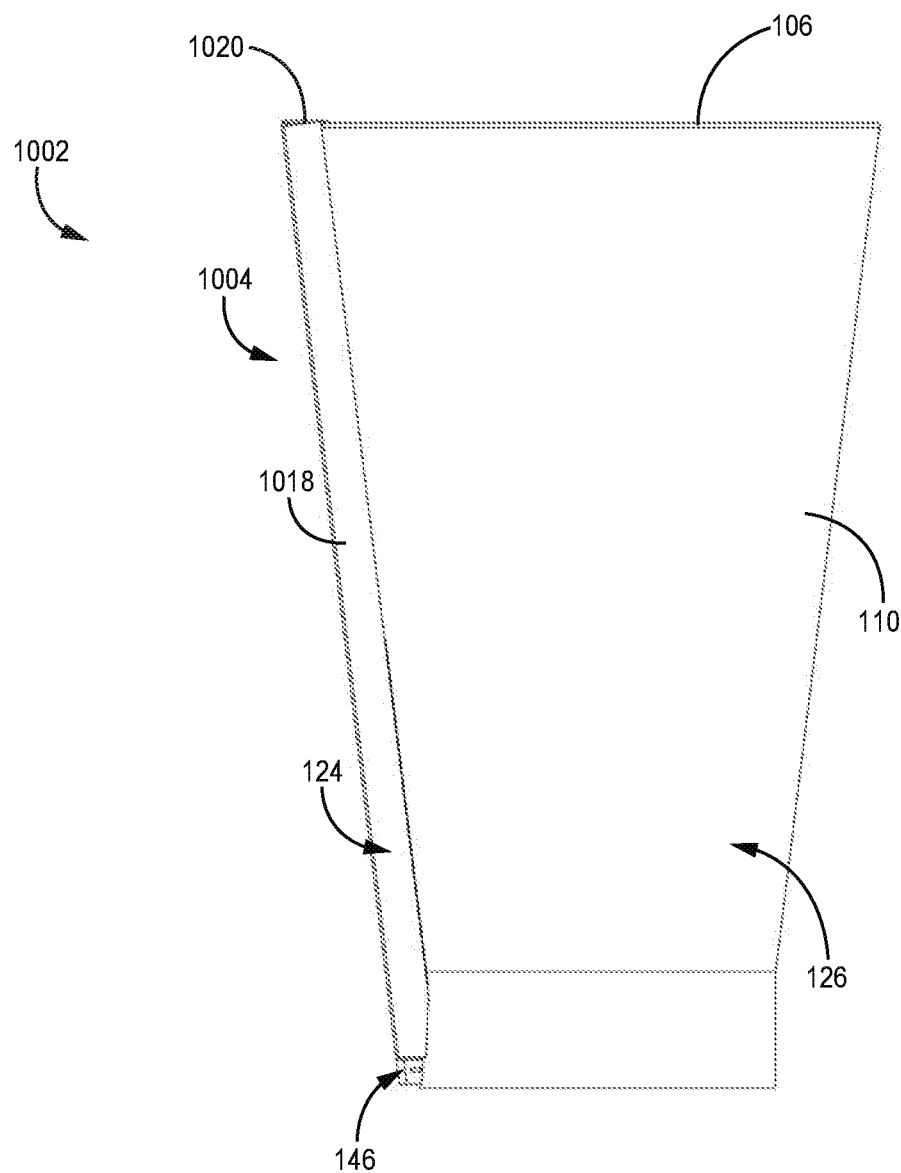
FIG. 10B is a side view of an example of the container portion of FIG. 10A.
Figure 10C:
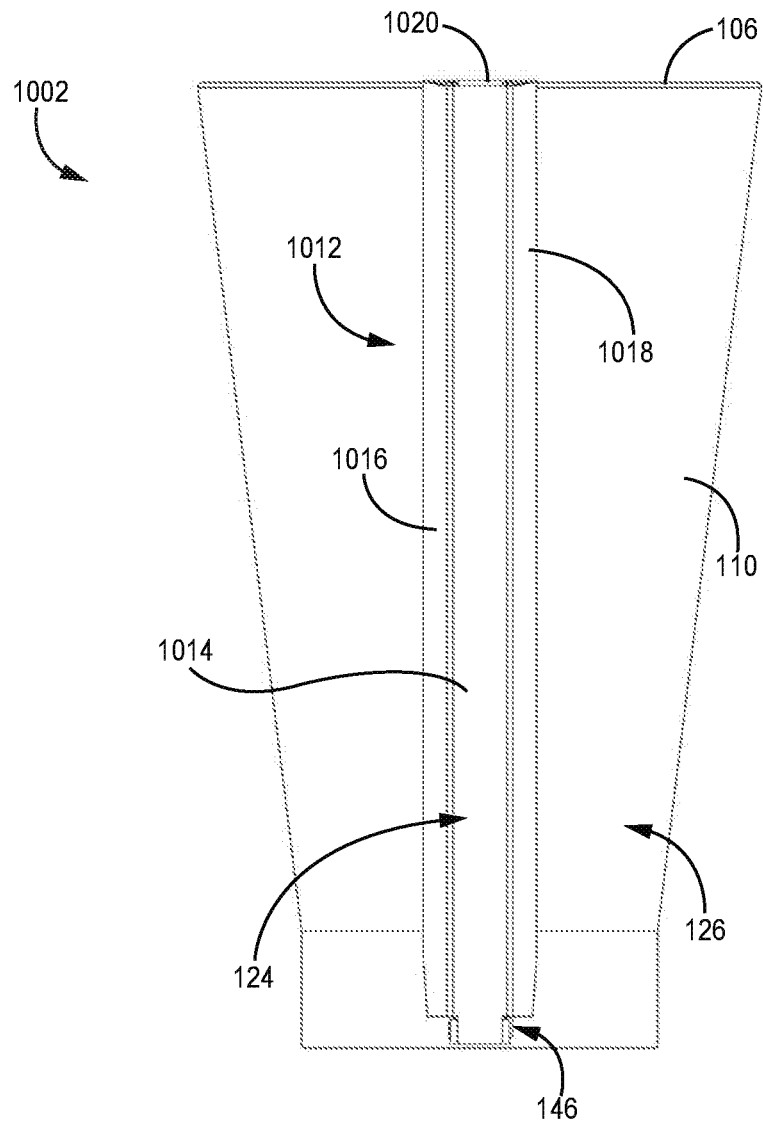
FIG. 10C is another side view of the exemplary embodiment of the container portion of FIG. 10A.
Figure 10D:
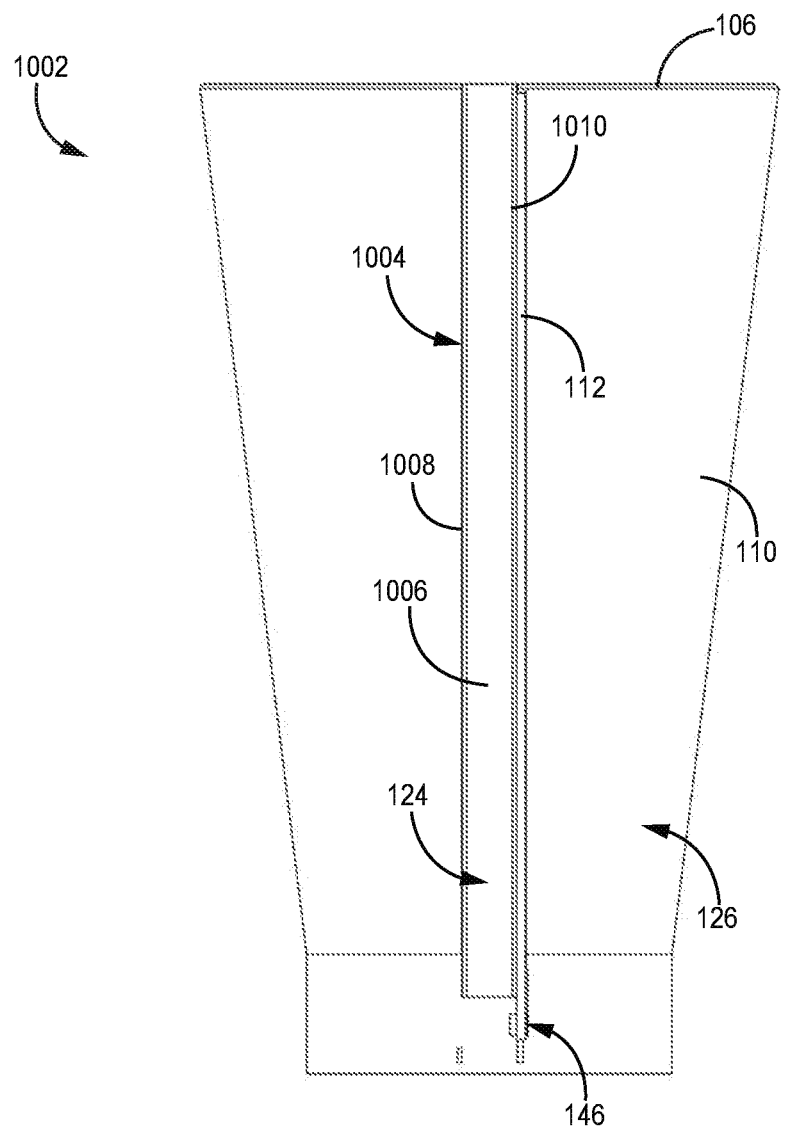
FIG. 10D is another side view of the exemplary embodiment of the container portion of FIG. 10A without the exterior shield so that the capacitive sensor, grounding plane, and voids between the outer notched portion and the main portion of the container portion can be seen.
Figure 10E:
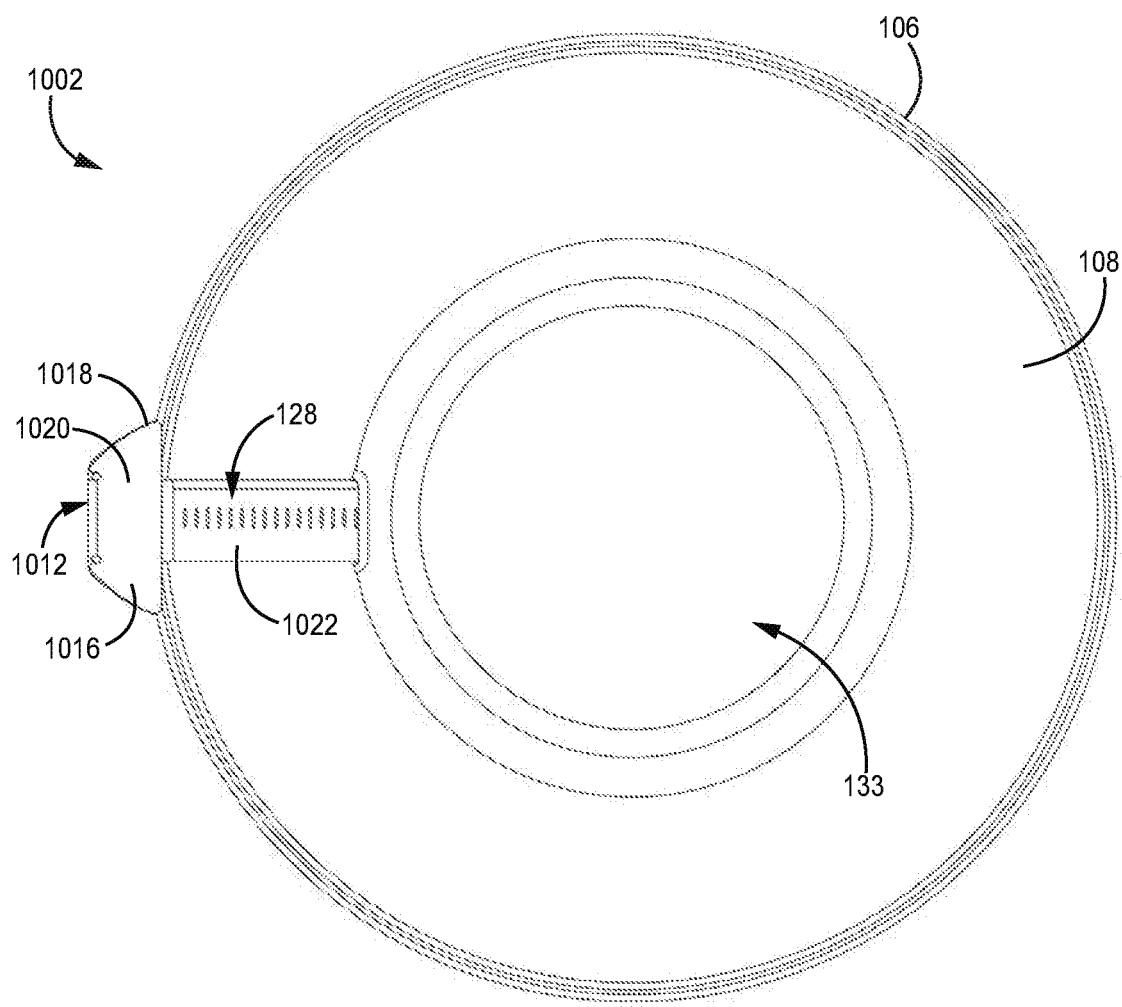
FIG. 10E is a top view of an example of the container portion of FIG. 10A.
Figure 10F:
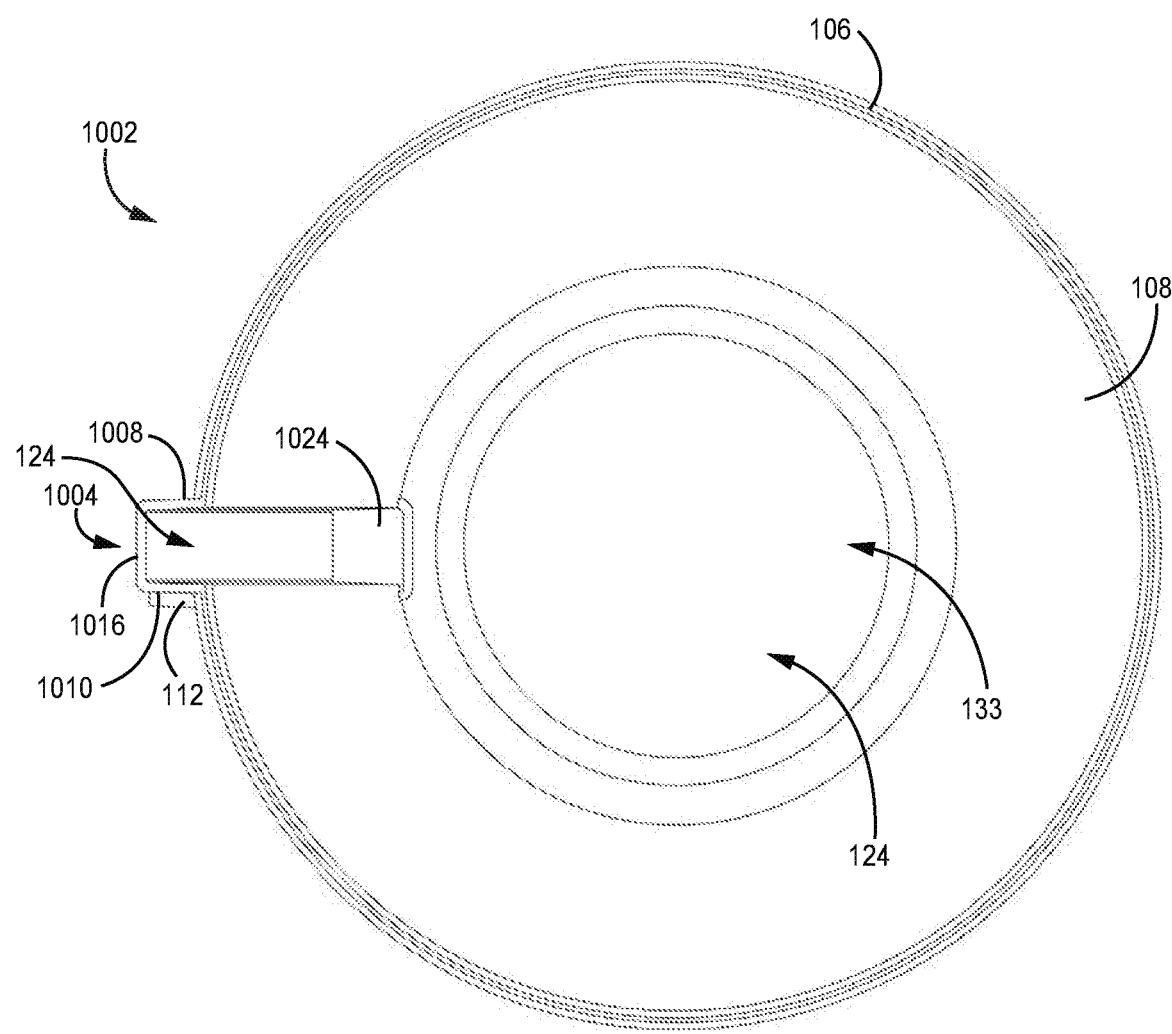
FIG. 10F is another top view of the exemplary embodiment of the container portion of FIG. 10A without the exterior shield so that the capacitive sensor, grounding plane, and voids between the outer notched portion and the main portion of the container portion can be seen.
Figure 10G:
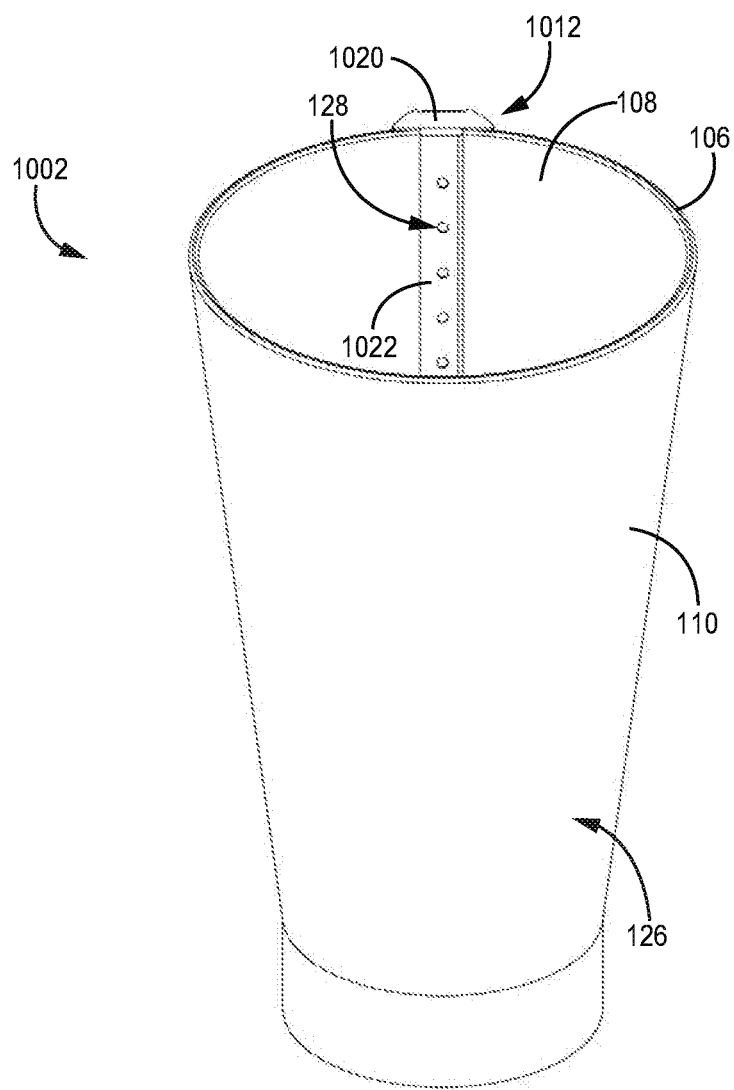
FIG. 10G is another top perspective view of the container portion of FIG. 10A.
Figure 10H:
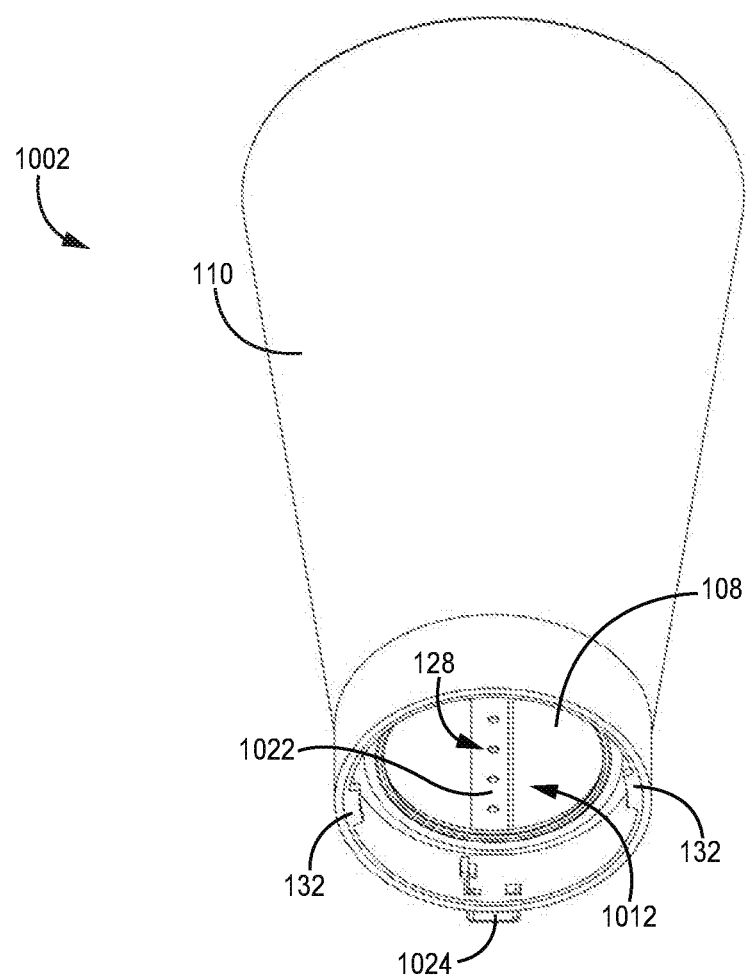
FIG. 10H is bottom perspective view of the container portion of FIG. 10A from the bottom.

FIGS. 10A-10H show different views of another exemplary embodiment of the container portion 102 of the urine measurement device 100, hereinafter container portion 1002. FIG. 10A is a top perspective view of the container portion 1002, FIG. 10B is a side view of the container portion 1002, FIG. 10C is a side view of the container portion 1002 rotated 90 degrees from FIGS. 10A and 10B, FIG. 10D is a side view of the container portion 1002 of FIG. 10C without the at least one shield 1012 such that the notch section 1004 can be seen, FIG. 10E is a top view of the container portion 1002, FIG. 10F is a bottom view of the container portion 1002, FIG. 10G is a top perspective view of the container portion 1002 rotated 90 degrees from FIG. 10A, and FIG. 10H is a bottom perspective view of the container portion 102. The description below focuses on features shown in FIGS. 10A-10H that are distinct from the features of container portion 1002 that are similar to those in container portion 102.

The primary difference between the container portion 1002 and the container portion 102 described above is that the sensing portion 126 of the container portion is contained in a notch section 1004 that protrudes from the exterior of the main body of the container portion 1002 that includes the non-sensing portion 126. In examples, gap/channel/void/ aperture 128 between the notch section 1004 and the main body of the container portion 1002 allow urine, other fluid, and/or other substance to pass from the non-sensing portion 126 where the urine, other fluid, or other substance enter into the container portion 1002 and into the sensing portion 124 in a controlled manner. As with the container portion 102, by only allowing a controlled flow of the urine, other liquid, or other substance into the sensing portion 124, disturbances, turbulence, and/or slosh in the urine, other liquid, or other substance within the non-sensing portion 126 are reduced within the sensing portion 124 of the notch section 1004 of the container portion 1002. As the urine, other fluid, or other substance enters the container portion 1002, it first enters the non-sensing portion 126 and a portion of the urine, other fluid, or other substance enters the sensing portion 124 in a controlled manner through the at least one gap/channel/void/ aperture 128. Accordingly, the notch section 1004 acts as a "low-pass" filter for the flow data by protecting the capacitive sensor 112 (or other sensor or sensing element) from the disturbances, turbulence, and slosh of the urine, other fluid, or other substance within the non-sensing portion 126.

In examples, the notch section 1004 includes a front wall 1006, a side wall 1008, and a side wall 1010. In examples, the capacitive sensor 112 (or other sensor or sensing element) is attached to the exterior of the side wall 1010. In examples, the container portion 1002 includes a shield 1012 that covers the notch section 1004 and includes a front wall 1014, a side wall 1016, a side wall 1018, a top 1020, and an interior wall 1022 between the notch section 1004 and the main body of the container portion. In examples, the interior wall 1022 includes the at least one gap/channel/void/aperture 128 between the non-sensing portion 126 and the sensing portion 124. In exemplary embodiment, the notch section includes a bottom surface 1024. As with container portion 102, some implementations of container portion 1002 include a bottom wall 133 while others do not and rely on the top surface 142 of the electronics portion 102 when it is coupled with the container portion 1002 to serve as the bottom wall of the container portion 1002. In examples, the side wall 1008 serves as the grounding plane for the at least one capacitive sensor 112 such that the capacitance measurement is taken across the sensing portion 124 in between the at least one capacitive sensor 112 and the grounding plane.

Figure 11:
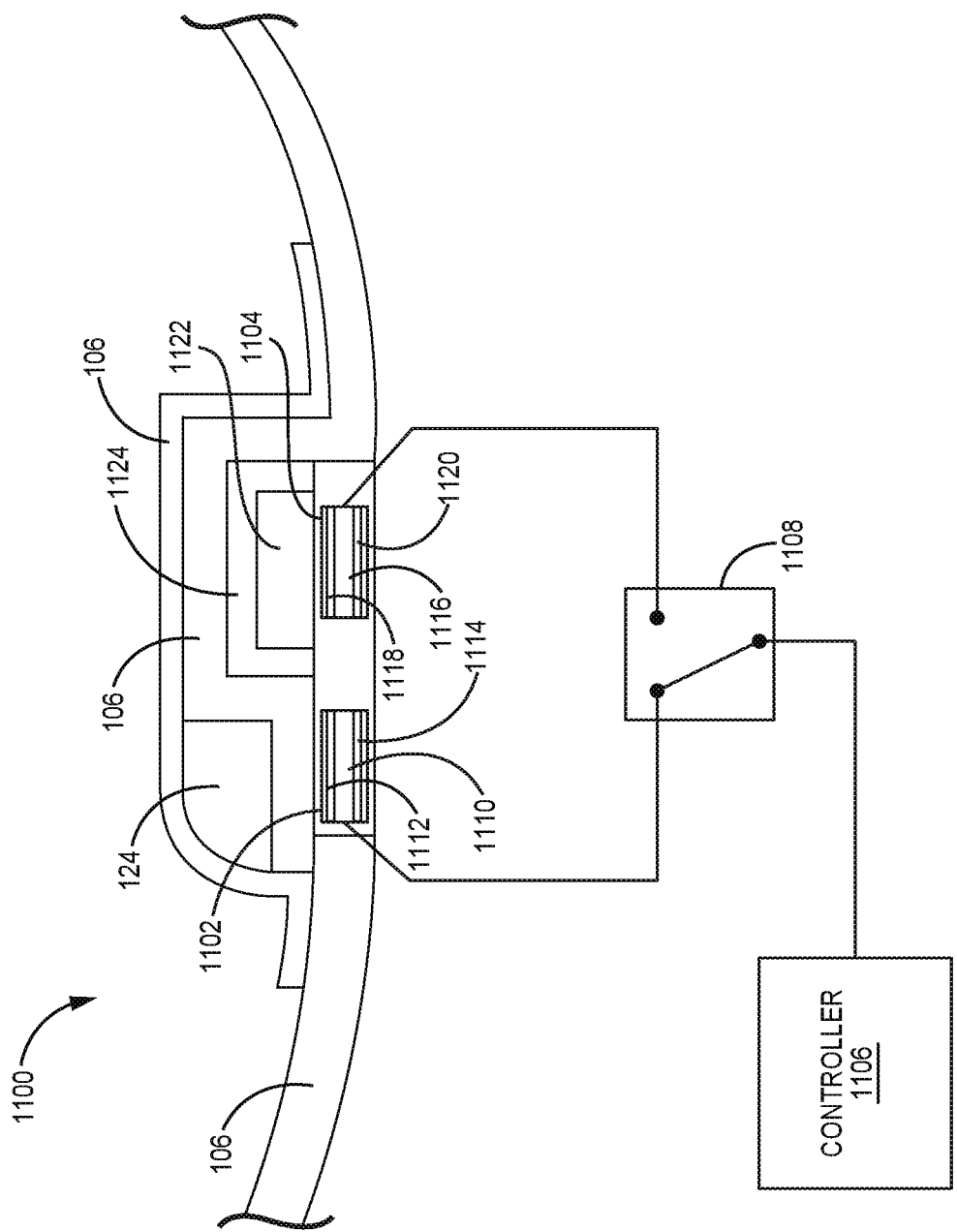
FIG. 11 is a block diagram of an example of a calibration architecture for calibrating a urine measurement device using capacitive sensors.

FIG. 11 is block diagram of an example of a calibration architecture 1100 for calibrating a urine measurement device using two capacitive sensors. This calibration architecture 1100 is an example of an architecture that makes calibration of the sensor for a current environment even simpler than the user driven calibration described above. The calibration architecture 1100 includes a primary capacitive sensor 1102, a secondary capacitive sensor 1104, a controller 1106, and a relay/multiplexer/switch 1108. In examples, both the primary capacitive sensor 1102 and the secondary capacitive sensor 1104 are embodiments of the capacitive sensor 112 described above.

Specifically, the primary capacitive sensor 1102 includes a substrate 1110 having a first capacitive plate 1112 (acting as a sensor electrode facing the measurement volume inside of the container portion 102) on a first side of the substrate 1110 and a second capacitive plate 1114 (acting as a reference electrode to get a reference measurement outside the container portion 102) on a second side of the substrate 1110 opposite the first side of the substrate 1110, such that the substrate 1110 is sandwiched between the first capacitive plate 1112 and the second capacitive plate 1114. In examples, the substrate 1110 is made of a non-conductive material while each of first capacitive plate 1112 and second capacitive plate 1114 are made of conductive material such as aluminum, gold, copper, or an alloy of conductive materials.

Similarly, the secondary capacitive sensor 1104 includes a substrate 1116 having a first capacitive plate 1118 (acting as a sensor electrode facing the measurement volume inside of the container portion 102) on a first side of the substrate 1116 and a second capacitive plate 1120 (acting as a reference electrode to get a reference measurement outside the container portion 102) on a second side of the substrate 1116 opposite the first side of the substrate 1118, such that the substrate 1116 is sandwiched between the first capacitive plate 1118 and the second capacitive plate 1120. In examples, the substrate 1116 is made of a non-conductive material while each of first capacitive plate 1118 and second capacitive plate 1118 are made of conductive material such as aluminum, gold, copper, or an alloy of conductive materials.

In exemplary embodiment, the primary capacitive sensor 1102 and the secondary capacitive sensor 1104 are substantially equivalent in their properties. In examples, the primary capacitive sensor 1102 is used to both (1) take the initial zero percent urine, other fluid, and/or other substance height calibration reading when the container portion 102 is empty; and (2) collect the flow data in real-time during a measurement. In examples, the secondary capacitive sensor 1104 is only used to take the 100 percent urine, other fluid, and/or other substance height calibration reading. The main difference between the primary capacitive sensor 1102 and the second capacitive sensor 1104 is that the secondary capacitive sensor 1104 is configured with a dielectric spacer 1122 with a conductive substrate 1124 opposite the first capacitive plate 1118 of the secondary capacitive sensor 1104. In examples, the first capacitive plate 1118 of the secondary capacitive sensor 1104 is positioned in contact with the dielectric spacer 1122 on one side of the dielectric spacer 1122 and the conductive substrate 1124 is positioned in contact with the other side of the dielectric spacer 1122 opposite the first capacitive plate 1118. In examples, the conductive substrate 1112 is substantially the same height as the secondary capacitive sensor 1104 and synthesizes the height at which the container would be 100 percent full.

In examples, the calibration architecture 1100 is integrated into or placed on the outside surface 110 of the side-wall 106 of an embodiment of the container portion 102. In examples, both all of the primary capacitive sensor 1102, the secondary capacitive sensor 1104, the dielectric spacer 1122, and the conductive substrate 1124 are outside of the side-wall 106. In examples, the sensing portion 124 is created inside of the interior shield 122. In examples, the primary capacitive sensor 1102 and the second capacitive sensor 1104 are on a single printed circuit board. In other embodiments, primary capacitive sensor 1102 and the secondary capacitive sensor 1104 are on separate printed circuit boards.

In examples, the relay/multiplexer/switch 1108 is used to allow the controller 1106 to: (1) first sample the primary capacitive sensor 1102 while the container portion 102 is empty to get the zero percent full calibration point in the current environment; (2) toggle to the secondary capacitive sensor 1104 to collect a synthesized 100 percent full calibration point based on the dielectric spacer 1122 and the conductive substrate 1124 simulating a 100 percent full calibration point in the current environment; and (3) toggles back to the primary capacitive sensor 1102, ready for the urination voiding event and calibrated to the current environment. In examples, the indicator 148 (such as an LED) indicates that the calibration event has ended and that the device is ready for measurement of a urination voiding event.

In examples, the conductive substrate 1124 is replaced with an internally contained column of water that is also grounded. The internally contained column of water is held in a water tight enclosure to give it the shape and surface area which a sheet of conductive material would have.

Figure 12:
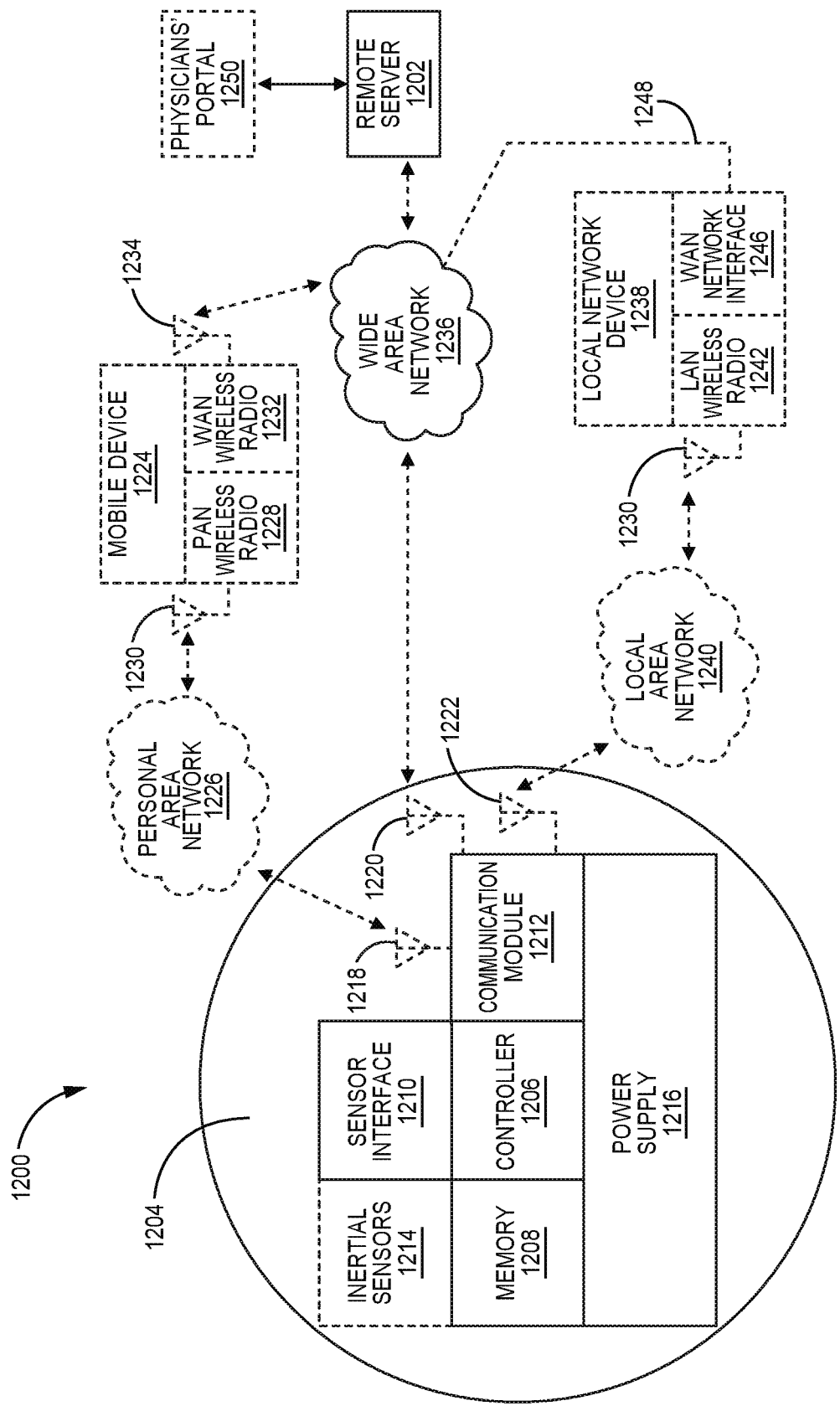
FIG. 12 is a block diagram of an exemplary system including the urine measurement device of FIG. 1A

FIG. 12 is a block diagram of an exemplary system 1200 enabling transmission of data from a urine measurement device (such as urine measurement device 100) to a remote server 1202. In examples, an electronics portion 1204 (such as electronics portion 104 or electronics portion 804) of a urine measurement device is communicatively coupled with a remote server 1202 in various ways. In examples, the electronics portion 1204 includes a controller 1206, memory 1208, at least one sensor interface 1210, at least one communication module 1212, optional inertial sensors 1214, and a power supply 1216. In examples, the power supply provides power to the controller 1206, memory 1208, the at least one sensor interface 1210, the at least one communication module 1212, and the optional inertial sensors 1214.

In examples, the controller 1206 implements at least some of the processing described herein. In examples, the controller 1206 is a programmable processor, such as a microcontroller, an application-specific integrated circuit (ASIC), a field-programmable gate array (FPGA), a field-programmable object array (FPOA), or a programmable logic device (PLD). The controller 1206 described above may include or function with software programs, firmware or other computer readable instructions for carrying out various methods, process tasks, calculations, and control functions, described herein. These instructions are typically stored on any appropriate computer readable medium used for storage of computer readable instructions or data structures. The computer readable medium can be implemented as any available media that can be accessed by a general purpose or special purpose computer or processor, or any programmable logic device. Suitable processor-readable media may include storage or memory media such as magnetic or optical media. For example, storage or memory media may include conventional hard disks, Compact Disk-Read Only Memory (CD-ROM), volatile or non-volatile media such as Random Access Memory (RAM) (including, but not limited to, Synchronous Dynamic Random Access Memory (SDRAM), Double Data Rate (DDR) RAM, RAMBUS Dynamic RAM (RDRAM), Static RAM (SRAM), etc.), Read Only Memory (ROM), Electrically Erasable Programmable ROM (EEPROM), and flash memory, etc. Suitable processor-readable media may also include transmission media such as electrical, electromagnetic, or digital signals, conveyed via a communication medium such as a network and/or a wireless link.

In examples, the at least one sensor interface 1210 is configured to interface with the capacitive sensor 112 (or other sensor or sensing device) of the container portion and any additional at least one sensor 806 present in the urine measurement device. In examples, the controller 1206 is configured to measure or calculate at least one of flow rate; urine, other fluid, and/or other substance height and volume based on the signals received at the at least one sensor interface 1210 from the at least one capacitive sensor 112. In examples, the raw voltage value read from the sensors; the calculated flow rate; urine, other fluid, and/or other substance height and/or volume is saved in the memory 1208 or on another storage device. In examples, the raw voltage value read from the sensors, the calculated flow rate and/or urine, other fluid, and/or other substance height and/or volume is associated with a counter and/or time. In examples, the raw voltage value read from the sensors, the calculated flow rate and/or urine, other fluid, and/or another substance height and/or volume is transmitted to an external device using the at least one communication module 1212. In examples, the at least one communication module 1212 includes at least one processor as described herein, at least one radio, and/or at least one wired network interface. In other examples, the controller 1206 is configured to take measurements of voltage that correspond to a capacitance from the capacitive sensor 112 through the at least one sensor interface 1210 and to save the measurement in the memory 1208 or on another storage device. In examples, the capacitance measurements are associated with a counter and/or time. In examples, the capacitance measurements or raw voltage values are transmitted to an external device using the at least one communication module 1212. In examples data collected form the additional at least one sensor 806 is stored in the memory 1208 or another storage device and/or transmitted to an external device using the at least one communication module 1212.

In examples, the optional inertial sensors 1214 are configured to provide inertial measurement data to the controller 1206 that is used to compensate for any tilt of the container portion 102 during measurement of the flow rate and/or urine, other fluid, and/or other substance height and/or volume. In examples, the optional inertial sensors include at least one accelerometer and/or at least one gyroscopes configured to measure tilt in particular directions and/or rotation around particular axes. In examples, the controller 1206 compensates the data for any tilt and/or vertical perturbations detected by the optional inertial sensors 1214 (such as an accelerometers detecting vertical error and/or gyroscopes detecting rotation/tilt) which could lead to false volumetric measurement if not mitigated. In other embodiments, the data from the inertial sensors is included with the data regarding the flow rate and/or urine, other fluid, and/or other substance height and/or volume that is provided to an external device for processing, such as the mobile device 1224, local network device 1238, and/or remote server 1202 described herein and the external device performs the compensation of the data for any tilt and/or vertical perturbations detected by the optional inertial sensors 1214 (such as an accelerometers detecting vertical error and/or gyroscopes detecting rotation/tilt) which could lead to false volumetric measurement if not mitigated. In examples, the data from the optional inertial sensors is used to compensate tilt in combination with a plurality of capacitive sensors 112 (such as capacitive sensors 612A, 612B, and 612C of FIG. 6 described above) and/or the stabilizing handle portion 902 of FIG. 9 described above.

In examples, data provided by the optional inertial sensors 1214 is used to validate that the bottom of the container portion 102 is parallel to the ground, but is not used to actually compensate for the container portion 102 not being parallel to the ground. Instead, in examples when the data from the optional inertial sensors 1214 indicates that the bottom of the container portion 102 is not parallel to the ground, an alert is provided to the user (such as through the indicator 148), so that the user can attempt to correct the issue. In examples, a visual and audible alarm can be used to alert the user that the device is out of horizontal level. The alarm could be related to other conditions of interest, low battery, excessive swirl (vibration), mal-alignment of the container component (sleeve), too much motion, sensor calibration issues, and/or sensor malfunction. In examples, the tilt indication comes through a visual indicator (such as tilt indicator light), an audible indicator (such as tilt indicator sound), and a haptic indicator (such as vibration). In addition, in examples when the data from the optional inertial sensor 1214 indicates that the bottom of the container portion 102 is not parallel to the ground, a flag can be included in the measurement file to indicate that the device was not level during operation. In examples, the status of the operating conditions of interest are stored in data file either locally or remotely.

FIG. 12 shows three distinct data paths from the electronics portion 1204 to the remote server 1202, though additional paths are possible. In examples, the at least one communication module 1212 includes a separate antenna for each data path, such as antenna 1218, antenna 1220, and antenna 1222. In examples, the at least one communication module 1212 communicates data to a mobile device 1224 through a personal area network 1226, such as a Bluetooth connection. In examples, the mobile device 1224 includes a personal area network (PAN) wireless radio 1228 having an antenna 1230 and a wide area network (WAN) radio 1232 having an antenna 1234. In examples, at least one communication module 1212 of the electronics portion 1204 communicates signals via the antenna 1218 across the personal area network 1226 to the PAN wireless radio 1228 of the mobile device 1224 via the antenna 1230. In examples, the mobile device 1224 includes a processor that performs processing of the data received from the electronics portion 1204. In examples, the mobile device 1224 communicates data across a wide area network 1236 to the remote server using WAN wireless radio 1232 via antenna 1234.

In examples, the at least one communication module 1212 communicates data to the remote server 1202 across the wide area network 1236 using antenna 1220. In examples, the at least one communication module 1212 includes a cellular data modem and the wide area network 1236 is implemented at least in part using a cellular data communication network.

In examples, the at least one communication module 1212 communicates data to a local network device 1238 across the local area network 1240, such as a WiFi network, using antenna 1222. In examples, the local network device 1238 includes a local area network (LAN) wireless radio 1242 having an antenna 1244 and a wide area network (WAN) network interface 1246 communicatively coupled to the wide area network 1236 by a communication link 1248. In examples, the at least one communication module 1212 of the electronics portion 1204 communicates signals via the antenna 1218 across the local area network 1240 to the LAN wireless radio 1242 via the antenna 1244. In examples, the local network device 1238 includes a processor that performs processing of the data received form the electronics portion 1204. In examples, the local network device 1238 communicates data across a wide area network 1236 via the communication link 1248 to the remote server 1202.

In examples, the communication link 1248 is at least in part across a wired communication medium. In other examples, the communication link 1248 is at least in part across a wireless communication medium. While wireless and/or wired communication elements are described herein, it is understood that other embodiments may include different types of communication in different areas of the system 1200.

In examples, the electronics within the electronics portion 1204, and specifically the controller 1206, can be updated through over-the-air (OTA) firmware and/or software updates. In examples, the data collected at the remote server 1202 can be accessed remotely by physicians, other health providers, and others using a physicians' portal 1250. In examples, at least one of the controller 1206, the mobile device 1124, the local network device 1238, the remote server 1202, the physicians' portal 1250, and/or another device generates a voiding diary and/or other reports which can track various properties of urine over time including but not limited to volume, flow rate, glucose, blood, bacteria, color, odor, turbidity, specific gravity, pH, protein, ketones, urobilinogen, bilirubin, nitrites, leukocytes and creatinine.

In examples, data is captured and stored in on-board memory (SD card) and can be retrieved wirelessly, wired, or physically removing the storage device. In examples, data is sent to smart device (Android or iOS and stored) and then sent from the smart device to web-based database. In examples, data is sent to a web-based database via on-board cell module. In examples, the data transmitted includes at least one of date and time of events, device identification (ID), device health status, environmental conditions, environmental factors, sleeve identification (ID), calibration coefficients, etc. In examples, the data can be transmitted wirelessly or wired from the puck to a transmitting device, then from the transmitting device either wirelessly or wired to the Internet, such as a web portal or other server. In examples, the data can be transmitted in a data file including at least some data embedded in a header, footer, or any other location.

In examples, printed circuit board (PCB) sensors include additional features that facilitate field calibration either prior to data collection or concurrently during data acquisition. Capacitive sensors are susceptible to variations in sensor manufacturing and environmental factors. Additional sensors or a pre-test calibration can be used to digitally eliminate variables that can affect the accuracy and precision of capacitance based sensor readings, such as manufacturing variability as well as temperature, humidity, and other environmental variables.

In examples, a simple capacitor can be constructed using two conducting plates or conductive materials of surface area A that are a distance d apart according to the relationship:

$$C = \frac{\epsilon_r \epsilon_o A}{d}$$

where:
  C=capacitance
  $\epsilon_r$=relative permittivity (dielectric between the plates)
  $\epsilon_o$=permittivity constant (free space)
  A=area of conductive plates
  d=distance between the conductive plates Among other things, capacitance is a function of the area. If the area of a capacitor is suddenly increased, there will be a measurable and simultaneous increase in the capacitance reading. A series of abrupt increases in the area of grounded capacitive plates can result in a step function increase in the capacitive area as the substance height rises within a container. The stepped increases in the capacitive area result in a step function increase in the measurable capacitance. A secondary capacitive sensor can use detection plates at known heights or volumes with a container to create an increasing capacitive plate design that yields a trigger point identifier at known substance heights or substance volumes within the container. The secondary capacitive sensor with the detection plates can be used to calibrate a capacitance based substance height derived from a first capacitive sensor every time the substance is measured by the sensor.

If it is desired to achieve an exacting capacitance range between two plates, precise areas, distances and the relative permittivity between the plates must be maintained. Such exacting tolerances can be achieved using PCB multilayer board designs. The use of PCB manufactured boards and processes for exacting tolerances to create very specific surface areas and distances between plates in multi-layer board configurations for capacitive sensors designed for and relating to uroflowmetry, such as shown in FIG. 2C (capacitive sensor 112 made using PCB multilayer board design).

Capacitance systems can be sensitive to changing environmental factors including manufacturing variability. Stray capacitance and any manufacturing variability can add error into measurements. Consequently, calibrating a capacitance based system (such as a flow meter) prior to, during, or after measurement collection assures the best accuracy and reproducibility in data acquisition and data quality. Typical calibration procedures for capacitance based fluid level measuring systems include a measure of the capacitance just prior to data collection (empty) and then a second measurement of a known volume or fluid height (say, full). This procedure typically accounts for most systemic errors, changes in manufacturability, changes in sensor variability, environmental temperature and humidity, as well as any environmental stray capacitance. An auto calibration feature would be desirable. This feature would automatically calibrate the sensor for environmental conditions (temperature, humidity, etc.) and any manufacturing variability of the sensor and/or container portion prior to, during, or after data acquisition.

The charge relationship is:

$$Q = \sqrt{k_b T C}$$

Where:
  Q=Charge
  $k_b$=Boltzman's Constant
  T=Temperature
  C=Capacitance

In examples, one or more calibration techniques are implemented to increase the accuracy and reliability of a capacitance based uroflometer. A first option is to include a second calibration sensor (or use the primary sensor, see FIG. 5, first capacitive plate 116 and second capacitive plate 118, see also FIG. 11) that mimics a full container and measures calibration coefficients necessary to compensate for temperature, humidity and any other environmental ambient capacitive noise. A second option is to include mid-range, known capacitive sensor lengths at known volumes that can verify the quality of the calibration coefficients at the "full" condition. A third option is to include stop gaps or trigger points at known capacitive sensor lengths at precise volumes (50.0 ml, 100.0 ml, etc) to refine the actual measured capacitance at those volumes. These stop gaps or trigger points can be used as error correction for measured values.

Figure 13A:
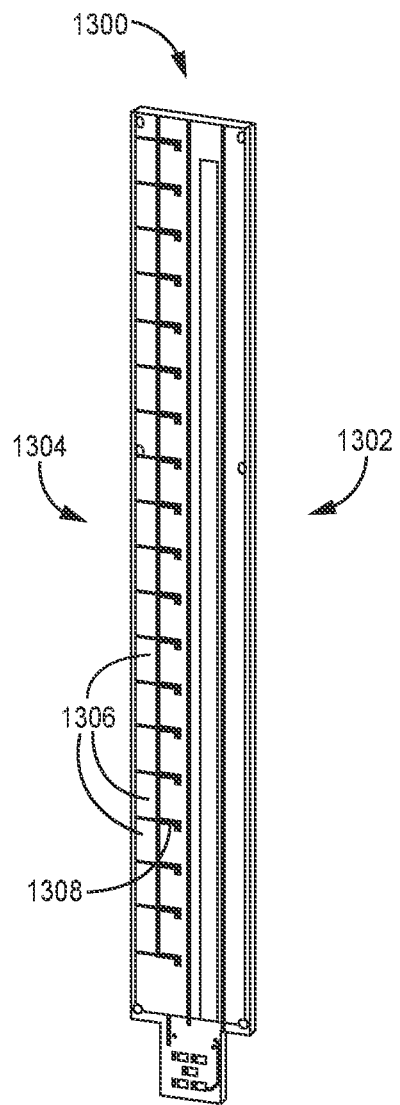
FIG. 13A is a perspective view of an example of a sensing device having a primary capacitive sensor and a secondary capacitive sensor.
Figure 13B:
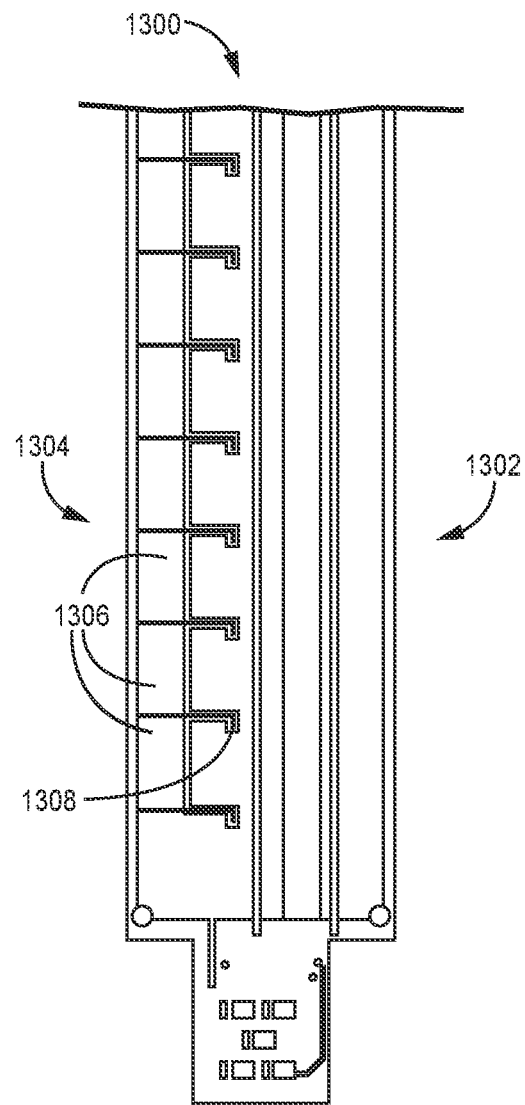
FIG. 13B is a side view of a portion of the example sensing device having the primary capacitive sensor and the secondary capacitive sensor of FIG. 13A.

FIG. 13A is a perspective view of an example of a sensing device 1300 having a primary capacitive sensor 1302 and a secondary capacitive sensor 1304 that can be used in place of capacitive sensor 112 in the examples described above or in other systems having any combination of the features of the systems described above, such as systems without any electrical and/or mechanical shielding (such as interior shield 122 and exterior shield 130). FIG. 13B is a side view of a portion of the example sensing device 1300 having the primary capacitive sensor 1302 and the secondary capacitive sensor 1304. In examples, the primary capacitive sensor 1302 is used to collect capacitance data that changes as a substance enters the container portion 102 of the urine measurement device 100 (or other fluid or substance measurement device). In examples, the sensing device 1300 (including the primary capacitive sensor 1302 and the secondary capacitive sensor 1304) is located on the interior surface 108 of the side-wall 106 of the container portion 102. In examples, the surface of the primary capacitive sensor 1302 is covered in a tape (such as Kapton, Teflon, and/or polytetrafluoroethylene (PTFE) film tapes), film, spray, or otherwise suitably prepared to minimize any residual fluid left on the surface of the primary capacitive sensor 1302 between voiding events so that stray fluid does not skew the capacitance measurements. In examples, the tape, film, spray, or other preparation causes fluid to bead up and roll off and then evaporate.

In examples, the primary capacitive sensor 1302 collects capacitance data from an analog signal to get a continuous measurement of the changing capacitance at various times as described above with reference to capacitive sensor 112. In examples, the primary capacitive sensor 1302 is configured to measure at least one of: (1) a flow rate of the urine, other liquid, or other substance into the container portion 102; (2) a level of the urine, other liquid, or other substance within the container portion 102; and (3) a volume of the urine, other liquid, or other substance within the container portion 102. In examples, the primary capacitive sensor 1302 is constructed similar to the capacitive sensor 112 above and includes a substrate 114 having a first capacitive plate 116 (acting as a sensor electrode facing the measurement volume inside of the container portion 102) on a first side of the substrate 114 and a second capacitive plate 118 (acting as a reference electrode to get a reference measurement outside the container portion 102) on a second side of the substrate 114 opposite the first side of the substrate 114, such that the substrate 114 is sandwiched between the first capacitive plate 116 and the second capacitive plate 118. In examples, the substrate 114 is made of a non-conductive material while each of first capacitive plate 116 and second capacitive plate 118 are made of conductive material such as aluminum, gold, copper, or an alloy of conductive materials. In examples, the conductive material is selected based on substance that will be detected. In embodiments where the conductor comes into contact with the substance, the conductor may be selected to be less reactive with the substance to be detected. In examples, the width of and/or distance between (and/or other dimensions/geometries) the substrate 114, first capacitive plate 116, and second capacitive plate 118 is selected to achieve various resolutions and gains from the primary capacitive sensor 1302. The changing capacitance detected by the primary capacitive sensor 1302 is related to the changing substance height within the container portion 102 as a function of time. Flow rate can be determined by taking the first order derivative of the changing substance height. Automatic calibrating of the data from the primary capacitive sensor 1302 is based on data from the secondary capacitive sensor 1304.

The secondary capacitive sensor 1304 includes a plurality of grounded capacitive plates 1306 having trigger points 1308 at a plurality of corresponding known heights within the container portion 102. In examples, each of the plurality of grounded capacitive plates 1306 includes exposed conductive metal/material which connects to a rectangle of copper on the secondary capacitive sensor 1304. In examples, the substance is conductive (such as urine or other conductive fluid) and is connected to ground at the bottom of the sensor so that when the substance touches one of the grounded capacitive plates 1306 at the trigger point 1308, the entire rectangle of the grounded capacitive plate 1306 is connected to ground, resulting in a step change in the capacitance reading of the secondary capacitive sensor 1304. In examples, each trigger point 1308 of the grounded capacitive plate 1306 is placed lower than the rectangle of copper of the grounded capacitive plate 1306 to which the trigger point 1308 is connected so that as the fluid rises, the grounded plane of copper prevents the secondary capacitive sensor 1304 from changing capacitance as it is "blinded" to the fluid height change until the next trigger point 1308. In examples, the trigger point 1308 of each grounded capacitive plate 1306 is at a known height and the sensor is in the container portion 102 of known geometry such that each grounded capacitive plate 1306 at the trigger point 1308 is indicative of a known precise corresponding volume. Accordingly, the secondary capacitive sensor 1304 outputs a step (digital like) signal that is reordered in order to obtain the relationship between fluid height and the capacitance of the primary capacitive sensor 1302 at each known volume corresponding to each grounded capacitive plate 1306 at the trigger point 1308. In examples, the signal from the secondary capacitive sensor 1304 has a dramatic step change in capacitance only when the fluid connects to a grounded capacitive plate 1306 at the trigger point 1308.

In examples, the primary capacitive sensor 1302 and the secondary capacitive sensor 1304 are simultaneously sampled. In examples, the primary capacitive sensor 1302 and the secondary capacitive sensor 1304 are alternately sampled so that each sample on one sensor has a corresponding sample on the other sensor with minimal time difference between the two samples. Alternately sampling the primary capacitive sensor 1302 and the secondary capacitive sensor 1304 allows for calibration of the primary sensor data from the primary capacitive sensor 1302 at each time point that a grounded capacitive plate 1306 at the trigger point 1308 is connected to ground by the substance at the trigger point 1308. Since each trigger point 1308 of the grounded capacitive plate 1306 has an associated volume within the container portion 102, a calibration from the primary capacitive sensor 1302 value to the volume of the container portion 102 can be created, enabling live calibration for each event of substance entering the container portion 102 to mitigate manufacturing differences in the primary capacitive sensor 1302, secondary capacitive sensor 1304, container portion 102, electronics portion 104, or other component of the urine measurement device 100 or any changes in the external environment conditions (such as temperature, humidity, pressure, etc.).

Figure 13C:
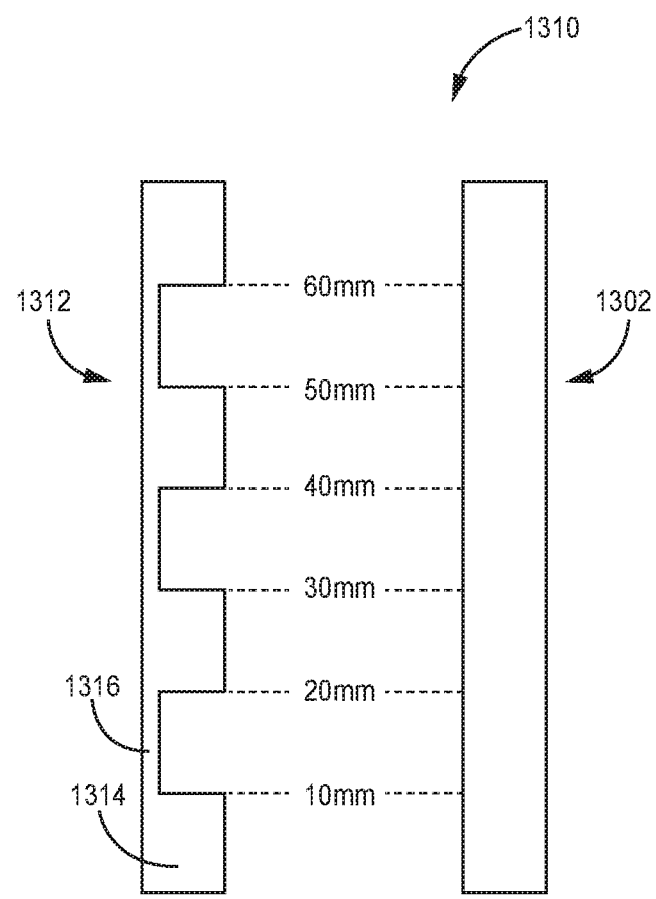
FIG. 13C is a side view of an example of a sensing device suitable for placement on the outside of a container having a primary capacitive sensor and a secondary capacitive sensor.

FIG. 13C is a side view of an example of a sensing device 1310 suitable for placement on the outside of a container and having a primary capacitive sensor 1302 and a secondary capacitive sensor 1312. In examples, primary capacitive sensor 1302 and secondary capacitive sensor 1312 of sensing device 1310 may be constructed onto the same PCB substrate, similar to primary capacitive sensor 1302 and secondary capacitive sensor 1304 of sensing device 1300, or be two distinct sensors. Sensing device 1310 (shown in FIG. 13C) differs from sensing device 1300 (shown in FIGS. 13A-13B) in that the sensing device 1300 is generally configured to be placed on the inside of the container in contact with the substance. In examples, there is a physical discontinuity between the capacitive plates and the grounded substance within the container can bridge the discontinuities increasing the overall capacitance surface area. In examples, the increasing capacitance plates are additive with the sensor plates in the sensor 1300. In contrast, the sensing device 1310 of FIG. 13C is a single capacitive plate design with two components: a primary capacitive sensor 1302 and a secondary capacitive sensor 1312, where the secondary capacitive sensor 1312 is continuous but has sharp increases or decreases in the capacitive surface areas at known heights. These sharp increases or decreases in the capacitive surface area at known heights constitute trigger points in the sensing device 1310. Specifically, the secondary capacitive sensor 1312 includes a number of wider area portions 1314 of the secondary capacitive sensor 1312 and a number of narrower area portions 1316 of the secondary capacitive sensor 1312. The transition points between the wider area portions 1314 and the narrow area portions 1316 constitute trigger points. This configuration results in noticeably increased capacitance (such as at the wider area portions 1314) or noticeably decreased capacitance (such as at the narrower area portions 1316) at known heights representative of known volumes and associated with a capacitance or voltage reading collected on the primary sensor 1302 for that known, given height or volume. In examples, this sensor complex can be placed on the outside of the container, does not need a conductive substance within the container, and can have non-zero slopes of increasing capacitance or voltage with increasing fluid height.

Figure 14A:
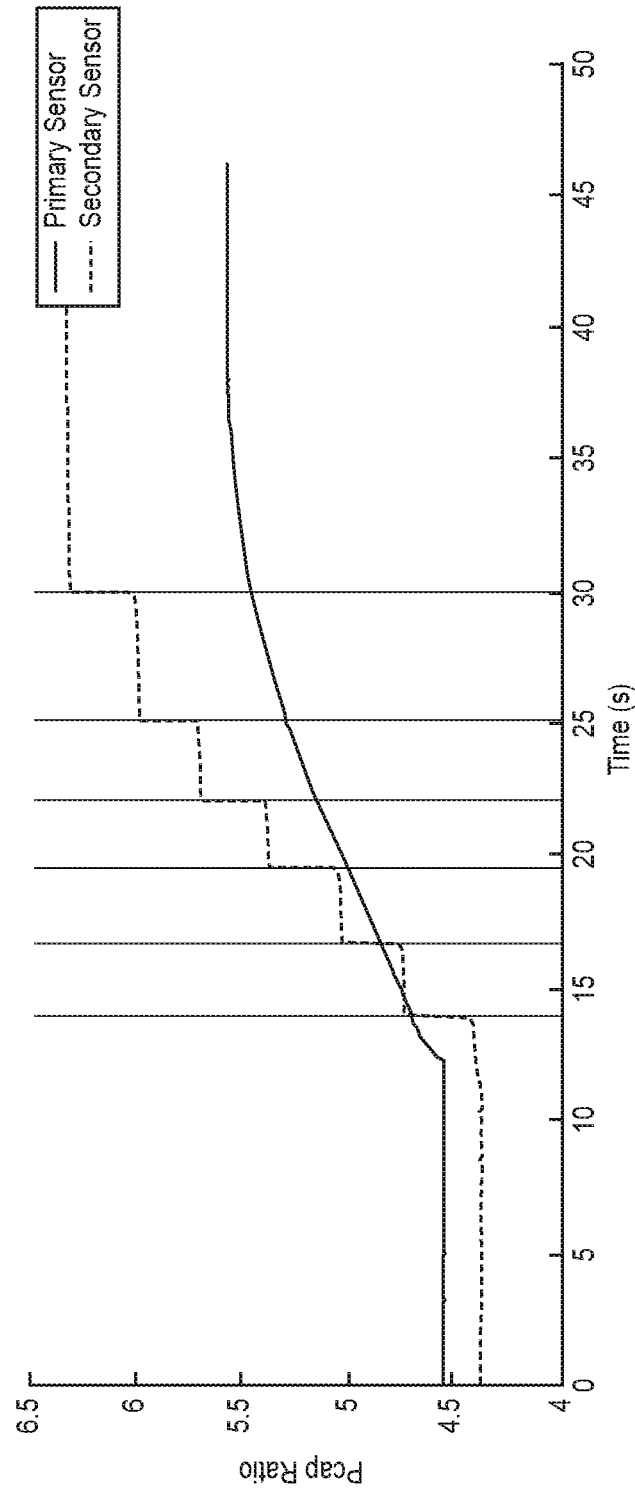
FIG. 14A is a plot showing the differences between the capacitance readings of the primary capacitive sensor and the secondary capacitive sensor of FIGS. 13A-13B.

FIG. 14A is a plot showing the differences between the capacitance readings of the primary capacitive sensor 1302 and the second capacitive sensor 1304 of the sensing device 1300. In examples, the readings from the secondary capacitive sensor 1304 can be used to create a calibration from the data from the primary capacitive sensor 1302 to the volume at the particular grounded capacitive plate 1306 at the trigger point 1308 in the container portion 102.

Figure 14B:
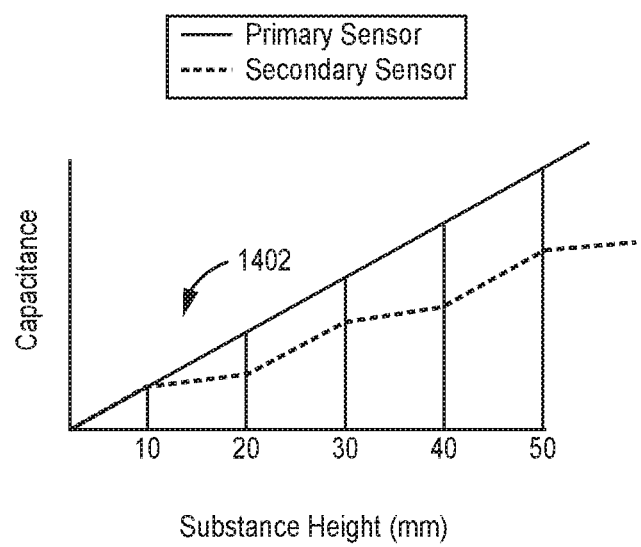
FIG. 14B is a plot showing the differences between the capacitive readings of the primary capacitive sensor and the secondary capacitive sensor of FIG. 13C.

FIG. 14B is a plot showing the differences between the capacitance readings of the primary capacitive sensor 1302 and the secondary capacitive sensor 1312 of the sensing device 1310. The secondary capacitive sensor 1312 is continuous but has distinct changes in the capacitive areas at known heights or container volumes. Consequently, the secondary capacitive sensor 1312 can identify an event timing where a known height or volume was achieved in the filling event. This noted change in the second capacitive sensor 1312 value can then be related to the reading at that time on the primary sensor 1302.

Figure 15:
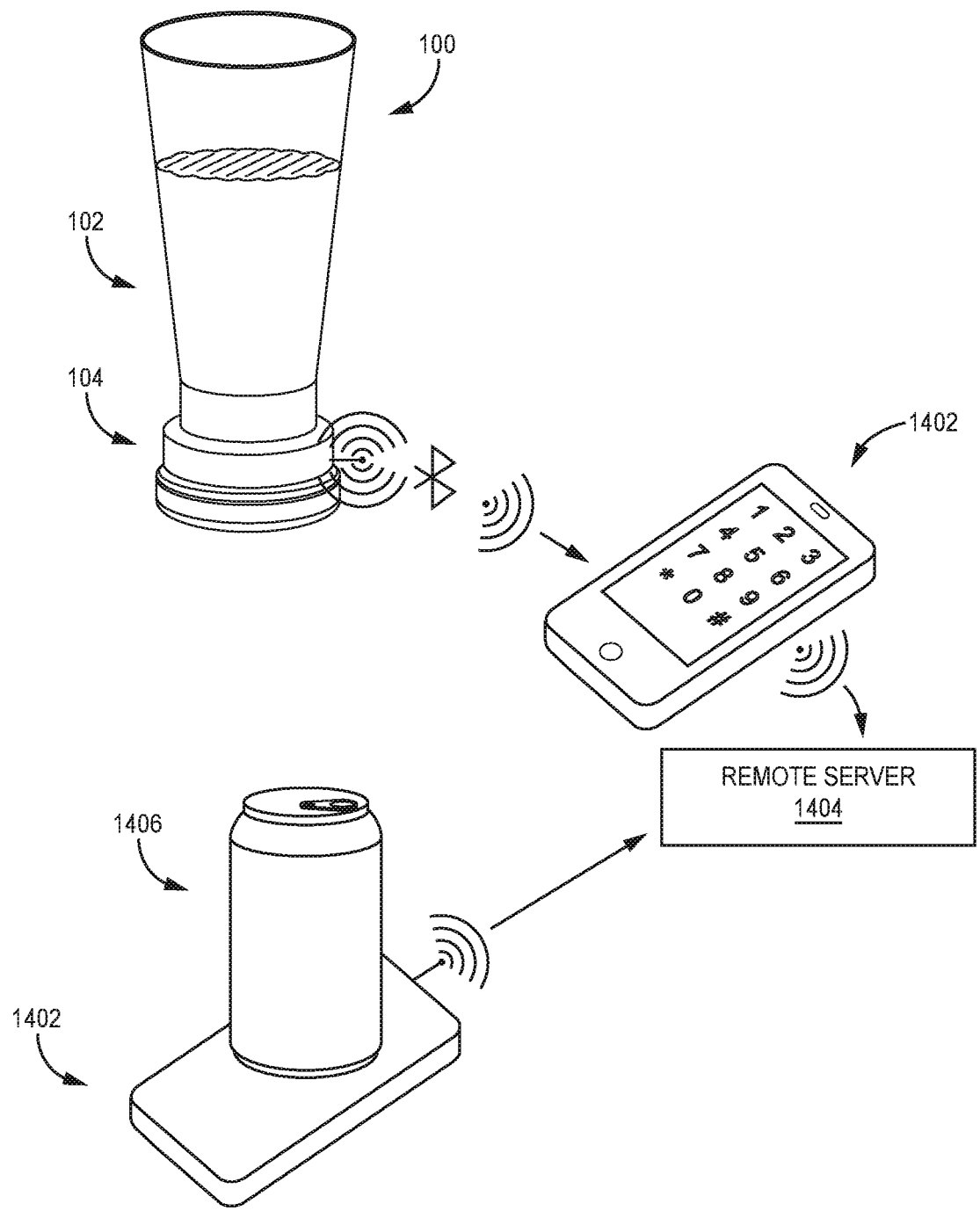
FIG. 15 is a diagram including both measurement of urine data and fluid consumed data using the urine measurement device and a smart device.

FIG. 15 is a diagram including both measurement of urine data and fluid consumed data using the urine measurement device 100 and a smart device 1402. In examples, urine data is collected using the urine measurement device 100 (including the container portion and the electronics portion 104); which data is then transferred wirelessly to an app of a smart device 1402 from the electronics portion 104; which data is then transmitted from the smart device 1402 to a remote server 1404, such as a web portal or other server through the Internet. This measuring of the voiding of urine is considered the "Outgo". Another function of the app of the smart device (such as a smart phone or tablet) may include a fluid consumption or "Intake" app that tracks fluids consumed and sends data regarding the fluids consumed wirelessly to the same web portal or other server. In examples, the intake portion is accomplished by a smart device (such as a smart phone or tablet) taking the fluid weight directly by placing a container 1406 with fluid directly on the screen of the smart device 1402.

The twenty-four (24) hour voiding diary is valuable data for urologists treating patients with LUTS (lower urinary track symptoms). However, tracking fluid outgo is only part of the patient's condition. Tracking fluid intake would complete the diagnostic picture and could be used as feedback regarding MTM (medication therapy management) in the treatment of patients with heart disease and systemic fluid accumulation and/or patients at risk for pulmonary edema. The tracking of Intake fluids to be included with the voiding amounts and voiding frequencies to achieve a 24 hour intake/voiding diary. In examples, a pressure based measurement capability on smartphones is used to measure volume of fluids consumed as well as entering the type of fluid consumed. In examples, it also may be desirable to include not only weighing the fluid consumed and type of fluid consumed but weighing food to be consumed and the type of food consumed. Some smartphones (and other devices) include pressure sensitive displays. For example, Apple® iPhone® 6s and iPhone® 6s Plus included 3D Touch® which uses pressure sensitivity built into the device to sense how hard you press the display. The 3D Touch® display can not only sense multiple points of input, but can also sense how much pressure the user applies to the screen. By distinguishing different amounts of applied pressure applied by the user to the screen, the user can accomplish one action by pressing lightly and a different action by pressing harder. By pressing harder, the user produces pressure that allows the finger to press into the display on a microscopic level, allowing the user to interact with the display in three dimensions.

This pressure sensing capability of the screen on smartphones 1402 (or other smart device, such as a tablet) allows the smart device to be used to weigh things. A substance (such as a liquid) can be poured into a container placed on the display of the smartphone (or other smart device) and the pressure sensitive display on the smartphone 1402 (or other smart device) can act as a scale, showing how much the material weighs. In examples, this pressure sensitive display on the smartphone 1402 (or other smart device) is used to weigh fluid (and/or food or another substance) consumed by a patient, which can then be used to accurately track the amount of fluid (and/or food or another substance) consumed in a fluid intake diary (and/or food intake diary or another substance intake diary).

In examples, fluid (and/or food or another substance) intake is tracked with reference to medical or medication therapy. In examples, fluid amounts (and/or food or another substance) consumed and fluid types (and/or food types or another substance types) are tracked and stored on a smart device. In examples, the consumption data is stored on a remote server. While pressure sensitive smart devices are described herein as the means for measuring the fluid intake, it is understood separate weight or pressure based scales could also be used (such as an electronic "coaster" that transmits data via a wireless or wired connection).

Smart phones and other smart devices are ubiquitous. Enabling patients to easily and conveniently track their fluid intake with accuracy and precision using the pressure sensitivity built into the device that is already in their purse or pocket would be a huge step forward in making home or remote MTM a reality.

Figure 16:
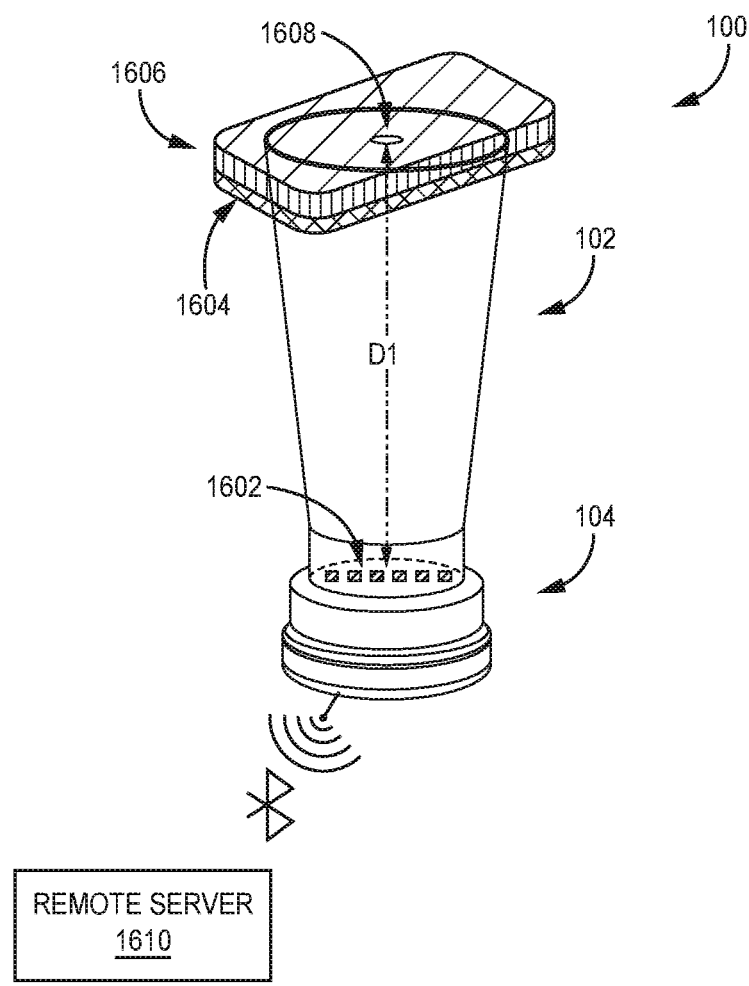
FIG. 16 is a diagram showing a urine measurement device also capable of performing portions of a urine analysis test.

FIG. 16 is a diagram showing a urine measurement device 1600 (such as a derivative of urine measurement device 100) that is also capable of performing portions of a urine analysis test. In examples, at least one of the container portion 102 and the top of the electronics portion 104 of the urine measurement device 1600 are configured to receive urine analysis reagent test strips 1602 (such as urine analysis reagent test strips). In examples, the urine measurement device 100 further includes a lid portion 1604. In examples, the container portion 102 and the lid portion 1604 are light blocking (to limit light pollution from degrading the accuracy of reading the urine analysis reagent test strips with the smart device camera and flash). The lid portion 1604 serves the purpose of providing a support structure for a smart phone 1606 (or tablet or other smart device) with a camera 1608 (or a stand alone camera 1608), blocking light into the container portion 102, and providing a constant distance D1 from the lens of the camera 1608 to the urine analysis reagent test strip 1602, each of which aid in achieving an accurate reading of the urine analysis reagent test strips. In examples, the urine measurement device 100 is configured to transmit data to the remote server 1610.

In examples, uroflowmetry is combined with urine analysis or urine analysis with uroflowmetry. Currently, uroflowmetry is a stand-alone test that measures the urine voided volume, flow profile, peak flow, average flow, time to peak flow, and other parameters of interest and importance to urologists. Urine analysis includes is a test where at least one urine analysis reagent test strip 1602 is placed into urine and values from the urine constituents (such as, but not limited to, glucose, creatinine, ketones, blood, pH, protein, nitrites, leucocytes, urobilinogen, specific gravity, and bilirubin) are read off the test strip 1602 in a stand-along procedure using a separate urine analysis machine. As healthcare costs continue to rise and accessibility becomes more complicated, simple procedures and diagnostic tests will continue to move into the home or remote clinic settings. Currently, uroflow studies and urine analysis are two different procedures. In examples described herein, both uroflow and urine analysis can be completed during the same void, either simultaneously or sequentially.

Urine constituent analysis can occur using urine analysis reagent test strips exposed to urine and then read using a light (wavelength) reader. (http://www.healthcare.siemens.com/point-of-care/urinalysis/multistix-10-sg-reagent-strips/ and http://usa.healthcare.siemens.com/point-of-care/urinalysis/). More recently there have been several App-based approaches to implementing urine analysis by reading urine analysis reagent test strips remotely using a smart device's camera feature (smartphone or tablet). These Apps can read partial or complete urine analysis reagent test strips, determining the concentration and/or presence of urine constituents such as but not limited to Leukocytes, Nitrites, Urobilinogen, Protein, pH, Blood, Specific Gravity, Ketone, Bilirubin, Glucose, and Creatinine (FIG. 8A-8B, at least one sensor 806). These readings by a smart device can serve as a helpful indicator but have some basic limitations. The readings can be error prone due to variable ambient lighting conditions and distance D1 from the camera lens to the urine strip. Additionally these urine analysis readings miss an important component in the overall diagnostic assessment of the LUTS patient, specifically collecting flow rate, volume, date and timing among other data.

While blood samples can provide good data regarding levels of various constituents in the body, urine is easier to analyze than blood. In examples, an app on a smart device is configured to take an image of at least one urine analysis reagent test strip that is on or in a portable, capacitance based urine flowmeter configured to measure the volume and flow rates of urine. While the description is described in the context of uroflowmetry and urine analysis, it is understood that flowmetry of other fluids and/or substances and analysis of the other fluid or substances can also be combined in similar ways. The urine analysis applies to a number of urine analysis constituents and other elements regarding a person's health and condition and is not limited in scope to any particular constituent. A number of potential urine constituents that are of particular interest in measuring during a urine analysis study are described at http://craigmedical.com/urinalysis_techs.htm, which is hereby incorporated by reference.

Creatinine is a waste product in your blood. It comes from protein in your diet and the normal breakdown of muscles of your body. Creatinine is removed from blood by the kidneys and then passes out of the body in your urine. If you have kidney disease, the level of creatinine in your blood increases. Blood (serum) and urine tests can check your creatinine levels. The tests are done to check how well your kidneys are working. A high serum or urine creatinine level can mean that your kidneys aren't working well. A creatinine level may temporarily increase if you are dehydrated, have a low blood volume, eat a large amount of meat or take certain medications. Dietary supplemental creatinine can have the same effect.

Glucose is a simple sugar that circulates in the blood of animals as blood sugar. It is an important source of energy for cellular respiration. The glucose reagent panel is specific for glucose and no substance other than glucose is known to give a positive result. The reactivity of the glucose test decreases as the Specific Gravity of the urine increases. Reactivity may also vary with temperature. Small amounts of glucose may normally be excreted by the kidneys, these amounts are usually below the sensitivity range of this test but on occasion may produce a color between the 'Negative' and the 100/5 color block and may be interpreted by the observer as positive. Glycosuria is the condition of glucose in urine. Normally the filtered glucose is reabsorbed by the renal tubules and returned to the blood by carrier molecules. If blood glucose levels exceed renal threshold levels, the un-transported glucose will spill over into the urine. A common cause of high glucose levels is diabetes mellitus.

Ketones are alternative fuels for the body that are made when glucose is in short supply, such as overnight and during dieting and fasting. They are made in the liver from the breakdown of fats. Ketones may form in the blood and make their way into urine. Too many ketones can make individuals sick. The ketone test reacts with acetoacetic acid in urine. It does not react with acetone or beta-hydroxybutyric acid. Some high specific gravity/low pH urines may give reactions up to and including 'Trace'. Normal urine specimens usually yield negative results with this reagent. False positive results (trace or less) may occur with high pigmented urine specimens or those containing large amounts of levodopa metabolites. Ketone bodies such as acetoacetic acid, beta-hydroxybutyric acid, and acetone can appear in urine in small amounts. These intermediate by-products are associated with the breakdown of fat. Common causes of high ketone levels include diabetes mellitus, starvation, and diarrhea.

Blood in urine can be indicative of medical conditions. The significance of the 'Trace' reaction may vary among patients, and clinical judgment is required for assessment in an individual case. Development of green spots (intact erythrocytes) or a green color (free hemoglobin/myoglobin) on the reagent area within 60 seconds indicates the need for further investigation. Blood is often found in the urine of menstruating females. This test is highly sensitive to hemoglobin and thus compliments the microscopic examination. This test is equally sensitive to myoglobin as to hemoglobin. The sensitivity of this test may be reduced in urines with high specific gravity. Captopril may cause decreased reactivity. False positives reactions can be caused by certain oxidizing contaminants such as hypochlorite—microbial peroxiclase associated with urinary 'tract infection may also give a false positive reaction. Levels of ascorbic acid normally found in urine do not interfere with this test. Hemoglobinuria is the presence of hemoglobin in the urine. Common causes of blood in urine include hemolytic anemia, blood transfusion reactions, massive burns, and renal disease. Hematuria is the presence of intact erythrocytes and is usually pathological. Common causes of hematuria includes kidney stones, tumors, glomerulonephritis, physical trauma, urinary tract infection, and Prostatitis (the swelling and inflammation of the prostate gland).

The pH level of urine can be indicative of certain medical conditions. The pH test area measures pH values generally within 1 unit in the range of 5-8.5 visually and 5-9 instrumentally with 5 being very acidic and 8.5 being highly alkaline. Generally, urine pH results range from 5.5-7.5 in a bell curve type statistical distribution. Average for normal human urine is slightly acidic 6.0, however deviations from normal in any given sample are unremarkable and consistent, repeated readings are required in the top or bottom range to suggest an abnormality. High protein diets increase acidity. Vegetarian diets increase alkalinity. Bacterial infections also increase alkalinity producing a urine pH in the higher 7-8 range.

Protein in urine can be indicative of certain medical conditions. The reagent area is more sensitive to albumin than to globulins, hemoglobin, and mucoprotein. A 'Negative' result does not rule out the presence of other proteins. Normally no protein is detectable in urine by conventional methods, although a minute amount is excreted by the normal kidney. A color matching any block greater than 'Trace' indicates significant proteinuria. For urine of high specific gravity, the test area may most closely match the 'Trace' color block even though only normal concentrations of protein are present. Clinical judgment is needed to evaluate the significance of 'Trace' results. False positive results may be obtained with highly alkaline urines. Albumin is normally too large to pass through glomerulus tissue. Therefore elevated results Indicate abnormal increased permeability of the glomerulus membrane. Non-pathological causes of protein in urine include pregnancy, physical exertion, and increased protein consumption. Pathological causes of protein in urine include glomerulonephritis bacterial toxins and chemical poisons.

High levels of nitrite in urine can be indicative of certain medical conditions. This test depends upon the conversion of nitrate (derived from the diet) to nitrite by the action of principally gram negative bacteria in the urine. The test is specific for nitrite and will not react with any other substance normally excreted in urine. Pink spots or pink edges should not be interpreted as a positive result. Any degree of uniform pink color development should be interpreted as a positive nitrite test suggesting the presence of 100000 or more organisms per ml, but color development is not proportional to the number of bacteria present. A negative result does not in itself prove that there is no significant bacteriuria. Negatives may occur when urinary tract infections are caused by organism which do not contain reductase to convert nitrate to nitrite; when urine has not been retained in the bladder long enough (4 hours or more) for reduction of nitrate to occur; or when dietary nitrate is absent, even if organisms containing reductase are present and the bladder incubation is ample. Sensitivity of the nitrite test is reduced for urines with a high specific gravity. High abnormal readings indicate the presence of bacteria. Causes of high levels of nitrite in urine include urinary tract infection.

Leucocytes (also referred to as white blood cells) are cells that circulate in blood, urine, and other body fluids and are involved in counteracting foreign substances and disease. Normal urine specimens generally yield negative results. Positive results of small (+) or greater are clinically significant. Individually observed 'Trace' results may be of questionable clinical significance. However, 'Trace' results observed repeatedly may be clinically significant. 'Positive' results may occasionally be found with random specimens from females due to contamination of the specimen by vaginal discharge. Elevated glucose concentrations or high specific gravity may cause decreased test results. The presence of leukocytes in urine is referred to as pyuria (pus in the urine). Causes of leucocytes in urine include urinary tract infection and Prostatitis (the swelling and inflammation of the prostate gland).

Urobilinogen is a colorless by-product of bilirubin reduction. It is formed in the intestines by bacterial action on bilirubin. About half of the urobilinogen formed is reabsorbed and taken up via the portal vein to the liver, enters circulation and is excreted by the kidney. This test area will detect urobilinogen in concentrations as low as 3 mIU/L (milli-international units per liter) in urine. The reagent area may react with substances known to interfere with Ehrlich's reagent, such as p-aminosalicylic acid and sulphonamides. Atypical color reactions may be obtained in the presence of high concentrations of p-aminobenzoic. False negative results may be obtained if formalin is present. Highly colored substances, such as azo dyes and riboflavin may mask color development on the reagent area. Strip reactivity increases with temperature. The optimum temperature is 22-26 degrees centigrade. The absence of urobilinogen cannot be determined with this test. Bile pigment derived from breakdown of hemoglobin. The majority of this substance is excreted in the stool, but small amounts are reabsorbed into the blood from the intestines and then excreted into the urine. Causes of urobilinogen in urine includes hemolytic anemia and liver diseases.

Specific gravity of urine is a measurement of the density of urine. It is the relative proportions of dissolved solids in relationship to the total volume of the specimen. It reflects how concentrated or diluted a sample may be. Water has a specific gravity of 1.000. Urine will always have a value greater than 1.000 depending upon the amount of dissolved substances (salts, minerals, etc.) that may be present. Very dilute urine has a low specific gravity value and very concentrated urine has a high value. Specific gravity measures the ability of the kidneys to concentrate or dilute urine depending on fluctuating conditions. Normal range 1.005-1.030, average range 1.010-1.025. The specific gravity test permits the determination of urine specific gravity between 1.000 and 1.030. In general, it correlates within 0.005 with values obtained with the refractive index method. For increased accuracy, 0.005 may be added to readings from urine with pH equal to or greater than 6.5. Elevated specific gravity readings may be obtained in the presence of moderate quantities (1 7.5 g/L) of protein. Low specific gravity of is associated with conditions like diabetes insipidus, excessive water intake, diuretic use or chronic renal failure.

Bilirubin is a pigment formed in the liver by the breakdown of hemoglobin and excreted in bile. Normally no bilirubin is detected in urine by even the most sensitive methods. Even trace amounts of bilirubin are sufficiently abnormal to require further investigation. Atypical result colors may indicate bile pigment abnormalities and the urine specimen should be tested further by more quantitative laboratory means. Metabolites of drugs which give a color at low pH, such as Pyridium and Serenium may cause false positives. Ascorbic acid concentrations of 1.42 mIU/L (milli-international units per liter) or greater may cause false positives. Bilirubin comes from the breakdown of hemoglobin in red blood cells. The globin portion of hemoglobin is split off and the heme groups of hemoglobin are converted into the pigment bilirubin. Bilirubin is secreted in blood and carried to the liver where it is conjugated with glucuronic acid. Some is secreted in blood and some is excreted in the bile as bile pigments into the small intestines. Bilirubin in urine can be caused by liver disorders, cirrhosis, hepatitis, and obstruction of bile duct.

Capturing urine analysis data from a smart device photograph of a urine analysis reagent test strip requires three (3) things: (1) determining the "yellowness" of the urine to subtract that "variability" aspect out of the reading, (2) a constant focal length for the optical measurement, and (3) a controlled or known ambient lighting condition. This invention describes how to control these variables facilitating a consistent and accurate interpretation of the urine analysis constituent values. In examples, the urine analysis reagent test strips are used during or immediately after the voiding event where urine flow and/or volume was measured. The data values (such as height, volume, and/or flow rate) from the voiding event at particular time and/or date can be wirelessly communicated or communicated with wires to a remote server.

In examples, at least one substance analysis position within the container portion 102 (including on top of the electronics portion 104) is configured to position at least one substance analysis strip 1602 within the substance. In examples, the substance analysis strip 1602 is a urine analysis reagent strip 1602 that is used for analysis of at least one of: Leukocytes, Nitrites, Urobilinogen, Protein, pH, Blood, Specific Gravity, Ketone, Bilirubin, Glucose, and Creatinine. In examples, the lid portion 1604 blocks ambient light pollution into the container portion 102 and allows the camera 1608 (and flash) to take a photograph of the at least one substance analysis strip 1602 within the container portion 102 while providing the following for repeatable and accurate analysis of the photograph of the at least one substance analysis strip 1602: (1) a known focal length for the photograph and/or a known distance D1 between the camera 1608 and the at least one substance analysis strip 1602 within the container portion 102; and (2) known ambient lighting condition and/or a controlled ambient lighting condition. In examples, the urine measurement device 100 is configured to transmit the photograph to the remote server 1610 from the electronics portion 104.

Sending data wirelessly or wired connection or saving data directly to an internal memory device involve sending additional information (date, time, device serial number, general device health parameters, calibration, among other data elements). Additional information helps identify and track various electronic data capturing devices and the electronic components contained therein (component lot numbers, board sources, assembly data, etc); to facilitate device identification for any reason, potential recalls, component end of life, etc.

Example Embodiments

Example 1 includes a printed circuit board device, comprising: a first capacitive sensor configured to measure a first capacitance within a contained volume having known dimensions, wherein the first capacitance changes as a substance is received into the contained volume; a second capacitive sensor having a plurality of trigger points at a plurality of corresponding known heights within the contained volume, the second capacitive sensor configured to detect when the substance received into the contained volume has reached each of the corresponding known heights within the contained volume; and wherein at least one of a level of the substance within the contained volume, a volume of the substance within the contained volume, or a flow rate of the substance into the contained volume is determined based on data from the first capacitive sensor and the second capacitive sensor.

Example 2 includes the printed circuit board device of Example 1, wherein each trigger point of the plurality of trigger points is connected to a corresponding capacitive plate of the second capacitive sensor that is grounded when the substance touches the trigger point resulting in a step change in a capacitance reading.

Example 3 includes the printed circuit board device of any of Examples 1-2, wherein each trigger point of the plurality of trigger points includes a point on the second capacitive sensor where the area of the capacitive sensor changes substantially resulting in a step change in a capacitance reading.

Example 4 includes the printed circuit board device of any of Examples 1-3, wherein data from the second capacitive sensor is used to at least one of calibrate, filter, augment, or correct a determination of at least one of the level of the substance within the contained volume, the volume of the substance within the contained volume, or the flow rate of the substance into the contained volume based on the first capacitive sensor.

Example 5 includes the printed circuit board device of any of Examples 1-4, wherein the first capacitance is indicative of at least one of the level of the substance within the contained volume, the volume of the substance within the contained volume, or the flow rate of the substance into the contained volume.

Example 6 includes the printed circuit board device of any of Examples 1-5, wherein the first capacitance is indicative of a level of the substance within the contained volume; wherein the volume of the substance within the contained volume is determined based on the level of the substance within the contained volume and a known geometry of the contained volume; and wherein the flow rate of the substance within the contained volume is determined by subtracting a first volume determined at a first time from a second volume determined at a second time to determine a difference between the second volume and the first volume and dividing the difference by an elapsed time between the first time and the second time.

Example 7 includes the printed circuit board device of any of Examples 1-6, wherein the second capacitive sensor includes a capacitance ladder.

Example 8 includes the printed circuit board device of any of Examples 1-7, wherein the substance is a liquid.

Example 9 includes the printed circuit board device of any of Examples 1-8, wherein the substance is urine.

Example 10 includes a substance measurement device, comprising: a container portion configured to receive a substance; a first capacitive sensor configured to measure a first capacitance related to the substance within the container portion, wherein the first capacitance changes as the substance is received into the container portion; a second capacitive sensor having a plurality of trigger points at a plurality of corresponding known heights within the container portion, the second capacitive sensor configured to detect when the substance received into the container portion contacts each of the plurality of plates indicating the substance received into the container portion has reached each of the corresponding known heights within the container portion; and wherein at least one of a level of the substance within the container portion, a volume of the substance within the container portion, or a flow rate of the substance into the container portion is determined based on data from the first capacitive sensor and the second capacitive sensor.

Example 11 includes the substance measurement device of any of Examples 1-10, wherein each trigger point of the plurality of trigger points is connected to a corresponding capacitive plate of the second capacitive sensor that is grounded when the substance touches the trigger point resulting in a step change in a capacitance reading.

Example 12 includes the substance measurement device of any of Examples 1-11, wherein each trigger point of the plurality of trigger points includes a point on the second capacitive sensor where the area of the capacitive sensor changes substantially resulting in a step change in a capacitance reading.

Example 13 includes the substance measurement device of any of Examples 10-12, wherein data from the second capacitive sensor is used to at least one of calibrate, filter, augment, or correct a determination of at least one of the level of the substance within the container portion, the volume of the substance within the container portion, or the flow rate of the substance into the container portion based on the first capacitive sensor.

Example 14 includes the substance measurement device of any of Examples 10-13, wherein the first capacitance is indicative of at least one of the level of the substance within the container portion, the volume of the substance within the container portion, or the flow rate of the substance into the container portion.

Example 15 includes the substance measurement device of any of Examples 10-14, wherein the first capacitance is indicative of a level of the substance within the container portion; wherein the volume of the substance within the container portion is determined based on the level of the substance within the container portion and a known geometry of the container portion; and wherein the flow rate of the substance within the container portion is determined by subtracting a first volume determined at a first time from a second volume determined at a second time to determine a difference between the second volume and the first volume and dividing the difference by an elapsed time between the first time and the second time.

Example 16 includes the substance measurement device of any of Examples 10-15, wherein the second capacitive sensor includes a capacitance ladder.

Example 17 includes the substance measurement device of any of Examples 10-16, wherein the first capacitive sensor and the second capacitive sensor are located in close proximity to one another and the second capacitive sensor is used to at least one of calibrate, filter, augment, or correct a determination of at least one of the level of the substance within the container portion, the volume of the substance within the container portion, or the flow rate of the substance into the container portion based on the first capacitive sensor.

Example 18 includes the substance measurement device of any of Examples 10-17, wherein the first capacitive sensor and the second capacitive sensor are fabricated on a single printed circuit board.

Example 19 includes the substance measurement device of any of Examples 10-18, wherein the substance is a liquid.

Example 20 includes the substance measurement device of any of Examples 10-19, wherein the substance is urine.

Example 21 includes a method, comprising: sensing a first capacitance within a contained volume at various time points using a first capacitive sensor, wherein the first capacitance changes as a substance is received into the contained volume, wherein the contained volume has known dimensions; detecting when the substance received into the contained volume reaches each of a plurality of trigger points on a second capacitive sensor at a plurality of corresponding known heights within the contained volume when the substance received into the contained volume reaches each of a plurality of plurality of heights within the contained volume; and determining at least one of a level of the substance within the contained volume, a volume of the substance within the contained volume, or a flow rate of the substance into the contained volume based on the first capacitance at the various time points and when the contained volume reaches each of the plurality of heights within the contained volume.

Example 22 includes the method of Example 21, wherein each trigger point of the plurality of trigger points is connected to a corresponding capacitive plate of the second capacitive sensor that is grounded when the substance touches the trigger point resulting in a step change in a capacitance reading.

Example 23 includes the method of any of Examples 21-22, wherein each trigger point of the plurality of trigger points includes a point on the second capacitive sensor where the area of the capacitive sensor changes substantially resulting in a step change in a capacitance reading.

Example 24 includes the method of any of Examples 21-23, wherein the determination of when the contained volume reaches each of the plurality of heights within the contained volume is used for at least one of calibrating, filtering, augmenting, or correcting a determination of at least one of the level of the substance within the contained volume, the volume of the substance within the contained volume, or the flow rate of the substance into the contained volume.

Example 25 includes the method of any of Examples 21-24, wherein the first capacitance is indicative of at least one of the level of the substance within the contained volume, the volume of the substance within the contained volume, or the flow rate of the substance into the contained volume.

Example 26 includes the method of any of Examples 21-25, further comprising: wherein the first capacitance is indicative of a level of the substance within the contained volume; determining the volume of the substance within the contained volume based on the level of the substance within the contained volume and a known geometry of the contained volume; and determining the flow rate of the substance within the contained volume by subtracting a first volume determined at a first time from a second volume determined at a second time to determine a difference between the second volume and the first volume and dividing the difference by an elapsed time between the first time and the second time.

Example 27 includes the method of any of Examples 21-26, wherein the substance is a liquid.

Example 28 includes the method of any of Examples 21-27, wherein the substance is urine.

Example 29 includes a substance measurement and analysis device, comprising: a container portion configured to receive a substance; a sensing device configured to measure a property of the substance related to at least one of a level of the substance within the container portion, a volume of the substance within the container portion, or a flow rate of the substance into the container portion; at least one substance analysis position within the container portion configured for positioning at least one substance analysis strip within the substance; and a lid portion configured to be placed on top of the container portion and configured to allow a camera and a flash to take a photograph of the at least one substance analysis strip within the container portion while providing the following for repeatable and accurate analysis of photographs of the at least one substance analysis strip: at least one of a known focal length for the photograph or a known distance between the camera and the at least one substance analysis strip within the container portion; and at least one of a known ambient lighting condition or a controlled ambient lighting condition.

Example 30 includes the substance measurement and analysis device of Example 29, wherein the photograph is provided to an external device for analysis.

Example 31 includes the substance measurement and analysis device of any of Examples 29-30, wherein the camera and flash are part of at least one of a smart phone, a tablet, or other smart device.

Example 32 includes the substance measurement and analysis device of any of Examples 29-31, wherein the container portion and the lid portion are configured to substantially block light from outside of the container portion other than light provided by the flash to mitigate distortion or contamination of the photograph and analysis of the substance analysis strip by light from outside of the container portion.

Example 33 includes the substance measurement and analysis device of any of Examples 29-32, wherein the substance analysis position is at least one of positioned on an interior side wall of the container portion or at the bottom of the container portion.

Example 34 includes the substance measurement and analysis device of any of Examples 29-33, wherein the at least one substance is urine; wherein the at least one substance analysis strip includes at least one urine analysis strip; and wherein the at least one substance analysis strip is configured to test for at least one of leukocytes, nitrites, urobilinogen, protein, pH, blood, specific gravity, ketone, bilirubin, glucose, or creatinine in the urine.

Example 35 includes the substance measurement and analysis device of any of Examples 29-34, further comprising: at least one memory configured to store the photograph in a file; and at least one wireless network device configured to transmit the file to a remote server.

Example 36 includes the substance measurement and analysis device of any of Examples 29-35, wherein the at least one substance analysis test strip includes a white area that absorbs the substance to provide information regarding the color of the sub stance.

Example 37 includes the substance measurement and analysis device of any of Examples 29-36, wherein the at least one substance analysis test strip includes a white area that does not absorb the substance to provide information regarding white balance for correction of white balance within the photograph.

Example 38 includes the substance measurement and analysis device of any of Examples 29-37, further comprising: at least one sensor configured to determine the color of the substance to assist in the accuracy of reading the substance analysis strips.

Example 39 includes a method, comprising: receiving a substance into a container portion of a substance measurement and analysis device; measuring a property of the substance related to at least one of a level of the substance within the container portion, a volume of the substance within the container portion, or a flow rate of the substance into the container portion; positioning at least one substance analysis strip within the substance within the container portion; placing a lid portion onto the container portion; and taking a photograph of the at least one substance analysis strip through at least one hole provided in the lid portion of the container portion.

Example 40 includes the method of Example 39, wherein the lid portion is configured to allow a camera and a flash to take a photograph of the at least one substance analysis strip within the container portion while providing the following for repeatable and accurate analysis of photographs of the at least one substance analysis strip: at least one of a known focal length for the photograph or a known distance between the camera and the at least one substance analysis strip within the container portion; and at least one of a known ambient lighting condition or a controlled ambient lighting condition.

Example 41 includes the method of any of Examples 39-40, further comprising: analyzing the photograph of the at least one substance analysis strip.

Example 42 includes the method of any of Examples 39-41, further comprising: transmitting the photograph of the at least one substance analysis strip to an external device; and analyzing the photograph of the at least one substance analysis strip at the external device.

Example 43 includes the method of any of Examples 39-42, wherein the container portion and the lid portion are configured to substantially block light from outside of the container portion other than light provided by a flash through the at least one hole provided in the lid portion to mitigate distortion or contamination of the photograph and analysis of the substance analysis strip by light from outside of the container portion.

Example 44 includes the method of any of Examples 39-43, wherein positioning at least one substance analysis strip within the substance within the container portion includes positioning the at least one substance analysis strip on at least one of an interior side wall of the container portion or the bottom of the container portion.

Example 45 includes the method of any of Examples 39-44, wherein the at least one substance is urine; wherein the at least one substance analysis strip includes at least one urine analysis strip; and wherein the at least one substance analysis strip is configured to test for at least one of leukocytes, nitrites, urobilinogen, protein, pH, blood, specific gravity, ketone, bilirubin, glucose, or creatinine in the urine.

Example 46 includes the method of any of Examples 39-45, wherein the at least one substance analysis test strip includes a white area that absorbs the substance to provide information regarding the color of the substance.

Example 47 includes the method of any of Examples 39-46, wherein the at least one substance analysis test strip includes a white area that does not absorb the substance to provide information regarding white balance for correction of white balance within the photograph.

Example 48 includes a system for tracking at least one of fluid and food intake during Medication Therapy Management (MTM), the system comprising: a smart device including at least one of a pressure sensing device or a weight sensing device, the smart device configured to determine weight of at least one of fluid and food received into a container placed on top of the smart device using the at least one of the pressure sensing device or the weight sensing device, wherein the at least one of the fluid and the food is consumed by an individual, wherein the smart device is configured to track amounts and types of at least one of fluid or food consumed by the individual based on the weight of the at least one of the fluid or the food; and a remote server communicatively coupled with the smart device and configured to receive data regarding the fluid amounts and types consumed by the individual from the smart device.

Example 49 includes the system of Example 48, further comprising: a urine measurement device including: a container portion configured to receive urine from the individual; and a sensing device configured to measure a property of the urine related to at least one of a level of the urine within the container portion, a volume of the urine within the container portion, or a flow rate of the urine into the container portion; wherein the smart device is configured to receive the data regarding the property of the urine from the urine measurement device; wherein the smart device is configured to determine the at least one of the level of the urine within the container portion, the volume of the urine within the container portion, or the flow rate of the urine into the container portion; and wherein the smart device is configured to communicate data regarding the at least one of the level of the urine within the container portion, the volume of the urine within the container portion, or the flow rate of the urine into the container portion to the remote server.

Example 50 includes the system of any of Examples 48-49, further comprising: a urine measurement device including: a container portion configured to receive urine from the individual; and a sensing device configured to measure a property of the urine related to at least one of a level of the urine within the container portion, a volume of the urine within the container portion, or a flow rate of the urine into the container portion; wherein the smart device is configured to receive the data regarding the property of the urine from the urine measurement device; wherein the smart device is configured to communicate the data regarding the property of the urine to the remote server; and wherein the remote server is configured to determine the at least one of the level of the urine within the container portion, the volume of the urine within the container portion, or the flow rate of the urine into the container portion based on the data regarding the property of the urine.

Example 51 includes the system of any of Examples 48-50, wherein the at least one of the pressure sensing device or the weight sensing device includes a pressure sensitive touchscreen.

Example 52 includes a method for tracking at least one of fluid and food intake during Medication Therapy Management (MTM), the method comprising: determining weight of at least one of a fluid and food received into a container placed on top of a smart device using at least one of a pressure sensing device or a weight sensing device built into the smart device, wherein the at least one of the fluid or the food is consumed by an individual; tracking amounts and types of at least one of fluid or food consumed by the individual based on the weight of the at least one of the fluid or the food; and receiving data regarding the fluid amounts and types consumed by the individual from the smart device at a remote server.

Example 53 includes the method of Example 52, further comprising: receiving a substance into a container portion of a substance measurement and analysis device; measuring a property of the substance related to at least one of a level of the substance within the container portion, a volume of the substance within the container portion, or a flow rate of the substance into the container portion; receiving data regarding the property of the urine from the urine measurement device at the smart device; determining the at least one of the level of the urine within the container portion, the volume of the urine within the container portion, or the flow rate of the urine into the container portion at the smart device based on the data regarding the property of the urine; and communicating data regarding the at least one of the level of the urine within the container portion, the volume of the urine within the container portion, or the flow rate of the urine into the container portion from the smart device to the remote server.

Example 54 includes the method of any of Examples 52-53, further comprising: receiving a substance into a container portion of a substance measurement and analysis device; measuring a property of the substance related to at least one of a level of the substance within the container portion, a volume of the substance within the container portion, or a flow rate of the substance into the container portion; receiving data regarding the property of the urine from the urine measurement device at the smart device; communicating the data regarding the property of the urine to the remote server from the smart device; and determining at least one of the level of the urine within the container portion, the volume of the urine within the container portion, or the flow rate of the urine into the container portion based on the data regarding the property of the urine at the remote server.

Example 55 includes the system of any of Examples 52-54, wherein the at least one of the pressure sensing device or the weight sensing device includes a pressure sensitive touchscreen.

Although specific embodiments have been illustrated and described herein, it will be appreciated by those of ordinary skill in the art that any arrangement, which is calculated to achieve the same purpose, may be substituted for the specific embodiments shown. Therefore, it is manifestly intended that this invention be limited only by the claims and the equivalents thereof.

What is claimed is:

1. A printed circuit board device, comprising:
a first capacitive sensor configured to measure a first capacitance within a contained volume having known dimensions, wherein the first capacitance changes as a substance is received into the contained volume, wherein the substance is conductive;
a second capacitive sensor including a plurality of corresponding capacitive plates having a plurality of corresponding trigger points at a plurality of corresponding known heights within the contained volume, the second capacitive sensor configured to detect when the substance received into the contained volume has reached each corresponding known height of the plurality of corresponding known heights within the contained volume, wherein each corresponding capacitive plate of the plurality of corresponding capacitive plates has a corresponding trigger point of the plurality of corresponding trigger points, wherein each corresponding trigger point of the plurality of corresponding trigger points is at a corresponding known height of the plurality of corresponding known heights, wherein each corresponding capacitive plate of the plurality of corresponding capacitive plates includes corresponding exposed conductive material, wherein each corresponding capacitive plate of the plurality of corresponding capacitive plates is grounded when the substance touches the corresponding exposed conductive material of the corresponding trigger point of the corresponding capacitive plate, wherein a capacitance reading of the second capacitive sensor has a step change in capacitance when each corresponding capacitive plate is grounded; and wherein at least one of a level of the substance within the contained volume, a volume of the substance within the contained volume, or a flow rate of the substance into the contained volume is determined based on data from the first capacitive sensor and the second capacitive sensor.

2. The printed circuit board device of claim 1, wherein each corresponding trigger point of the plurality of corresponding trigger points includes a point on the second capacitive sensor where an area of the second capacitive sensor changes substantially resulting in the step change in the capacitance reading.

3. The printed circuit board device of claim 1, wherein second data from the second capacitive sensor is used to at least one of calibrate, filter, augment, or correct a determination of the at least one of the level of the substance within the contained volume, the volume of the substance within the contained volume, or the flow rate of the substance into the contained volume based on the first capacitive sensor.

4. The printed circuit board device of claim 1, wherein the first capacitance is indicative of at least one of the level of the substance within the contained volume, the volume of the substance within the contained volume, or the flow rate of the substance into the contained volume.

5. The printed circuit board device of claim 1, wherein the first capacitance is indicative of the level of the substance within the contained volume;

wherein the volume of the substance within the contained volume is determined based on the level of the substance within the contained volume and a known geometry of the contained volume; and wherein the flow rate of the substance within the contained volume is determined by subtracting a first volume determined at a first time from a second volume determined at a second time to determine a difference between the second volume and the first volume and dividing the difference by an elapsed time between the first time and the second time.

6. The printed circuit board device of claim 1, wherein the second capacitive sensor includes a capacitance ladder.

7. The printed circuit board device of claim 1, wherein the substance is a liquid.

8. The printed circuit board device of claim 1, wherein the substance is urine.

9. A substance measurement device, comprising:
a container portion configured to receive a substance, wherein the substance is conductive;
a first capacitive sensor configured to measure a first capacitance related to the substance within the container portion, wherein the first capacitance changes as the substance is received into the container portion;
a second capacitive sensor including a plurality of corresponding capacitive plates having a plurality of corresponding trigger points at a plurality of corresponding known heights within the container portion, the second capacitive sensor configured to detect when the substance received into the container portion has reached each corresponding known height of the plurality of corresponding known heights within the container portion, wherein each corresponding capacitive plate of the plurality of corresponding capacitive plates has a corresponding trigger point of the plurality of corresponding trigger points is at a corresponding known height of the plurality of corresponding known heights, wherein each corresponding capacitive plate of the plurality of corresponding capacitive plates includes corresponding exposed conductive material, wherein each corresponding capacitive plate of the plurality of corresponding capacitive plates is grounded when the substance touches the corresponding exposed conductive material of the corresponding trigger point of the corresponding capacitive plate, wherein a capacitance reading of the second capacitive sensor has a step change in capacitance when each corresponding capacitive plate is grounded; and wherein at least one of a level of the substance within the container portion, a volume of the substance within the container portion, or a flow rate of the substance into the container portion is determined based on data from the first capacitive sensor and the second capacitive sensor.

10. The substance measurement device of claim 9, wherein each corresponding trigger point of the plurality of corresponding trigger points includes a point on the second capacitive sensor where an area of the second capacitive sensor changes substantially resulting in the step change in the capacitance reading.

11. The substance measurement device of claim 9, wherein second data from the second capacitive sensor is used to at least one of calibrate, filter, augment, or correct a determination of the at least one of the level of the substance within the container portion, the volume of the substance within the container portion, or the flow rate of the substance into the container portion based on the first capacitive sensor.

12. The substance measurement device of claim 9, wherein the first capacitance is indicative of at least one of the level of the substance within the container portion, the volume of the substance within the container portion, or the flow rate of the substance into the container portion.

13. The substance measurement device of claim 9, wherein the first capacitance is indicative of the level of the substance within the container portion;

wherein the volume of the substance within the container portion is determined based on the level of the substance within the container portion and a known geometry of the container portion; and wherein the flow rate of the substance within the container portion is determined by subtracting a first volume determined at a first time from a second volume determined at a second time to determine a difference between the second volume and the first volume and dividing the difference by an elapsed time between the first time and the second time.

14. The substance measurement device of claim 9, wherein the second capacitive sensor includes a capacitance ladder.

15. The substance measurement device of claim 9, wherein the first capacitive sensor and the second capacitive sensor are located in close proximity to one another and the second capacitive sensor is used to at least one of calibrate, filter, augment, or correct a determination of at least one of the level of the substance within the container portion, the volume of the substance within the container portion, or the flow rate of the substance into the container portion based on the first capacitive sensor.

16. The substance measurement device of claim 9, wherein the first capacitive sensor and the second capacitive sensor are fabricated on a single printed circuit board.

17. The substance measurement device of claim 9, wherein the substance is a liquid.

18. The substance measurement device of claim 9, wherein the substance is urine.

19. A method, comprising:
sensing a first capacitance within a contained volume at various time points using a first capacitive sensor, wherein the first capacitance changes as a substance is received into the contained volume, wherein the substance is conductive, wherein the contained volume has known dimensions;
detecting when the substance received into the contained volume reaches each corresponding trigger point of a plurality of corresponding trigger points of a plurality of corresponding capacitive plates on a second capacitive sensor at a plurality of corresponding known heights within the contained volume when the substance received into the contained volume reaches each corresponding known height of the plurality of corresponding known heights within the contained volume, wherein each corresponding capacitive plate of the plurality of corresponding capacitive plates has a corresponding trigger point of the plurality of corresponding trigger points, wherein each corresponding trigger point of the plurality of corresponding trigger points is at a corresponding known height of the plurality of corresponding known heights, wherein each corresponding capacitive plate of the plurality of corresponding capacitive plates includes corresponding exposed conductive material, wherein each corresponding capacitive plate of the plurality of corresponding capacitive plates is grounded when the substance touches the corresponding exposed conductive material of the corresponding trigger point of the corresponding capacitive plate, wherein a capacitance reading of the second capacitive sensor has a step change in capacitance when each corresponding capacitive plate is grounded; and
determining at least one of a level of the substance within the contained volume, a volume of the substance within the contained volume, or a flow rate of the substance into the contained volume based on the first capacitance at the various time points and when the contained volume reaches each corresponding known height of the plurality of corresponding known heights within the contained volume.

20. The method of claim 19, wherein each corresponding trigger point of the plurality of corresponding trigger points includes a point on the second capacitive sensor where an area of the second capacitive sensor changes substantially resulting in the step change in the capacitance reading.

21. The method of claim 19, wherein a determination of when the contained volume reaches each corresponding known height of the plurality of corresponding known heights within the contained volume is used for at least one of calibrating, filtering, augmenting, or correcting a second determination of at least one of the level of the substance within the contained volume, the volume of the substance within the contained volume, or the flow rate of the substance into the contained volume.

22. The method of claim 19, wherein the first capacitance is indicative of at least one of the level of the substance within the contained volume, the volume of the substance within the contained volume, or the flow rate of the substance into the contained volume.

23. The method of claim 19, further comprising:
wherein the first capacitance is indicative of the level of the substance within the contained volume;
determining the volume of the substance within the contained volume based on the level of the substance within the contained volume and a known geometry of the contained volume; and
determining the flow rate of the substance within the contained volume by subtracting a first volume determined at a first time from a second volume determined at a second time to determine a difference between the second volume and the first volume and dividing the difference by an elapsed time between the first time and the second time.

24. The method of claim 19, wherein the substance is a liquid.

25. The method of claim 19, wherein the substance is urine.

* * * * *